(12) United States Patent
Fujita et al.

(10) Patent No.: US 6,835,720 B2
(45) Date of Patent: Dec. 28, 2004

(54) COMPOUNDS HAVING ANTIVIRAL ACTIVITY

(75) Inventors: Shuji Fujita, Tokorozawa (JP);
Masaaki Numata, Tokorozawa (JP);
Kazuo Suzuki, Tokorozawa (JP);
Shigeki Nunomura, Tokorozawa (JP);
Mamoru Sugimoto, Kusatsu (JP);
Masaki Terada, Kusatsu (JP)

(73) Assignee: Nissin Food Products Co., Ltd., Osaka (JP)

( * ) Notice: Subject to any disclaimer, the term of this patent is extended or adjusted under 35 U.S.C. 154(b) by 0 days.

(21) Appl. No.: 10/252,036

(22) Filed: Sep. 23, 2002

(65) Prior Publication Data

US 2003/0073664 A1 Apr. 17, 2003

Related U.S. Application Data

(60) Continuation of application No. 09/984,920, filed on Oct. 31, 2001, now Pat. No. 6,541,461, which is a division of application No. 09/180,618, filed as application No. PCT/JP97/01654 on May 16, 1997, now Pat. No. 6,337,390.

(30) Foreign Application Priority Data

May 16, 1996 (JP) .............................. 8-122025

(51) Int. Cl.[7] .................... A61K 31/70; C07H 15/00
(52) U.S. Cl. ........................ 514/71; 514/25; 536/53; 536/4.1
(58) Field of Search .................... 514/25, 71; 536/53, 536/41

(56) References Cited

U.S. PATENT DOCUMENTS

| | | |
|---|---|---|
| 5,637,690 A | 6/1997 | Lee et al. |
| 6,337,390 B1 * | 1/2002 | Fujita et al. ................. 536/4.1 |
| 6,541,461 B2 * | 4/2003 | Fujita et al. ................. 514/71 |
| 2002/0077472 A1 * | 6/2002 | Fujita et al. ................. 536/53 |

FOREIGN PATENT DOCUMENTS

| | | |
|---|---|---|
| EP | 0 587 347 A2 | 3/1994 |
| EP | 0 587 374 A2 | 3/1994 |
| EP | 587 374 A2 | 3/1994 |
| EP | 0 671 407 A2 | 9/1995 |
| EP | 0 771 815 A1 | 5/1997 |
| JP | A-59-164798 | 9/1984 |
| JP | A-61-243096 | 10/1986 |
| JP | A-63-45223 | 2/1988 |
| JP | A-63-45233 | 2/1988 |
| JP | A-63-264493 | 11/1988 |
| JP | A-64-52794 | 2/1989 |
| JP | A-1-125394 | 5/1989 |
| JP | A-2-304025 | 12/1990 |
| JP | A 03 17020 | 1/1991 |
| JP | A-3-17020 | 1/1991 |
| JP | H03-017020 | 1/1991 |
| JP | A-3-246297 | 11/1991 |
| JP | A-4-136001 | 5/1992 |
| JP | A-6-234788 | 8/1994 |
| JP | A-6-256373 | 9/1994 |
| JP | A-8-41093 | 2/1996 |

OTHER PUBLICATIONS

S. Saito et al., "Synthetic Studies on the Relationship Betwen Anti–HIV Activities and Micelle Forming Abilities of Various Alkylated Glycyrrhetinate Diglycoside Sodium Sulfates and Related Compounds", *Eur. J. Med. Chem.* vol. 31, No. 5, pp. 365–381, (1996).

(List continued on next page.)

*Primary Examiner*—James O. Wilson
*Assistant Examiner*—Devesh Khare
(74) *Attorney, Agent, or Firm*—Oliff & Berridge, PLC

(57) ABSTRACT

In order to provide the anti-retrovirus active compound with low anti-coagulant action and low cytotoxicity, compounds comprising glycoside or the salt thereof wherein lipid is linked to position 2 of sialic acid having all hydroxyl groups at positions 4, 7, 8 and 9 completely sulfated, or KDN (2-keto-3-deoxy-D-glycero-2-nononic acid) having all hydroxyl groups at positions 4, 5, 7, 8 and 9 completely sulfated are provided.

28 Claims, 16 Drawing Sheets

OTHER PUBLICATIONS

T. Bocker et al., "Synthesis and Properties of Sulfated Alkyl Glycosides", *Carbohydr. Res.*, vol. 230, No. 2, pp. 245–256, (1992).

Yoshida et al., "Synthesis of chemically modified sialic acid–containing sialyl–Lex ganglioside analogues recognized by the selectin family", Glycoconjugate Journal, vol. 10, pp. 3–15, 1993.

Bevilacqua et al., "Selectins", J. Clin. Invest., vol. 91, pp. 379–387, 1993.

Hasegawa et al., "Studies of the Thioglycosides of N–Acetyl–neuraminic acid 8: Synthesis of S–(alpha–sialyl)–(2—>6)–beta–hexopyranosyl and –(2—>6)–beta–lactosyl ceramides containing beta–thioglycosidically linked ceramide", vol. 10(6): 1009–1021.

International Union of Pure and Applied Chemistry, Pure and Applied Chemistry, vol. 67: 1348.

Journal of Medical Chemistry, *Monovalent Sialosides that Bind Tightly to Influenza A Virus*, P.L. Toogood et al., vol. 34, No. 10, pp. 3138–3140 (1991).

Carbohydrate Research, *Synthesis and Properties of Sulfated Alkyl Glycosides*, T. Bocher et al., vol. 230, No. 2, pp. 245–256 (1992).

European Journal of Medical Chemistry, *Synthetic Studies on the Relationship Between Anti–HIV Activities and Micelle Forming Abilities of Various Alkylated Glycyrrhetinate Dislycoside Sodium Sulfates and Related Compounds*, S. Saito et al., vol. 31, No. 5, pp. 365–381 (1996).

Antimicrobial Agents and Chemotherapy, *Novel Sulfated Polymers as highly Potent and Selective Inhibitors of Human Immunodeficiency Virus Replication and Giant Cell Formation*, pp. 134–138 (1990).

Inoue, Yasuo et al., Seitai Bunsi no Kagaku, Tositu no Kagaku (Chemistry of Biomolecules 1, Chemistry of Carbohydrates, pp. 80–81.

Chemische Berichte, *Synthese Anomerer Sialinsäure–Methylketoside*, Richard Kuhn et al., pp. 611–617 (1966).

Agric. Biol. Chem., *Synthesis of 3–0–Glycosyl–1, 2–di–0–tetradecyl–sn–glycerol*, Tomoya Ogawa et al., pp. 255–262 (1982).

J. Am. Chem. Soc., *Hyperextended Amphiphiles. Bilayer Formation from Single–Tailed Compounds*, F.M. Menger et al., pp. 3840–3841 (1993).

Agr. Biol. Chem., *Syntheses of Female Sex Pheromone Analogues of the German Cockroach and their Biological Activity*, Tetsuo Sato et al., vol. 40, pp. 391–394 (1976).

Chem. Pharm. Bull., *Studies on Sialic Acids. XXV. Synthesis of the α and β–N–Glycosides of 3–Deoxy–D–glycero–D–galacto–2–nonulosonic Acid (KDN)*, Mitsunobu Nakamura et al., vol. 39, pp. 3140–3144 (1991).

J. Carbohydrate Chemistyr, *Studies on the Thioglycosides of N–Acetylneuraminic Acid 1: Synthesis of Alkyl α–Glycosides of 2–Thio–N–Acetylneuraminic Acid*, Akira Hasegawa et al., pp. 11–19 (1986).

Carbohydrate Research, *A Total Synthesis of Hematoside*, Masaaki Numata et al., vol. 174, pp. 73–85 (1988).

Thomas Boecker et al., "Synthesis and Properties of Sulfated Alkyl Glycosides, " Carbohydrate Research, vol. 230, 245–256, 1992.

* cited by examiner

Example 7

Example 8

Example 9

Example 10

Example 11

Example 12

Example 13

Example 14

Example 15

Example 16

Example 17

Example 18

Example 19

Example 20

Example 21

Example 22

Example 23

Example 24

Example 25

A

B

Example 26

Example 27

Example 28

Example 29

Example 30

Example 31

Example 32

Example 33

Example 34

Example 35

Example 36

A

B

C

Lev = CH$_3$COCH$_2$CH$_2$CO

Example 37

Example 38

Example 39

Example 40

Example 41

Example 42

Example 43

Example 44

Example 45

Example 46

Example 47

Example 48

Example 49

Example 50

Example 51

Example 52

Example 53

Example 54

Example 55

Example 56

Example 57

Example 58

Example 59

Example 60

Example 64

Example 65

Example 66

Example 67

ABBREVIATIONS

Bn : CH$_2$   Ac : CH$_3$CO   Ms : CH$_3$SO$_2$   Lev : CH$_3$COCH$_2$CH$_2$CO

COMPOUNDS HAVING ANTIVIRAL ACTIVITY

This is a continuation of application Ser. No. 09/984,920 filed Oct. 31, 2001 now U.S. Pat. No. 6,541,461 which in turn is a Divisional of application Ser. No. 09/180,618 filed Jan. 19, 1999, now U.S. Pat. No. 6,337,390, which in turn in the U.S. National Stage of International Application No. PCT/JP97/01654 filed May 16, 1997. The entire disclosure of the prior application is hereby incorporated by reference herein in its entirety.

BACKGROUND OF THE INVENTION

1. Field of the Invention

This invention relates to a novel compound with the anti-viral activity and a drug and anti-viral agent containing said compound as the effective ingredient, more specifically relates to a medicine and anti-HIV active compound comprising the sulfated nonulonic acid.

2. Description of the Related Arts

Azidothymidine (AZT) and dideoxy inosine (DDI) have been used as the AIDS remedy. These agents are to inhibit the reverse transcriptase of HIV, bringing about apothanasic effect to patients, while posing problems that the chronic administration of AZT causes myelopathy and that the DDI administration results in side reactions such as acute pancreatitis and peripheral neuropathy. Furthermore, the use of either drug eventually results in the generation of virus resistant to these drugs.

Recently, the sulfated polysaccharide has been expected as a promising AIDS remedy. It is well known that polysulfated compounds such as dextransulfate (I) (Japanese Patent Laid-Open Publication No. Sho63-45233), polyvinyl alcohol sulfate (II) (Antimicrob. Agents Chemother. 34, 134–138 (1990)), oligosaccharide sulfate (Japanese Patent Laid-Open Publication No. Hei2-304025) inhibit the proliferation of HIV. These compounds are produced simply by binding the sulfate group to polysaccharides, oligosaccharides or organic polymeric molecules.

In addition, the sulfated modified cyclodextrin (III) is cyclodextrin to which lipid-soluble groups such as aryl-, alkyl-groups are introduced, and also has the proliferation inhibiting activity against retroviruses, HIV in particular (Japanese Patent Laid-Open Publication No. Hei4-136001).

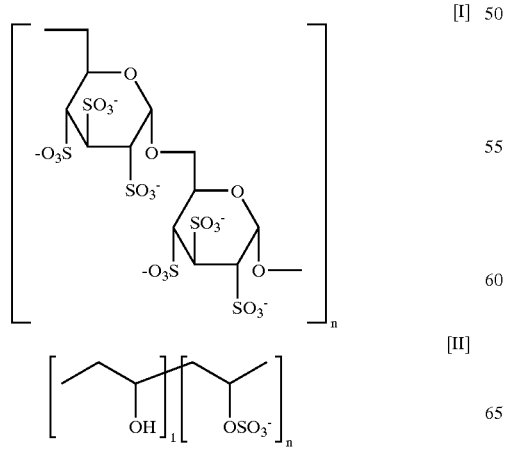

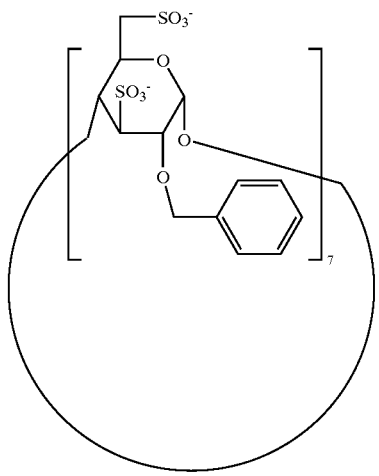

In addition, as a virucide comprising the sulfated polysaccharide as the active ingredient is disclosed the one using an acyl derivative of a sulfated oligosaccharide glycoside (Japanese Patent Laid-Open Publication No. Hei6-256373).

At first, it was conceived that the virucidic activity of sulfated polysaccharides was due to their reverse transcriptase inhibiting activities, and now it is thought to be due to the interaction between the sulfated polysaccharide and the coat protein gp120 of HIV.

However, since sulfated polysaccharides generally have the inhibitory activity for the blood coagulation system (anticoagulant activity), they have not been accepted as the suitable medicine.

DISCLOSURE OF THE INVENTION

This invention has been developed in view of the above-mentioned problems, aiming at providing the anti-viral compound with a relatively weak anti-blood coagulating activity and a low cytotoxicity, especially the one with the anti-HIV activity.

The present inventors have actively pursued the study to resolve the above-mentioned problems, establishing that the following compounds are useful for attaining the above-described purpose and completing the present invention.

(1) A compound having all hydroxyl groups of the sugar moiety of glycoside comprising monosaccharide-lipid sulfated or the salt thereof, wherein said lipid moiety is bound to the anomeric position of said sugar moiety.

(2) The compound or the salt thereof according to (1), wherein said sugar and lipid moieties are connected by the O-glycosidic linkage or the S-glycosidic linkage.

(3) The compound or the salt thereof according to (2), wherein said lipid is linear, and said linear lipid has a branched structure.

(4) A compound or the salt thereof, wherein all hydroxyl groups of nonuloic acid moiety of the glycoside comprising a monosaccharide-lipid with said lipid bound to the anomeric position of nonuroic acid derivative are sulfated.

(5) A compound or the salt thereof, wherein all hydroxyl groups of sialic acid moiety or KDN moiety of the glycoside comprising a monosaccaride-lipid with said lipid bound to the anomeric position of sialic acid or KDN are sulfated.

(6) The compounds or the salts thereof according to (5), wherein the binding of said sialic acid moiety or KDN moiety to the lipid moiety is either the O-glycosidic of S-glycosidic linkage at position 2 of said moiety or the amidic linkage at position 1 of said residue.

(7) The compound or the salt thereof according to (6), wherein said lipid is a linear lipid, and this lipid has a branched structure.

(8) The compound or the salt thereof according to (7), wherein said branched chain is localized at position 2 of the main chain of said lipid moiety.

(9) The compound or the salt thereof according to (8), wherein said lipid moiety has a forked two chain structure due to said branching.

(10) The compound or the salt thereof according to (9), wherein said lipid moiety has an alkyl group with the skeleton-forming carbon atoms from 1 to 4 at said branching site.

(11) The compound or the salt thereof according to (9) or (10), wherein the total number of said lipid skeleton-forming atoms is from 22 to 60.

(12) The compound or the salt thereof according to (11), wherein said branched chain comprises a carbon-carbon unsaturated bond.

(13) The compound or the salt thereof according to (11), wherein said branched chain is linear.

(14) The compound or the salt thereof according to (11), wherein said branched chain has an ester linkage or ether linkage, respectively.

(15) The compound or the salt thereof according to (14), wherein said ester linkage or ether linkage is localized at positions 1 or 2 of said branched chain.

(16) The compound or the salt thereof according to (11), wherein the number of skeleton-forming atoms is from 10 to 28 per one branched chain.

(17) The compound or the salt thereof according to (16), wherein the number of skeleton-forming atoms is from 18 to 26 per one branched chain.

(18) The compound or the salt thereof according to (17), wherein the number of skeleton-forming atoms is from 24 per one branched chain.

(19) The compound or the salt thereof according to (18), wherein said forked branched chains are of the same length, respectively.

(20) The compound or the salt thereof according to (19), wherein said forked branched chains are of the same, respectively.

(21) The compound or the salt thereof according to (20), wherein said branched chain has the ester bond or the ether linkage at its position 1 or 2.

(22) The compound or the salt thereof according to (21), wherein said branched chain is linear.

(23) A medicine comprising the compound according to anyone of (1) to (3) in a pharmaceutically effective dosage.

(24) An antiviral drug containing the compound according to anyone of (1) to (3) in a pharmaceutically effective dose.

(25) An anti-HIV drug containing the compound according to anyone of (1) to (3) in a pharmaceutically effective dose.

(26) A drug containing the compound according to anyone of (1) to (21) in a pharmaceutically effective dose.

(27) An antiviral drug containing the compound according to anyone of (1) to (21) in a pharmaceutically effective dose.

(28) An anti-HIV drug containing the compound according to anyone of (1) to (21) in a pharmaceutically effective dose.

Drugs (23 and 26), furthermore, antiviral drugs (24 and 27), especially anti-HIV drugs (24 and 27) containing compounds according to any one of the above-described (1) to (22) are within the scope of the present invention. However, since drugs, anti-viral drugs and anti-HIV drugs containing the compounds according to any one of the above-described (5) to (22) in pharmaceutically effective doses have lower anti-coagulant activity as well as lower biological toxicity than those containing compounds according to any one of the above-described (1) to (3), the former group of drugs are pharmaceutically useful. It has been confirmed that, of the above-described compounds, particularly, those having 24 skeleton-forming atoms per one branched chain (24), furthermore, each of said branched chains of which has the same structure, is linear and has the ether bond at its position 1 or 2, are pharmaceutically useful (examples 12, 13, 29, 50 and 59).

And, the usage of drugs, anti-viral drugs and anti-HIV drugs containing the compound according to any one of the above-described (1) and (22) as the drugs, anti-viral drugs and anti-HIV drugs, and the method for treating the particular diseases (viral disease and acquired immune deficiency syndrome caused by HIV) are also within the scope of the present invention.

BEST MODE FOR CARRYING OUT THE INVENTION

Definition of the Terms

As used in this specification, by the term "nonuloic acid" is meant the same nonuloic acid as used generally, an acidic carbohydrate having a carboxyl group at its position 1 and 9 carbon atoms. Accordingly, "nonuloic acid derivatives" used in this specification include neuraminic acid (5-amino-3,5-dideoxy-D-glycero-D-galacto-nonuloic acid) and neuraminic acid derivatives. Since the later-described "sialic acid" is an acyl derivative of neuraminic acid, it is also included in "nonuloic acid derivatives".

By "KDN" used in this specification is meant 2-keto-3-deoxy-D-glycero-2-nononic acid. And, by "sialic acid used in this specification is meant the generic name for a series of derivatives of substances having the neuraminic acid as the basic structure (Yasuo Inoue, Seitai Bunsi no Kagaku, Tositu no Kagaku (Chemistry of Biomolecules 1, Chemistry of Carbohydrates), p80–81, Baifukan), and acyl derivatives, more specifically, such as N-acetylneuramic acid and N-glycolylneuramic acid are also included therein.

By "forked two chains" (for example, (9)) is meant a structure constructed with two chains having more than 7 skeleton-forming atoms. Accordingly, alkyl groups according to (10), wherein the total number of their skeleton-forming atoms is 1 to 4, are not included in "chain" constructing "forked two chains".

By "skeleton-forming atoms" is meant atoms constructing the skeleton of the chain, including carbon atom, oxygen atom, nitrogen atom, sulfur atom, etc. However, monovalent atom, such as hydrogen atom, is not included in the "skeleton-forming atoms", because it cannot construct the skeleton portion of the chain.

By "salt" is meant the sodium and potassium salts which are required to neutralize the intramolecular carboxylic acid and sulfonic acid, to which cations bind so as not to decrease the biological activity. As to the cations bound to said acids, any cations which do not lower the biological activity of the compounds related to the present invention may be used.

Sugars

In principle, the compound related to this invention is a glycosidic compound and the salt thereof comprising a sugar-lipid with said lipid bound to the anomeric carbon of said sugar, wherein hydroxyl groups of said sugar moiety are all sulfated, having an excellent anti-retroviral activity (the above-described (1)). Although there have been hitherto found the sulfated sugars with the anti-retroviral activity, the glycoside comprising a sugar-lipid with sulfate group introduced and having the anti-retroviral activity has not been discovered. In this respect, this invention is valuable in finding that a glycoside comprising a sugar-lipid with the sulfate groups filly (100%) introduced or the derivative thereof has an excellent anti-viral activity.

When the sugar moiety of said glycoside is sialic acid or KDN, the glycoside not only has the strong anti-viral activity, but also lower cytotoxicity, and can preferably achieve the main purpose as medicine (the above-described (5) to (22), (26) to (28)). And, in this case, the hydroxyl groups of the sugar moiety of the compound related to the present invention to be all sulfated to form the wholly sulfated nonulonic acid (the above-described (4)) are at positions 4, 7, 8 and 9 when nonulonic acid is N-acetylneuraniic acid, and the glycolyl hydroxyl group at position 5, in addition to the hydroxyl groups at the positions 4, 7, 8 and 9. In the case wherein nonulonic acid is KDN, all the hydroxyl groups at positions 4, 5, 7, 8 and 9 are sulfated.

The bond between the monosaccharide moiety and lipid moiety of the compound related to the present invention can be of any type. Accordingly, the bond between the monosaccharide and lipid may be not only the O-glycosidic linkage but also S-glycosidic linkage. Furthermore, in the case where the sugar moiety of the compound related to the present invention is nonuloic acid, the ainide linkage and ester linkage can be formed using the carboxyl group at position 1, in addition to a glycosidic linkage with the carbon atom at position 2. The bond between monosaccharide and lipid in the compound related to the present invention can be such amide linkage and ester linkage. Therefore, although, by "glycoside" is generally meant a compound wherein the monosaccharide and lipid moieties are linked by a glycosidic linkage, by "glycoside" in this specification is meant a compound wherein the monosaccharide and lipid are bonded not only in a glycosidic linkage but also in amide and ester linkages. Accordingly, not only compounds having a glycosidic linkage at position 1 of monosaccharide such as glucose or position 2 of nonulonic acid but also those having an amide linkage or ester linkage at position 1 of nonulonic acid are also in the scope of "glycoside" of the present invention.

However, in consideration of the overall manufacturing easiness and biological activity of these compounds, glycosides with the O-glycosidic, S-glycosidic, and amide linkages are preferred.

Lipids

By "lipid" in the compound related to this invention is meant the lipid in a broad sense including steroid, carotinoid, terpenoid, etc., and conceptually even the compound such as cholesterol. However, the compound related to this invention is preferably a linear lipid, which further preferably has the branched chain structure (the above-described (7)). The branch can be two-forked or three-forked, located at position 2 of the main chain of the lipid moiety. As a result, the lipid is preferably two-forked at the β position (β position with respect to the sugar moiety) of said lipid moiety (the above-described (8) and (9)). Furthermore, this branching site may have alkyl group with the skeleton-forming atoms 1 to 4 (the above-described (10)). "Alkyl group with the skeleton-forming atoms 1 to 4" herein cited includes, for example, methyl group, ethyl group, propyl group etc.

The above-described two-forked chain can be a hydrocarbon chain, which can include heteroatoms such as oxygen, nitrogen, sulfur, etc. Furthermore, regardless of the species of component atoms, the total number of the skeleton-forming atoms of lipid is preferably 22 to 60 (the above-described (11)). In addition, the above-described two-forked chains can have unsaturated bond between carbon atoms, respectively (the above-described (12)). Also, although the above-described two-forked chain can be further branched, they are preferably linear (the above-described (13)).

In the case where the above-described two-forked chain contains heteroatoms as the component atom, each branched chain preferably contains an ester bond or ether bond (the above-described (14)), furthermore, said ester bond or ether bond is preferably localized at position 1 or 2 of said branched chain (the above-described (15)).

Herein, when the ester bond or ether bond is present at position 1 of the branched chain, the compound related to this invention will become the sulfated derivative of sialoglycerolipid with the excellent anti-retroviral activity (In this connection, in the case of ether bond present, said compound will be an alkyl glycerol wherein a long-chain alcohol is linked to the glycerol residue, and in the case of ester bond present, said compound will be amyl glycerol.). Furthermore, in the case where ester bond or ether bond is located at position 2 of the branched chain, the glycerol residue in the glycerol area is suitably modified to become pseud-glycerol.

As to the length of branched chains, the number of skeleton-forming atom is preferably 10 to 28 (the above-described (18)), more preferably 18 to 26 (the above-described (17)), most preferably 24 (the above-described (18)). In addition, forked-chains can be of different lengths, but preferably of the same length (the above-described (19)), most preferably of the same structure comprised of the same component atoms (the above-described (20)).

Method of Administration

When compounds related to the present invention are used as therapeutics, they are administered singly or in combination with pharmaceutically acceptable medical carriers, either organic or inorganic and either solid or liquid. Their compositions are determined according to the solubility, chemical property, administration route and schedule of compounds.

Compounds related to this invention can be administered by any suitable desired administration routes. More specifically, compounds related to this invention can be administered intraperitoneally, subcutaneously, percutaneously, intravenously or intra-arterially, and locally injected in the case of animals, and intravenously, intra-arterially, by local injection, intraperitoneally/intrapleurally, orally, subcutaneously, intramuscularly, sublingually, percutaneously, inhalationally or rectally in the case of humans.

Dosage Form

When compounds related to the present invention are administered as the drug, they can be administered, according to the method and purpose of their administration, in the form of injection, suspension, tablet, granule, powder, capsule, ointment, cream, suppository, tape, etc. For preparing these drugs, solvent, solubilizing agent, isotonizing agent, preservative, anti-oxidant, excipient, binder, lubricant, stabilizer, etc. can be added.

Solvents are exemplified, for example, by water, physiological sodium chloride solution, etc.; solubilizing agents, for example, by ethanol, polysorbates, chromophore, etc.; excipients, for example, by lactic acid, sucrose, starch, cellulose, crystalline cellulose, dextrin, mannitol, maltose, kaolin, calcium hydrogenphosphate, light anhydrous silicic acid, calcium carbonate, etc.; binders, for example, by starch, polyvinylpyrrolidone, hydroxypropyl cellulose, ethyl cellulose, carboxymethyl cellulose, gum arabic, etc.; disintegrators, for example, by starch, calcium carboxymethyl cellulose, etc.; lubricants, for example, by magnesium stearate, talc, hydrogenated oil, etc.; stabilizers, for example, by lactose, mannitol, maltose, polysorbates, macrogols, polyoxyethylene hydrogenated castor oil, etc. Furthermore, glycerol, dimethylacetamide, 70% sodium lactate, surfactant, basic substances (such as sodium hydroxide, ethylenediamine, ethanolamine, sodium carbonate, arginine, meglumine, tris-aminomethane) may be added, if needed. Using these components, compounds related to this invention can be prepared to the dosage forms such as injections, tablets, granules, capsules, etc.

Compounds related to this invention can be administered orally in dosage forms such as granule, fine granule, powder, tablet, heavy syrup, soft capsule, syrup, emulsion, suspension, liposome, liquid preparation, etc. Liquid preparations such as emulsion, syrup, suspension, liquid drug, etc. for oral administration comprise generally used inert diluents, for example, water or vegetable oil. These preparations can also include supplements, for example, moistening agents, suspending agents, sweetening agents, aromatics, coloring matters, preservatives, etc., in addition to these inert diluents. Liquid preparations may be enveloped in capsules made of absorbable materials such as gelatin.

For administration by intravenous, intramuscular and subcutaneous injections, compounds may be made in powder form for injection, and prepared for injection prior to use. Solvents or suspending agents for preparing drugs for parenteral administration, that is, injections, etc. are exemplified, for example, by water, propylene glycol, polyethylene glycol, benzylalcohol, ethyl oleate, lecithin, etc. Preparation of pharmaceutics can be carried out according to the conventional method.

Treatment

It is desirable that clinical dosages are appropriately increased and/or decreased according to the age, symptom, presence or absence of simultaneous administration of other drugs. The daily dosage of compounds related to this invention may be administered once daily, or in two or three divided portions at appropriate intervals, or intermittently. In view of results of animal experiments and various conditions, dosages of compounds related to this invention are determined such that the total dosage does not exceed a certain limit regardless of whether they are administered once or repeatedly. Needless to say that the optimum dosage is varied according to the method of administration, conditions of patients or animals to be treated such as age, body weight, sex, susceptibility, food (diet), time of administration, drugs in joint use, patient's conditions, severity of symptoms, etc. In addition, the optimal dosage and administration frequency under the certain conditions must be determined by the suitable usage determination test performed by a medical specialist according to the above-describe guideline.

EXAMPLES

Synthesis of Compounds

Example 1

Figure 1A:
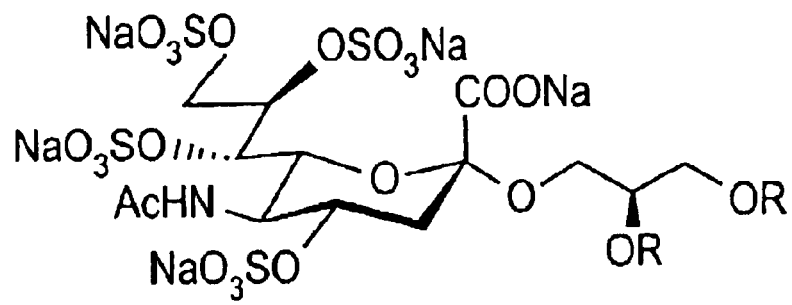
FIG. 1 is a graphic representation of the dependency of biological activity of two-forked alkylglycerol with a glycosidic linkage on the chain length
Figure 1B:
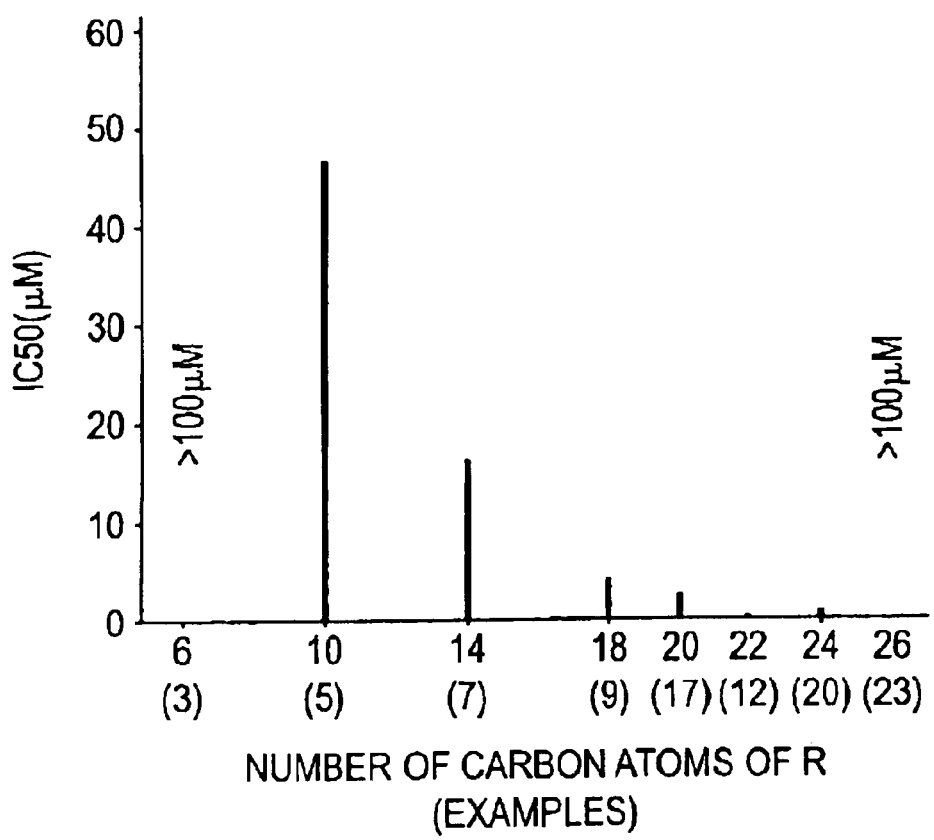
Figure 2:
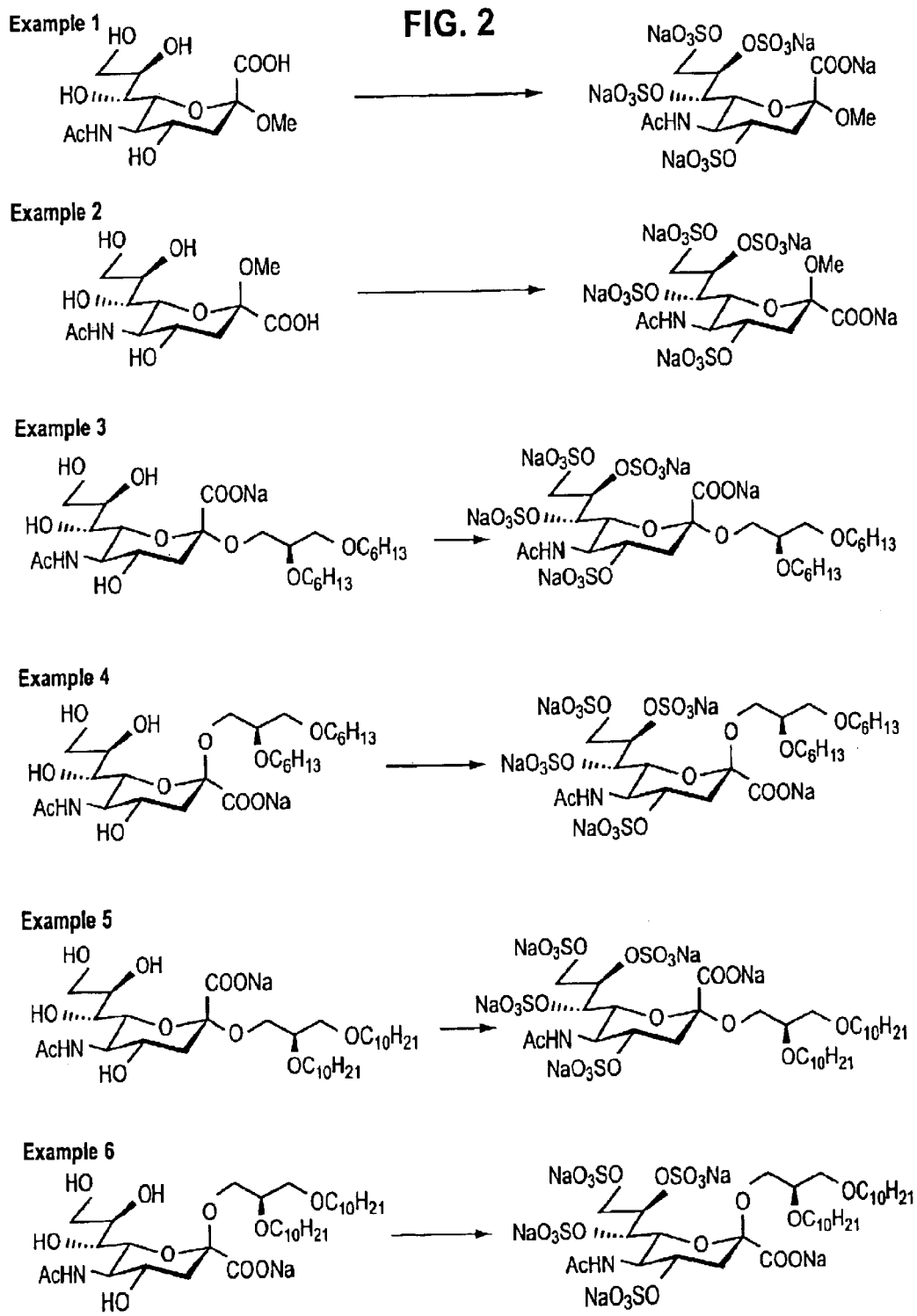
FIG. 2 is a diagram showing the reaction pathway from Examples 1 to 6.
Figure 3:
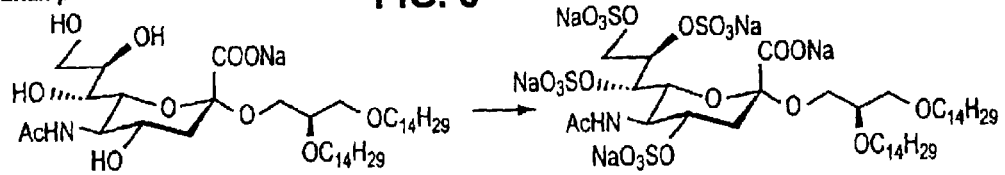
FIG. 3 is a diagram showing the reaction pathway from Examples 7 to 12.
Figure 3:
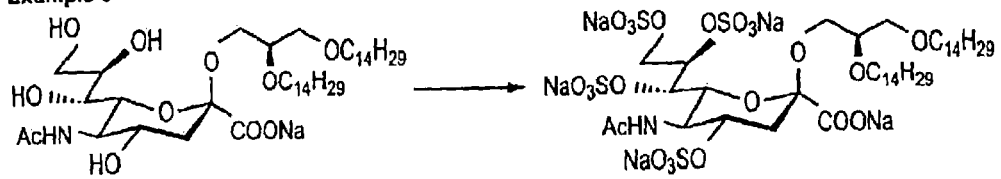
Figure 3:
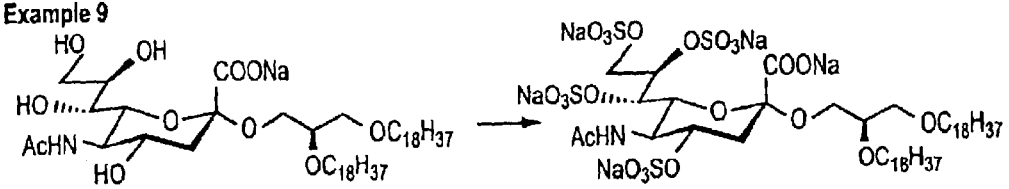
Figure 3:
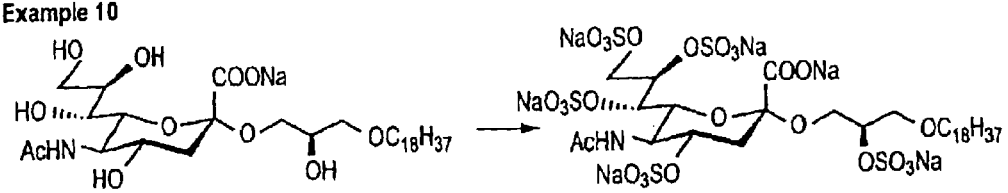
Figure 3:
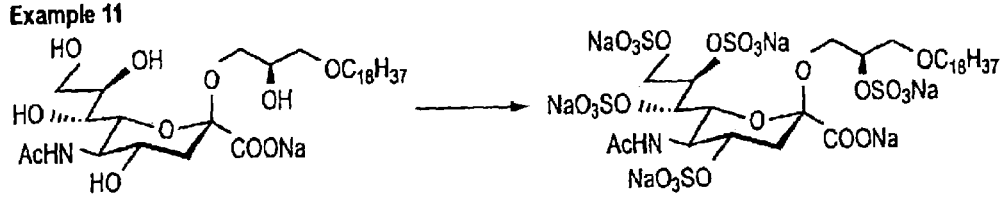
Figure 3:
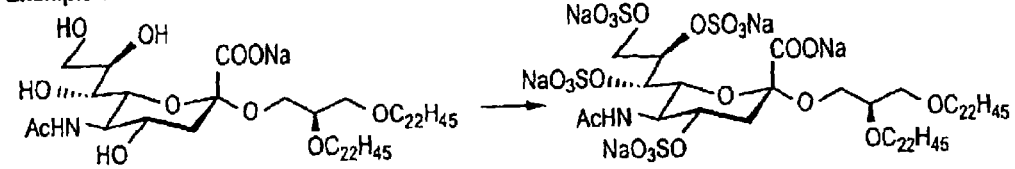
Figure 4:
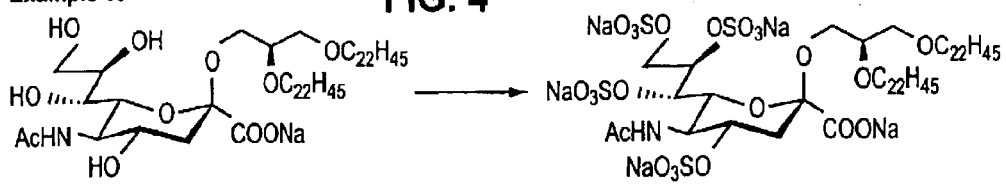
FIG. 4 is a diagram showing the reaction pathway from Examples 13 to 17.
Figure 4:
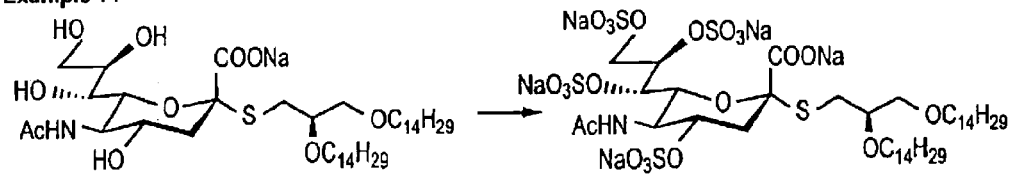
Figure 4:
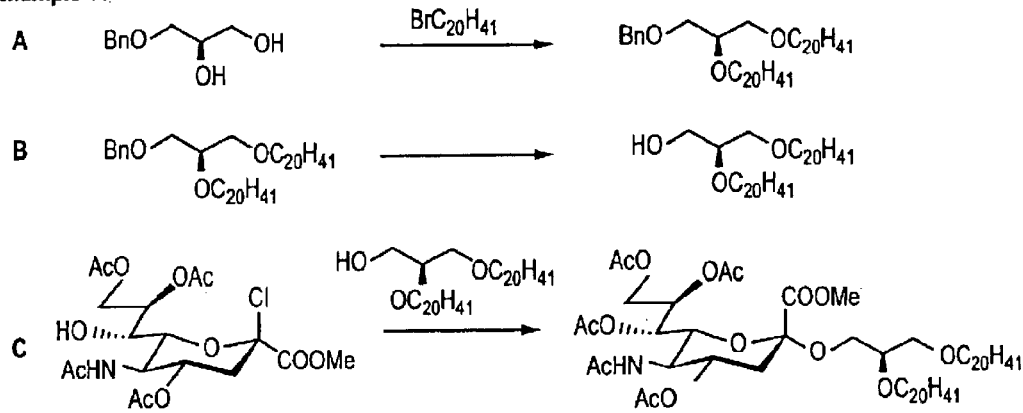
Figure 4:
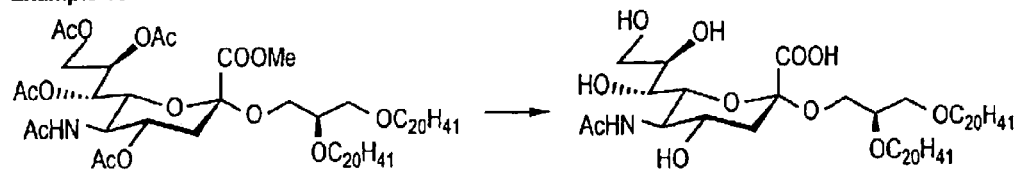
Figure 4:
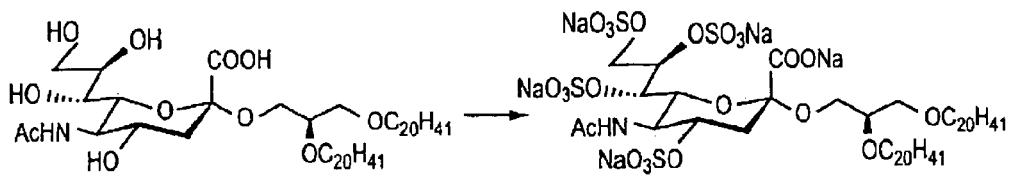
Figure 5:
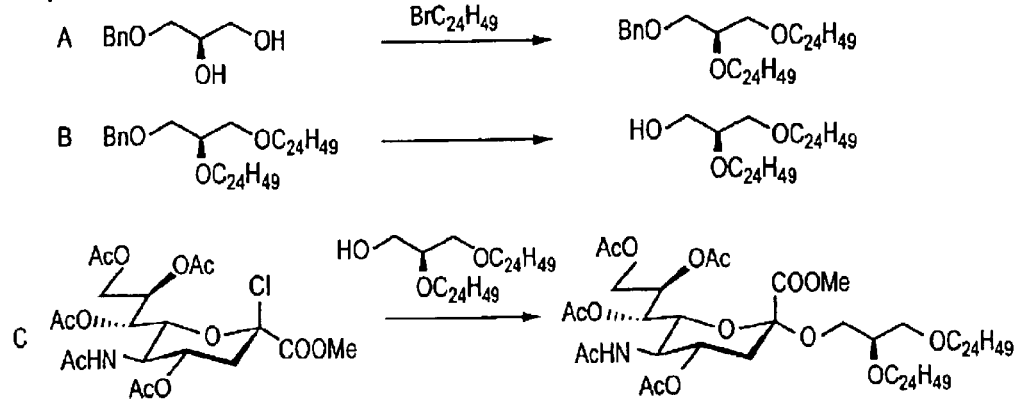
FIG. 5 is a diagram showing the reaction pathway from Examples 18 to 21.
Figure 5:
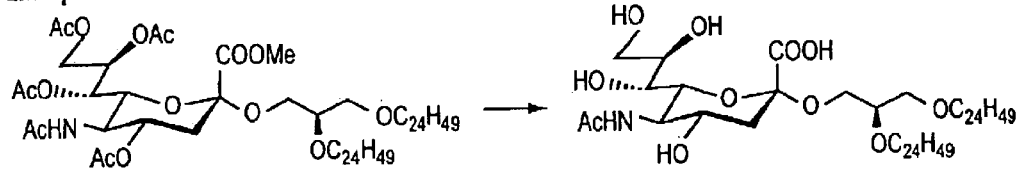
Figure 5:
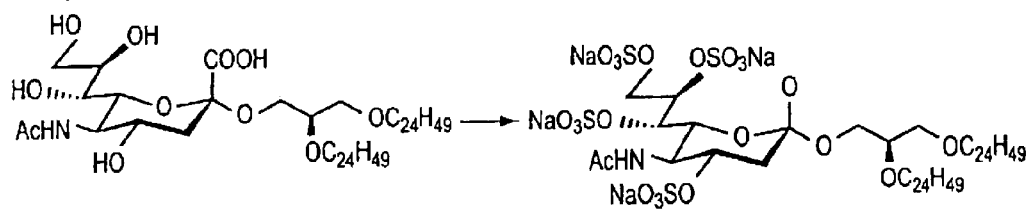
Figure 5:
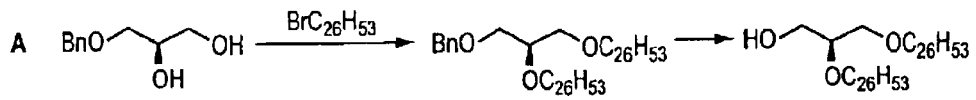
Figure 5:
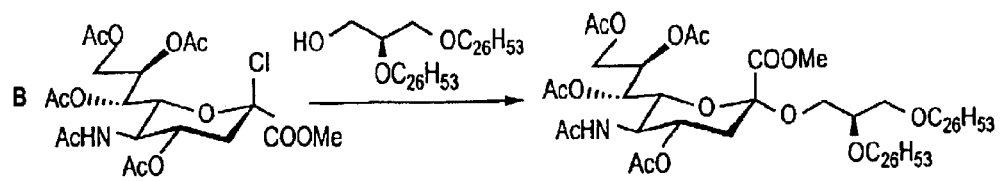
Figure 6:
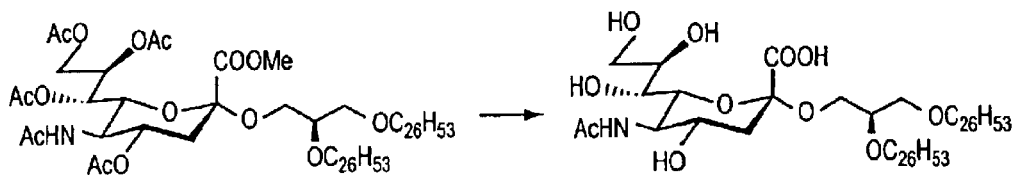
FIG. 6 is a diagram showing the reaction pathway from Examples 22 to 25.
Figure 6:
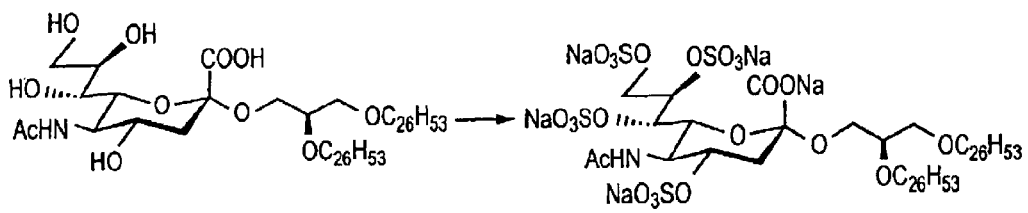
Figure 6:
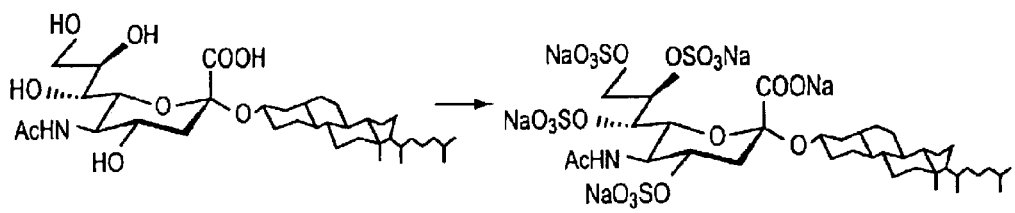
Figure 6:
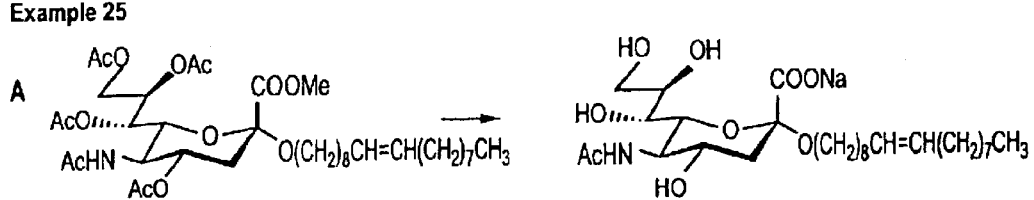
Figure 6:
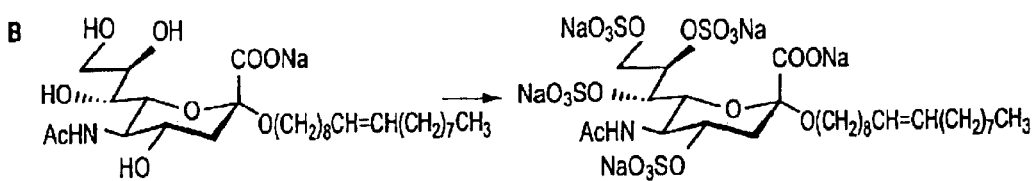
Figure 7:
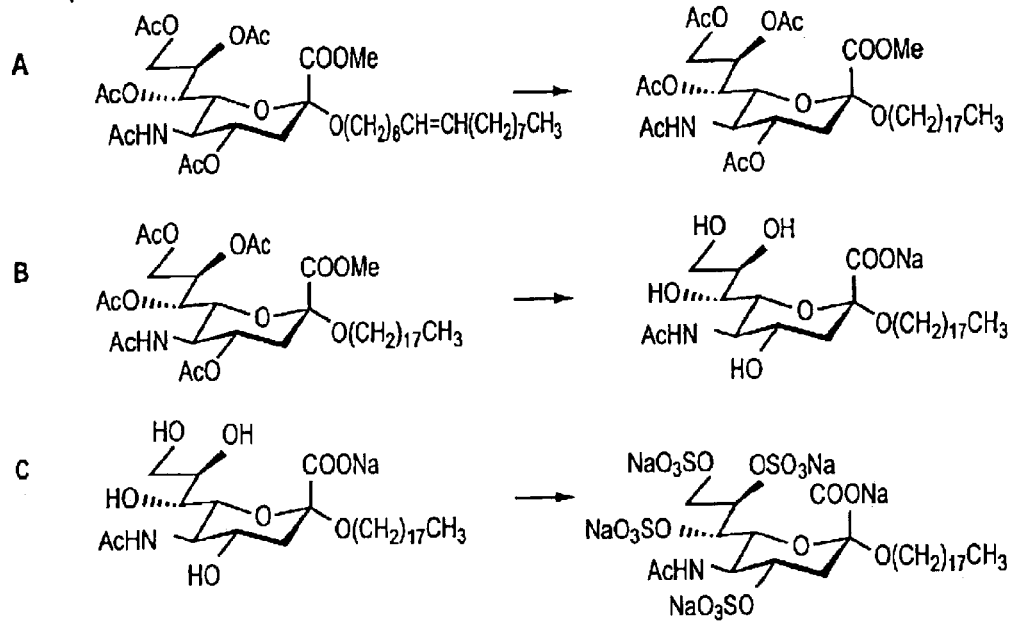
FIG. 7 is a diagram showing the reaction pathway from Examples 26 to 29.
Figure 7:
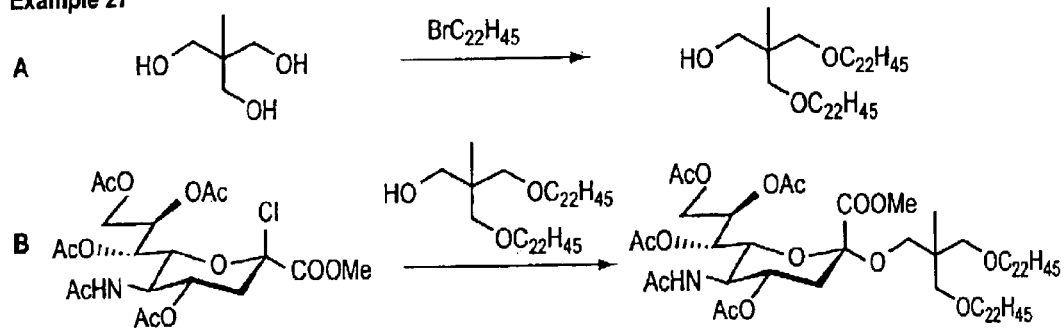
Figure 7:
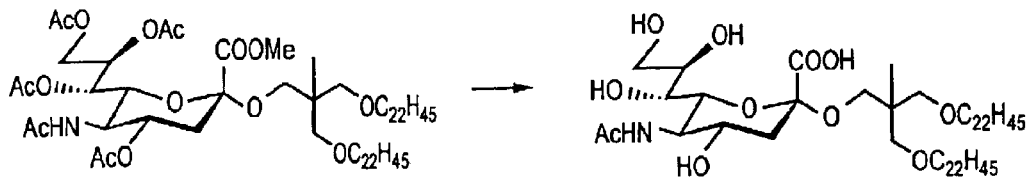
Figure 7:
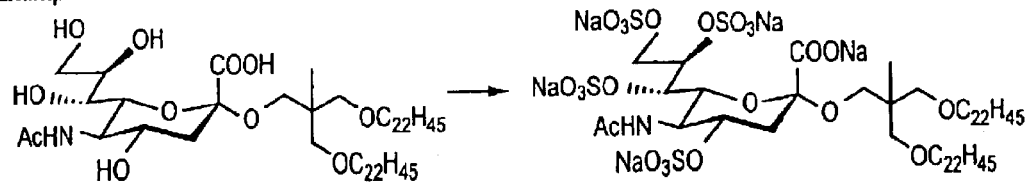
Figure 8:
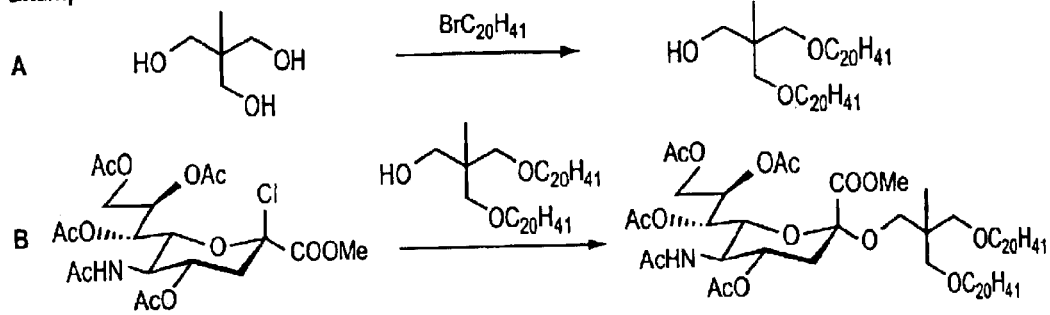
FIG. 8 is a diagram showing the reaction pathway from Examples 30 to 34.
Figure 8:
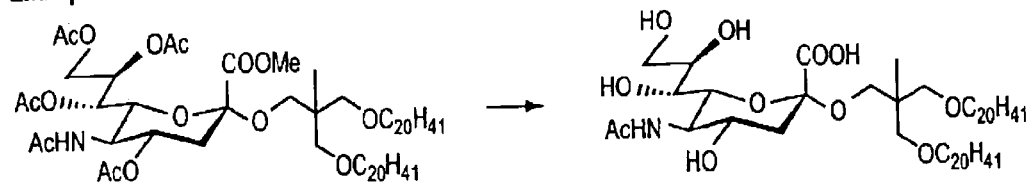
Figure 8:
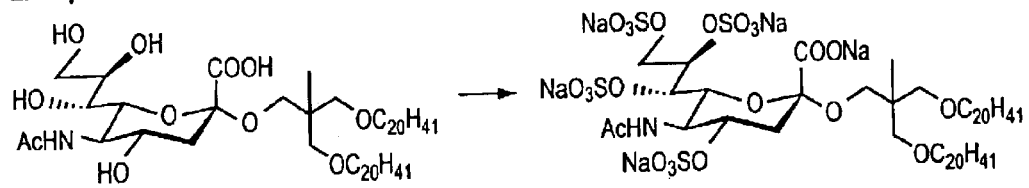
Figure 8:
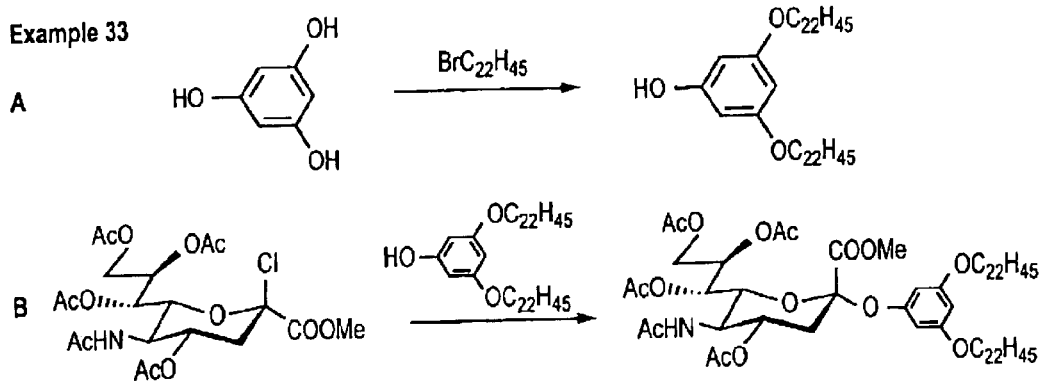
Figure 8:
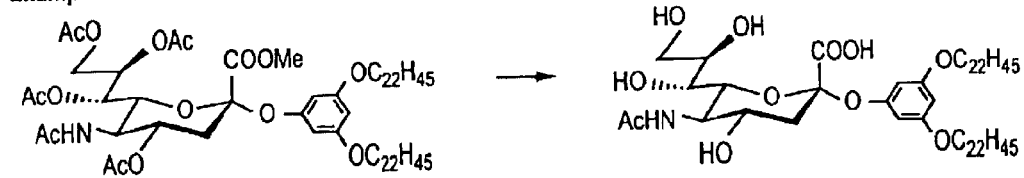
Figure 9:
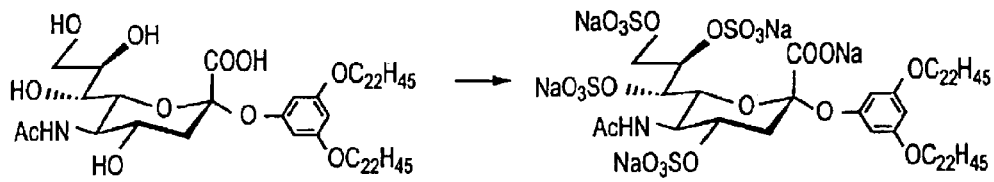
FIG. 9 is a diagram showing the reaction pathway from Examples 35 to 36.
Figure 9:
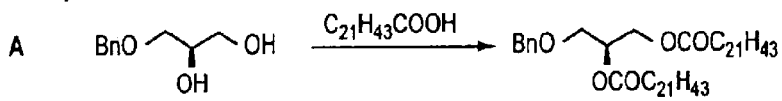
Figure 9:
Figure 9:
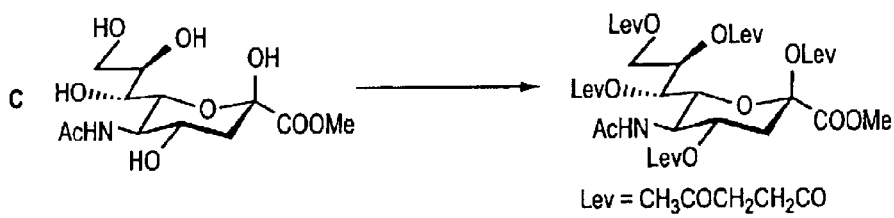
Figure 9:
Figure 9:
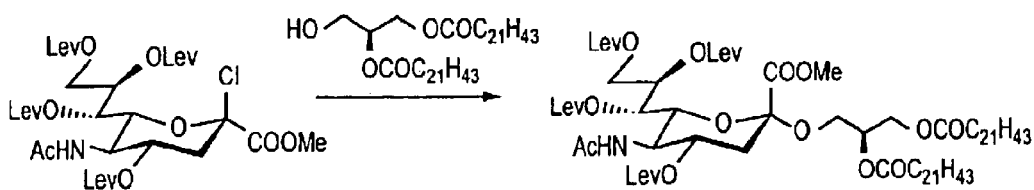
Figure 10:
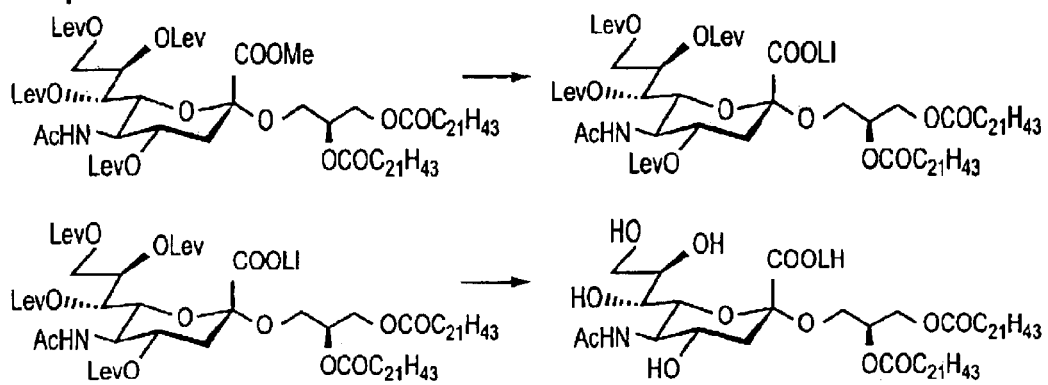
FIG. 10 is a diagram showing the reaction pathway from Examples 37 to 41.
Figure 10:
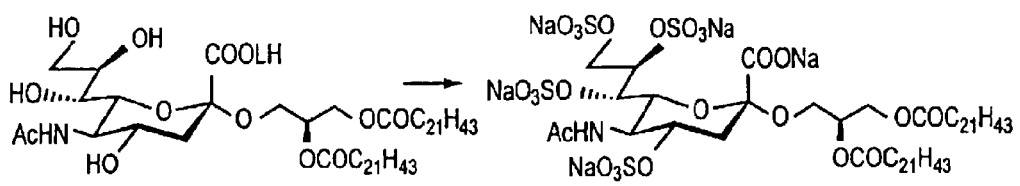
Figure 10:
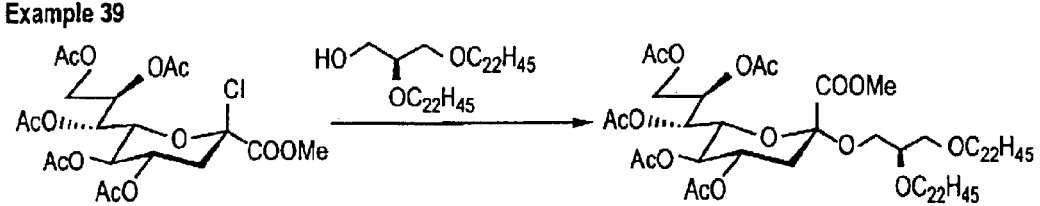
Figure 10:
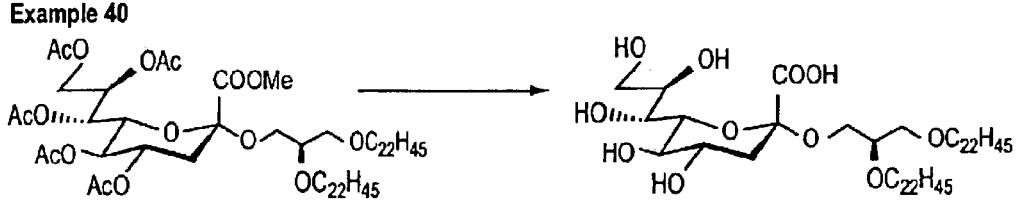
Figure 10:
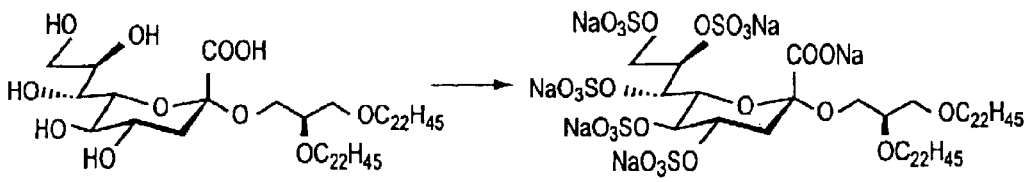
Figure 11:
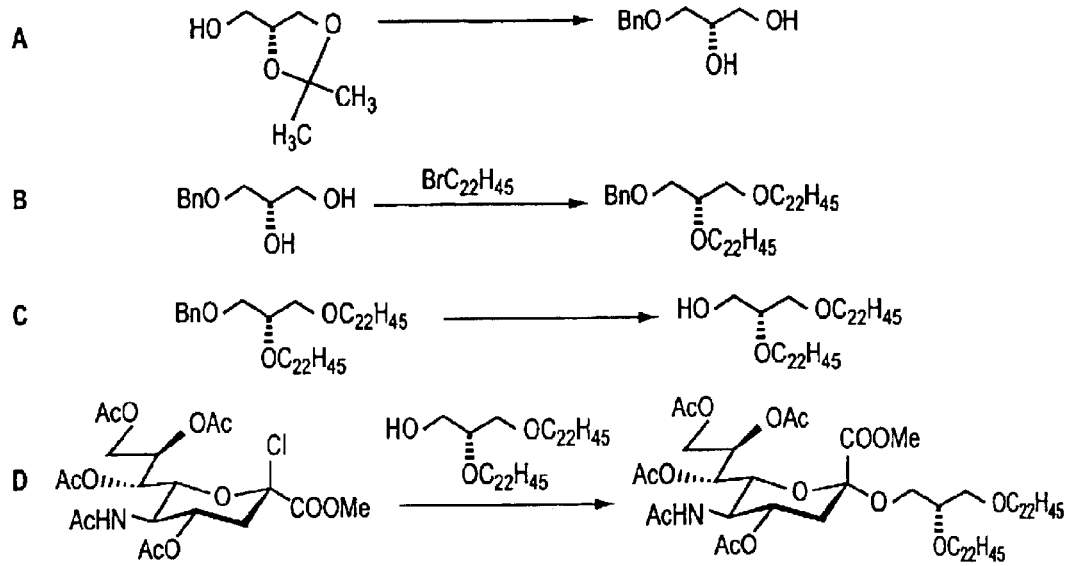
FIG. 11 is a diagram showing the reaction pathway from Examples 42 to 45.
Figure 11:
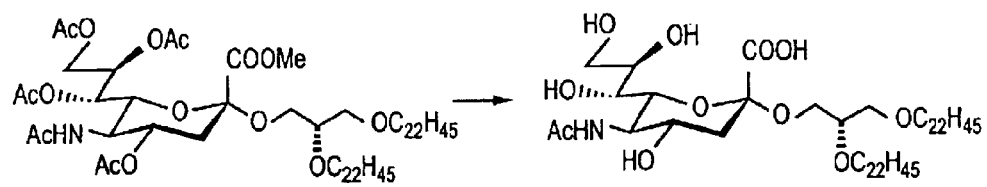
Figure 11:
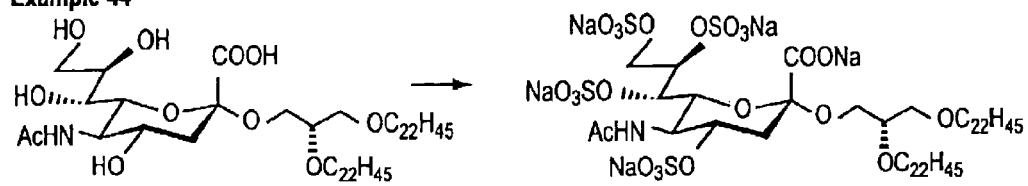
Figure 11:
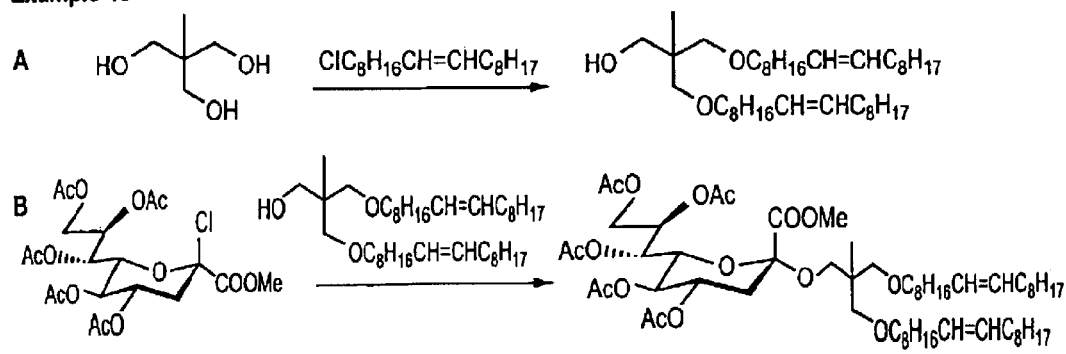
Figure 12:
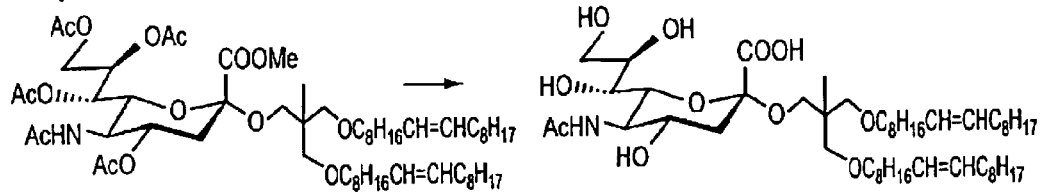
FIG. 12 is a diagram showing the reaction pathway from Examples 46 to 51.
Figure 12:
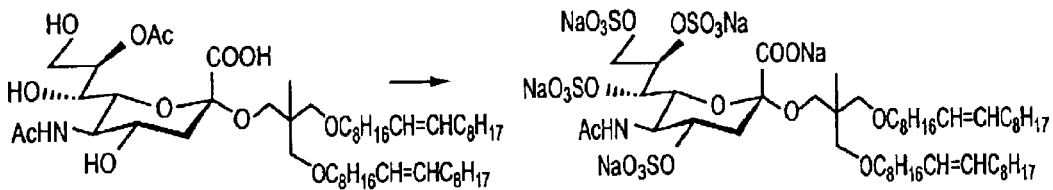
Figure 12:
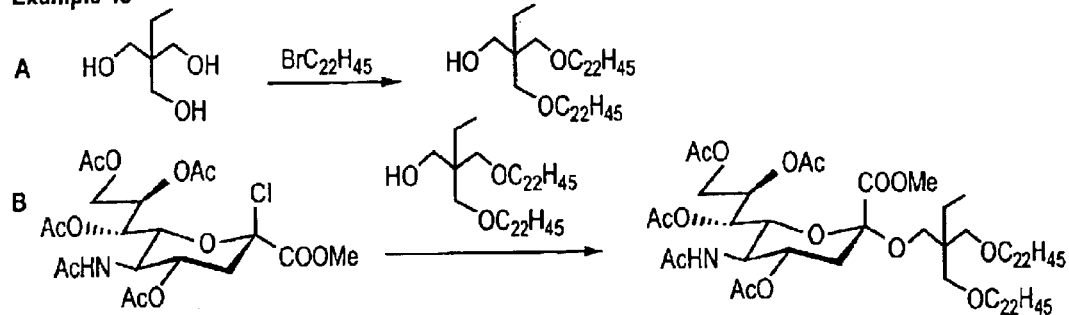
Figure 12:
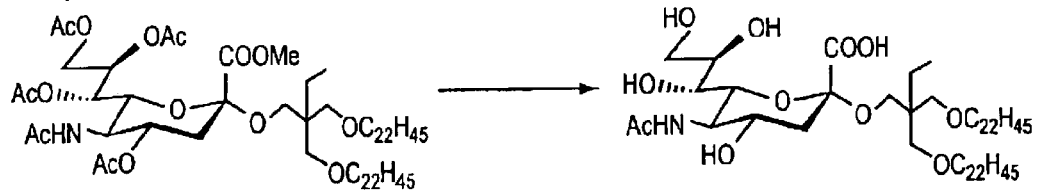
Figure 12:
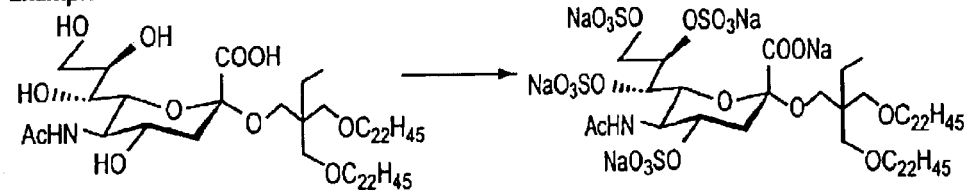
Figure 12:
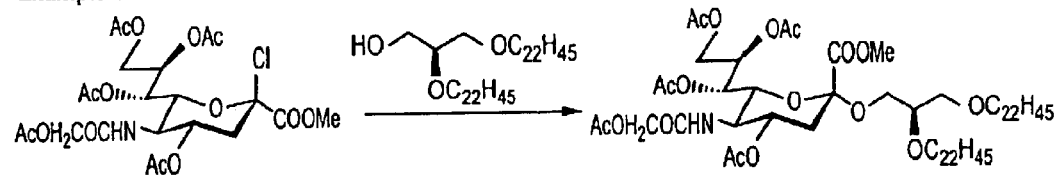
Figure 13:
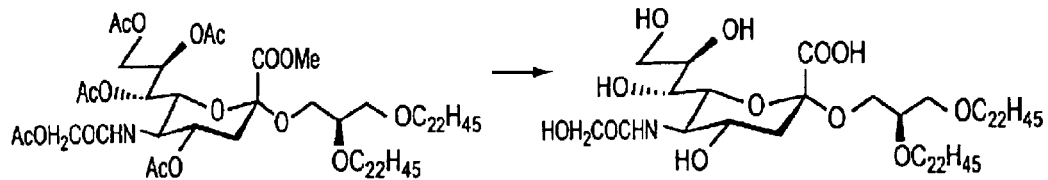
FIG. 13 is a diagram showing the reaction pathway from Examples 52 to 56.
Figure 13:
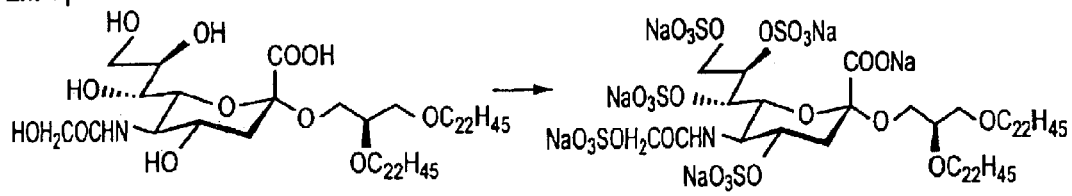
Figure 13:
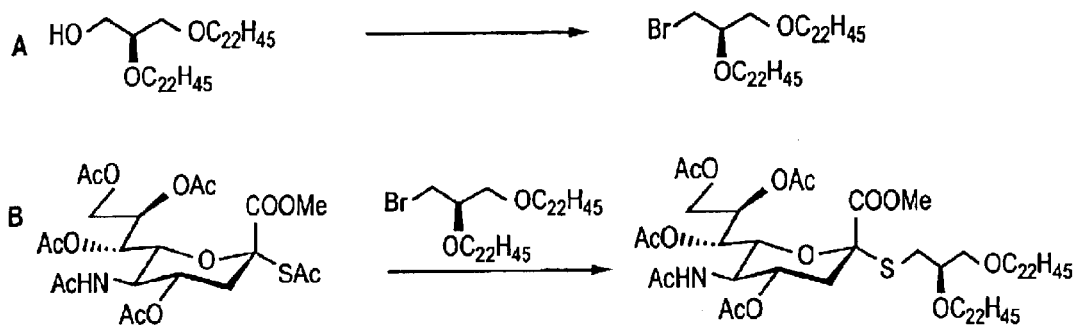
Figure 13:
Figure 13:
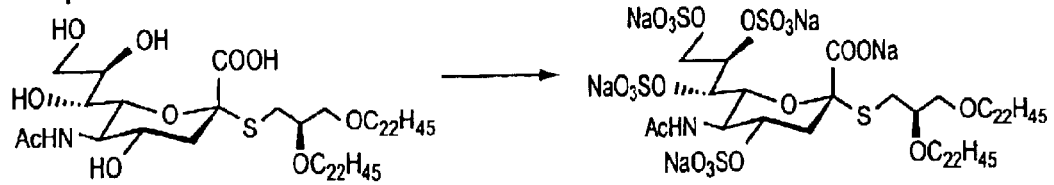
Figure 14:
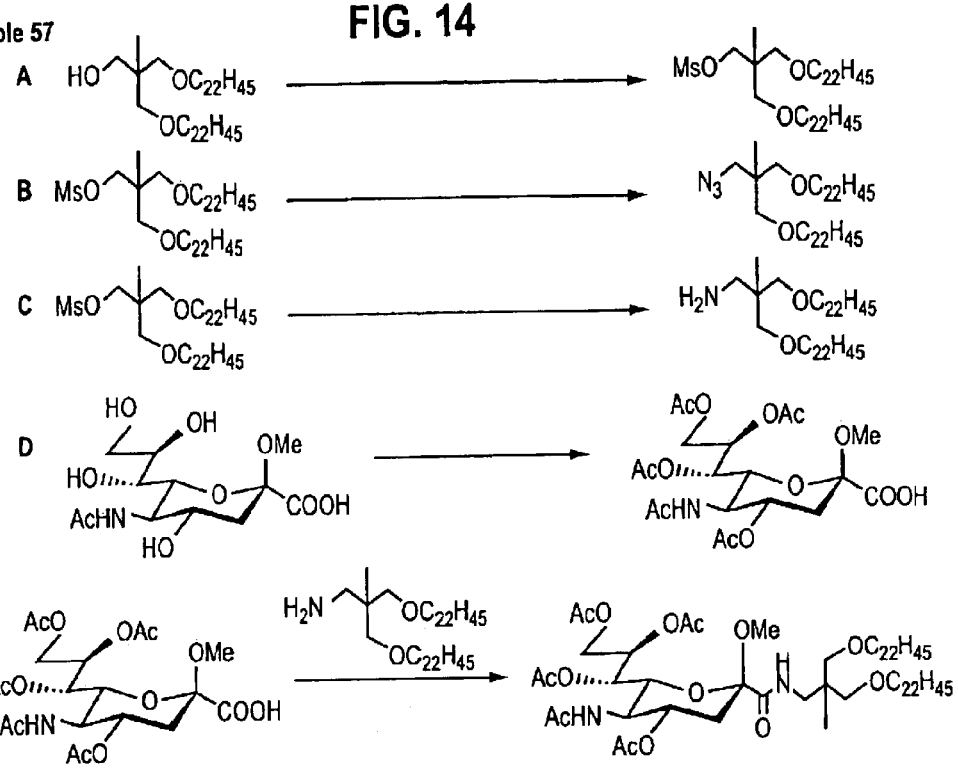
FIG. 14 is a diagram showing the reaction pathway from Examples 57 to 60B.
Figure 14:
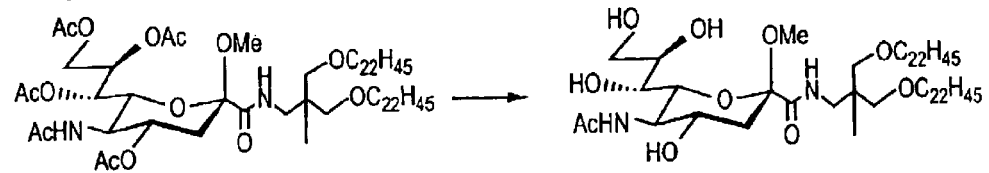
Figure 14:
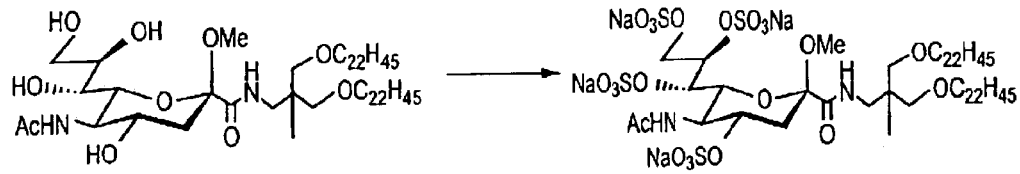
Figure 14:
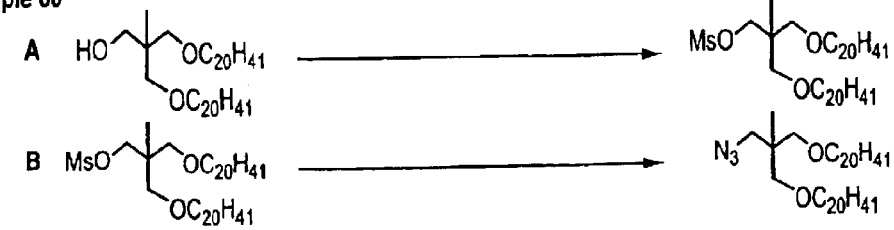
Figure 15:
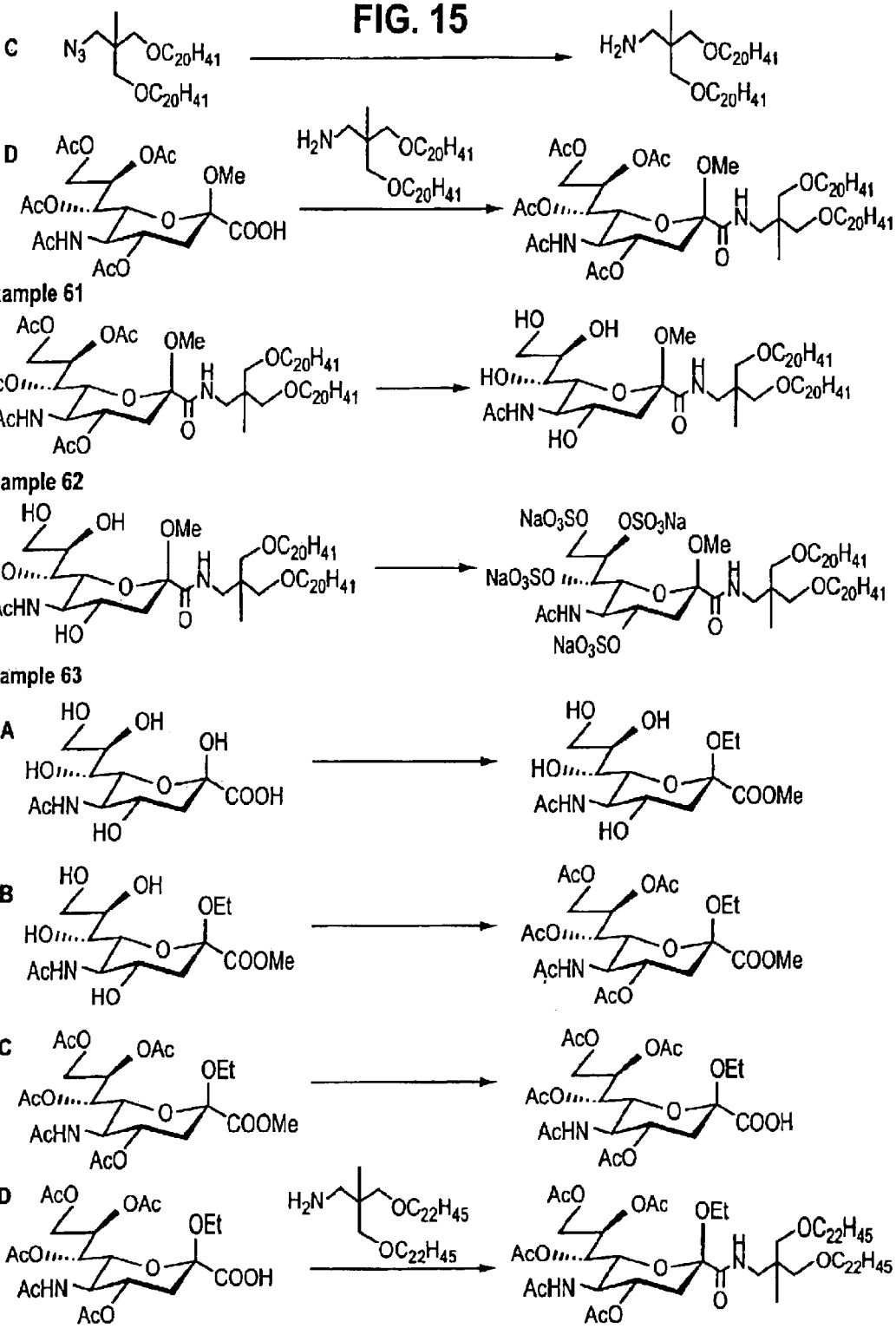
FIG. 15 is a diagram showing the reaction pathway from Examples 60C to 63.
Figure 16:
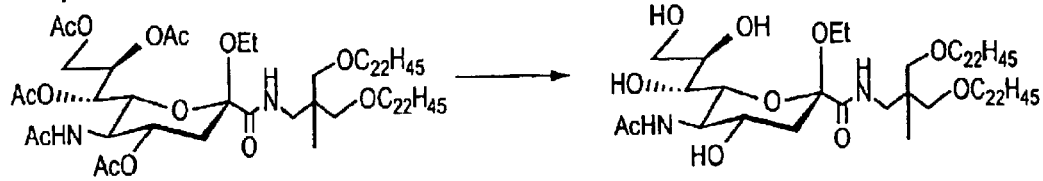
FIG. 16 is a diagram showing the reaction pathway from Examples 64 to 68.
Figure 16:
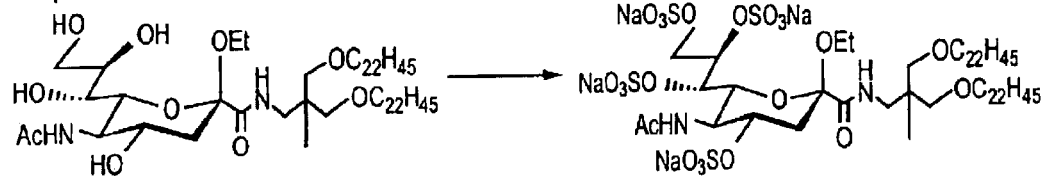
Figure 16:
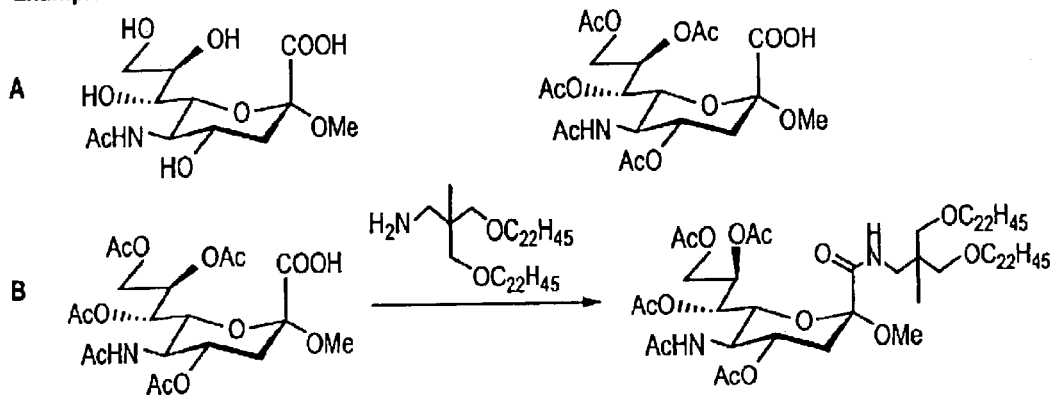
Figure 16:
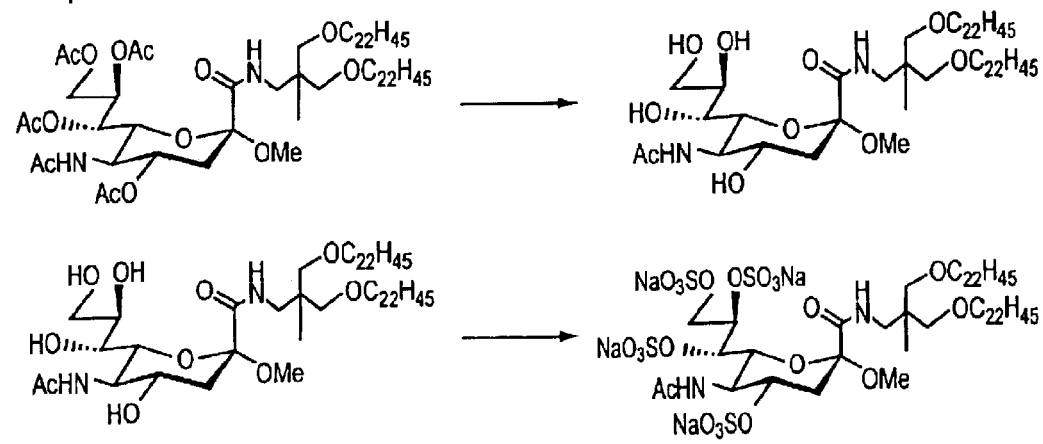
Figure 16:
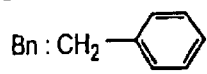

Sodium[methyl 5-acetamido-3,5-dideoxy-4,7,8,9-tetra-O-(sodium oxysulfonyl)-D-glycero-α-D-galacto-2-nonulopyranosid]onate Methyl 5-acetamido-3,5-dideoxy-D-glycero-α-D-galacto-2-nonulopyranosidonate [Chem. Ber., 99, 611 (1966)] (200 mg, 0.58 mmol) and sulfur trioxide-trimethylamine complex (1600 mg, 11.5 mmol) were stirred in anhydrous dimethylformamide (5.8 ml) under the argon atmosphere at 80–85° C. for 2 h. The reaction mixture was purified directly by silica gel column chromatography (gel 209 g, chloroform/methanol/water, 5:4:1), and further treated with Dowex 50W-X8 (Na form) resin. The product was further purified by gel chromatography (Sephadex G-25, 400 ml, water) to obtain the title compound (359 mg, 82%) as white solid.

$^1$H-NMR ($D_2O$) δ: 3.37 (s, 3H, $OCH_3$), 2.88 (dd, 1H, J=4.0, 11.7 Hz, H-3eq), 1.97 (s, 3H, NAc), 1.77 (t, 1H, J=12.1 Hz, H-3ax).

Example 2

Sodium[methyl 5-acetamido-3,5-dideoxy4,7,8,9-tetra-O-(sodium oxysulfonyl)-D-glycero-β-D-galacto-2-nonulopyranosid]onate Methyl 5-acetamido-3,5-dideoxy-D-glycero-β-D-galacto-2-nonulopyranosidonate [Chem. Ber., 99, 611

(1966)] (200 mg) was reacted by the general procedure according to Example 1 to obtain the title compound (218 mg, 50%) as white solid.

$^1$H-NMR (D$_2$O) δ: 3.33 (s, 3H, OCH$_3$), 2.57 (dd, 1H, J=5.1, 13.2 Hz, H-3eq), 1.96 (s, 3H, NAc), 1.90 (t, 1H, J=13.2 Hz, H-3ax).

Example 3

3-O-[Sodium{5-acetamido-3,5-dideoxy-4,7,8,9-tetra-O-(sodium oxysulfonyl)-D-glycero-α-D-galacto-2-nonulopyranosyl}onate]-1,2-di-O-hexyl-Sn-glycerol 3-O-[Sodium(5-acetamido-3,5-dideoxy-D-glycero-α-D-galacto-2-nonulopyranosyl)onate]-1,2-di-O-hexyl-Sn-glycerol [Japanese Patent Laid-Open Publication No. Hei1-125394] (19 mg) was reacted by the general procedure according to Example 1 to obtain the title compound (15 mg, 46%) as white solid.

$^1$H-NMR (CD$_3$OD) δ: 3.02 (dd, 1H, J=4.9, 12.6 Hz, H-3eq), 1.92 (s, 3H, NAc), 1.83 (t, 1H, J=12.1 Hz, H-3ax), 1.39–1.26 (m, 12H, 6CH$_2$), 0.90 (t, 6H, J=6.6 Hz, 2CH$_2$CH$_3$).

Example 4

3-O-[Sodium{5-acetamido-3,5-dideoxy-4,7,8,9-tetra-O-(sodium oxysulfonyl)-D-glycero-β-D-galacto-2-nonulopyranosyl}onate]-1,2-di-O-hexyl-Sn-glycerol 3-O-[Sodium(5-acetamido-3,5-dideoxy-D-glycero-β-D-galacto-2-nonulopyranosyl)onate]-1,2-di-O-hexyl-Sn-glycerol [Japanese Patent Laid-Open Publication No. Hei1-125394] (26 mg) was reacted by the general procedure according to Example 1 to obtain the title compound (22 mg, 48%) as white solid.

$^1$H-NMR (CD$_3$OD) δ: 2.83 (dd, 1H, J=5.1, 12.8 Hz, H-3eq), 2.03 (s, 3H, NAc), 1.87 (t, 1H, J=12.3 Hz, H-3ax), 1.37–1.34 (m, 12H, 6CH$_2$), 0.90 (t, 3H, J=6.8 Hz, CH$_2$CH$_3$), 0.90 (t, 3H, J=7.0 Hz, CH$_2$CH$_3$).

Example 5

3-O-[Sodium{5-acetamido-3,5-dideoxy-4,7,8,9-tetra-O-(sodium oxysulfonyl)-D-glycero-α-D-galacto-2-nonulopyranosyl}onate]-1,2-di-O-decyl-Sn-glycerol 3-O-[Sodium(5-acetamido-3,5-dideoxy-D-glycero-α-D-galacto-2-nonulopyranosyl)onate]-1,2-di-O-decyl-Sn-glycerol [Japanese Patent Laid-Open Publication No. Hei1-125394] (190 mg) was reacted by the general procedure according to Example 1 to obtain the title compound (268 mg, 88%) as white solid.

$^1$H-NMR (D$_2$O) δ: 2.94 (dd, 1H, J=5.0, 13.0 Hz, H-3eq), 1.99 (s, 3H, NAc), 1.96 (t, 1H, J=12.5 Hz, H-3ax), 1.44–1.21 (m, 28H, 14CH$_2$), 0.89 (t, 6H, J=6.8 Hz, 2CH$_2$CH$_3$).

Example 6

3-O-[Sodium{5-acetamido-3,5-dideoxy4,7,8,9-tetra-O-(sodium oxysulfonyl)-D-glycero-β-D-galacto-2-nonulopyranosyl}onate]-1,2-di-O-decyl-Sn-glycerol 3-O-[Sodium(5-acetamido-3,5-dideoxy-D-glycero-β-D-galacto-2-nonulopyranosyl)onate]-1,2-di-O-decyl-Sn-glycerol [Japanese Patent Laid-Open Publication No. Hei1-125394] (197 mg) was reacted by the general procedure according to Example 1 to obtain the title compound (240 mg, 76%) as white solid.

$^1$H-NMR (D$_2$O) δ: 2.67 (dd, 1H, J=5.0, 13.0 Hz, H-3eq), 2.01 (s, 3H, NAc), 1.93 (t, 1H, J=12.2 Hz, H-3ax), 1.42–1.20 (m, 28H, 14CH$_2$), 0.88 (t, 6H, J=6.8 Hz, 2CH$_2$CH$_3$).

Example 7

3-O-[Sodium{5-acetamido-3,5-dideoxy-4,7,8,9-tetra-O-(sodium oxysulfonyl)-D-glycero-α-D-galacto-2-nonulopyranosyl}onate]-1,2-di-O-tetradecyl-Sn-glycerol 3-O-[Sodium(5-acetamido-3,5-dideoxy-D-glycero-α-D-galacto-2-nonulopyranosyl)onate]-1,2-di-O-tetradecyl-Sn-glycerol [Japanese Patent Laid-Open Publication No. Sho59-164798] (406 mg) was reacted by the general procedure according to Example 1 to obtain the title compound (479 mg, 78%) as white solid.

$^1$H-NMR (CD$_3$OD) δ: 3.01 (dd, 1H, J=4.9, 11.9 Hz, H-3eq), 1.93 (s, 3H, NAc), 1.74 (t, 1H, J=12.1 Hz, H-3ax), 1.38–1.25 (m, 44H, 22CH$_2$), 0.90 (t, 6H, J=6.8 Hz, 2CH$_2$CH$_3$).

Example 8

3-O-[Sodium{5-acetamido-3,5-dideoxy-4,7,8,9-tetra-O-(sodium oxysulfonyl)-D-glycerol-β-D-galacto-2-nonulopyranosyl}ornate]-1,2-di-O-tetradecyl-Sn-glycerol 3-O-[Sodium(5-acetamido-3,5-dideoxy-D-glycero-βα-D-galacto-2-nonulopyranosyl)ornate]-1,2-di-O-tetradecyl-Sn-glycerol [Japanese Patent Laid-Open Publication No. Sho59-164798] (87 mg) was reacted by the general procedure according to Example 1 to obtain the title compound (120 mg, 91%) as white solid.

$^1$H-MR (CD$_3$OD) δ: 2.83 (DD, 1H, J=5.5, 12.8 Hz, H-3eq), 2.03 (s, 3H, ANC), 1.85 (t, 1H, J=12.0 Hz, H-ax), 1.45–1.20 (m, 44H, 22CH2), 0.90 (t, 6H, J=7.0 Hz, 2CH2CH3).

Example 9

3-O-[Sodium{5-acetamido-3,5-dideoxy-4,7,8,9-tetra-O-(sodium oxysulfonyl)-D-glycerol-α-D-galacto-2-nonulopyranosyl)onate]-1,2-di-O-octadecyl-Sn-glycerol 3-O-[Sodium(5-acetamido-3,5-dideoxy-D-glycero-α-D-galacto-2-nonulopyranosyl)onate]-1,2-di-O-octadecyl-Sn-glycerol [Japanese Patent Laid-Open Publication No. Hei1-125394] (45 mg) was reacted by the general procedure according to Example 1 to obtain the title compound (44 mg, 66%) as white solid.

$^1$H-NMR (CD$_3$OD) δ: 3.02 (dd, 1H, J=5.1, 13.2 Hz, H-3eq), 1.92 (s, 3H, NAc), 1.82 (t, 1H, J=12.5 Hz, H-3ax), 1.38–1.22 (m, 60H, 30CH$_2$), 0.90 (t, 6H, J=6.9 Hz, 2CH$_2$CH$_3$).

Example 10

3-O-[Sodium{5-acetamido-3,5-dideoxy-4,7,8,9-tetra-O-(sodium oxysulfonyl)-D-glycero-α-D-galacto-2-nonulopyranosyl}onate]-2-O-(sodium oxysulfonyl)-1-O-octadecyl-Sn-glycerol 3-O-[Sodium(5-acetamido-3,5-dideoxy-D-glycero-α-D-galacto-2-nonulopyranosyl)onate]-1-O-octadecyl-Sn-glycerol [Japanese Patent Publication No. Hei1-125394] (132 mg) was reacted by the general procedure according to Example 1 to obtain the title compound (125 mg, 53%) as white solid.

$^1$H-NMR (CD$_3$OD) δ: 3.07 (dd, 1H, J=5.1, 12.1 Hz, H-3eq), 1.95 (s, 3H, NAc), 1.68 (t, 1H, J=12.1 Hz, H-3ax), 1.36–1.22 (m, 30H, 15CH$_2$), 0.90 (t, 3H, J=7.0 Hz, CH$_2$CH$_3$).

Example 11

3-O-[Sodium{5-acetamido-3,5-dideoxy4,7,8,9-tetra-O-(sodium oxysulfonyl)-D-glycero-β-D-galacto-2-nonulopyranosyl}onate]-2-O-(sodium oxysulfonyl)-1-O-octadecyl-Sn-glycerol 3-O-[Sodium(5-acetamido-3,5-dideoxy-D-glycero-β-D-galacto-2-nonulopyranosyl)onate]-1-O-octadecyl-Sn-glycerol [Japanese Patent Publication No. Hei1-125394] (66 mg) was reacted by the general procedure according to Example 1 to obtain the title compound (31 mg, 49%) as white solid.

¹H-NMR (CD₃OD) δ: 2.81 (dd, 1H, J=4.4, 12.1 Hz, H-3eq), 2.03 (s, 3H, NAc), 1.88 (t, 1H, J=11.9 Hz, H-3ax), 1.38–1.17 (m, 30H, 15CH₂), 0.90 (t, 3H, J=7.0 Hz, CH₂CH₃).

Example 12

3-O-[Sodium{5-acetamido-3,5-dideoxy-4,7,8,9-tetra-O-(sodium oxysulfonyl)-D-glycero-α-D-galacto-2-nonulopyranosyl}onate]-1,2-di-O-docosyl-Sn-glycerol 3-O-[Sodium(5-acetamido-3,5-dideoxy-D-glycero-α-D-galacto-2-nonulopyranosyl)onate]-1,2-di-O-docosyl-Sn-glycerol [Japanese Patent Publication No. Hei1-125394] (502 mg) was reacted by the general procedure according to Example 1 to obtain the title compound (447 mg, 54%) as white solid.

¹H-NMR (CD₃OD-D₂O, 1:1, 50° C.) δ: 2.96 (br. dd, 1H, H-3eq), 1.97 (s, 3H, NAc), 1.83 (br. t, 1H, H-3ax), 1.40–1.21 (m, 76H, 38CH₂), 0.89 (t, 6H, J=6.4 Hz, 2CH₂CH₃).

Example 13

3-O-[Sodium{5-acetamido-3,5-dideoxy-4,7,8,9-tetra-O-(sodium oxysulfonyl)-D-glycero-β-D-galacto-2-nonulopyranosyl}onate]-1,2-di-O-docosyl-Sn-glycerol 3-O-[Sodium(5-acetamido-3,5-dideoxy-D-glycero-β-D-galacto-2-nonulopyranosyl)onate]-1,2-di-O-docosyl-Sn-glycerol [Japanese Patent Publication No. Hei1-125394] (44 mg) was reacted by the general procedure according to Example 1 to obtain the title compound (25 mg, 40%) as white solid.

¹H-NMR (CDCl₃-CD₃OD-D₂O, 3:4:2) δ: 2.75 (br. dd, 1H, H-3eq), 2.02 (s, 3H, NAc), 1.89 (br. t, 1H, H-3ax), 1.40–1.18 (m, 76H, 38CH₂), 0.89 (t, 6H, J=6.6 Hz, 2CH₂CH₃).

Example 14

3-S-[Sodium{5-acetamido-3,5-dideoxy-4,7,8,9-tetra-O-(sodium oxysulfonyl)-D-glycero-α-D-galacto-2-nonulopyranosyl}onate]-1,2-di-O-tetradecyl-Sn-thioglycerol 3-S-[Sodium(5-acetamido-3,5-dideoxy-D-glycero-α-D-galacto-2-nonulopyranosyl)onate]-1,2-di-O-tetradecyl-Sn-thioglycerol [Japanese Patent Laid-Open Publication No. Sho64-52794] (41 mg) was reacted by the general procedure according to Example 1 to obtain the title compound (47 mg, 77%) as white solid.

¹H-NMR (CD₃OD) δ: 3.17 (dd, 1H, J=5.1, 12.1 Hz, H-3eq), 1.92 (s, 3H, NAc), 1.77 (t, 1H, J=11.7 Hz, H-3ax), 1.41–1.23 (m, 44H, 22CH₂), 0.90 (t, 6H, J=7.1 Hz, 2CH₂CH₃).

Example 15

3-O-[Methyl(5-acetamido-4,7,8,9-tetra-O-acetyl-3,5-dideoxy-D-glycero-α-D-galacto-2-nonulopyranosyl)onate]-1,2-di-O-eicosyl-Sn-glycerol A 3-O-benzyl-1,2-di-O-eicosyl-Sn-glycerol 3-O-Benzyl-Sn-glycerol [Agric. Biol. Chem., 46, 255 (1982)] (300 mg, 1.65 mmol), 1-bromo-eicosane (2.38 g, 6.58 mmol) and pulverized sodium hydroxide (293 mg, 7.33 mmol) were azeotropically heated at reflux in benzene (10 ml) for 2 days to remove water from the mixture. After the reaction solution was diluted with ether and washed with water, the organic layer was dried over anhydrous magnesium sulfate and then condensed in vacuo. The residue was purified by silica gel column chromatography (100 g of gel, hexane:toluene=3:2) to obtain the title compound (929 mg, 76%) as white powder.

¹H-NMR (CDCl₃) δ: 7.34–7.26 (m, 5H, C₆H₅), 4.55 (s, 2H, CH₂Ph), 1.25 (m, 68H, 34H₂), 0.88 (t, 6H, J=6.6 Hz, 2CH₂CH₃).

B 1,2-Di-O-eicosyl-Sn-glycerol

3-O-benzyl-1,2-di-O-eicosyl-Sn-glycerol (1.47 g, 1.98 mmol) and 10% palladium-charcoal (200 mg). were stirred in ethyl acetate (30 ml) under the hydrogen atmosphere at room temperature for 18 h. The reaction mixture was filtered through celite, and the filtrate was concentrated in vacuo to obtain the title compound (934 mg, 72%) as white powder.

¹H-NMR (CDCl₃) δ: 1.25 (m, 68H, 34CH₂), 0.88 (t, 6H, J=6.6 Hz, 2CH₂CH₃).

C 3-O-[Methyl(5-acetamido-4,7,8,9-tetra-O-acetyl-3,5-dideoxy-D-glycero-α-D-galacto-2-nonulopyranosyl)onate]-1,2-di-O-eisosyl-Sn-glycerol A mixture comprising 1,2-di-O-eicosyl-Sn-glycerol (497 mg, 0.76 mmol), methyl 5-acetamido-4,7,8,9-tetra-O-acetyl-2-chloro-2,3,5-trideoxy-D-glycero-β-D-galacto-2-nonulopyranosonate [Chem. Ber., 99, 611 (1966)] (422 mg, 0.83 mmol), mercury (II) cyanide (336 mg, 1.33 mmol), mercury (II) bromide (478 mg, 1.33 mmol) and dried molecular sieve 4A (1.0 g) in anhydrous chloroform (5.0 ml) was stirred under the nitrogen atmosphere at room temperature overnight. After the reaction mixture was filtered, the filtrate was concentrated in vacuo, and purified by intermediary pressure silica gel column chromatography (125 g of gel, toluene:ethyl acetate=3:2) to obtain the title compound (390 mg, 46%) as white power.

¹H-NMR (CDCl₃) δ: 3.79 (s, 3H, OCH₃), 2.60 (dd, 1H, J=4.8, 12.8 Hz, H-3eq.), 2.14, 2.13, 2.06, 2.04, 1.88 (5s, 15H, 5Ac), 1.98 (t, 1H, J=12.8 Hz, H-3ax.), 1.25 (m, 68H, 34CH₂), 0.88 (t, 6H, J=7.0 Hz, 2CH₂CH₃).

Example 16

3-O-[(5-Acetamido-3,5-dideoxy-D-glycero-α-D-galacto-nonulopyranosonic acid)-2-yl]-1,2-di-O-eicosyl-Sn-glycerol 3-O-[Methyl (5-acetamido-4,7,8,9-tetra-O-acetyl-3,5-dideoxy-D-glycero-α-D-galacto-2-nonulopyranosyl)onate]-1,2-di-O-eicosyl-Sn-glycerol (455 mg, 0.40 mmol) and sodium methoxide was stirred in a mixture (13 ml) of THF:methanol (1:1) overnight. To this reaction mixture was added 3N sodium hydroxide (380 μl), and the mixture was stirred at 60° C. for 1 h. After the reaction mixture was concentrated in vacua, the residue was dissolved in ethanol and water, and the solution was adjusted to pH 2 with formic acid. Precipitates were collected by filtration, washed successively with water, methanol and ether, and dried in vacua to obtain the title compound (365 mg, 96%)as white powder.

¹H-NMR (CDCl₃-CD₃OD, 1:1) δ: 2.79 (dd, 1H, J=3.9, 12.3 Hz, H-3eq.), 2.03 (s, 3H, NAc), 1.69 (t, 1H, J=11.5 Hz, H-3ax.), 1.43–1.20 (m, 68H, 34CH₂), 0.89 (t, 6H, J=7.0 Hz, 2CH₂CH₃).

Example 17

3-O-[Sodium{5-acetamido-3,5-dideoxy-4,7,8,9-tetra-O-(sodium oxysulfonyl)-D-glycero-α-D-galacto-2-nonulopyranosyl)onate]-1,2-di-O-eicosyl-Sn-glycerol 3-O-[(5-Acetamido-3,5-dideoxy-D-glycero-α-D-galacto-nonulopyranosonic acid)-2-yl]-1,2-di-O-eicosyl-Sn-glycerol (241 mg) was reacted by the general procedure according to Example 1 to obtain the title compound (236 mg, 67%) as white solid.

¹H-NMR (CD₃OD) δ: 3.02 (dd, 1H, J=4.4, 12.4 Hz, H-3eq.), 1.92 (s, 3H, NAc), 1.80 (t, 1H, J=11.0 Hz, H-3ax.), 1.44–1.13 (m, 68H, 34CH₂), 0.909 (t, 6H, J=6.8 Hz, 2CH₂CH₃).

Example 18

3-O-[Methyl(5-acetamido-4,7,8,9-tetra-O-acetyl-3,5-dideoxy-D-glycero-α-D-galacto-2-nonulopyranosyl}onate]-1,2-di-O-tetracosyl-Sn-glycerol A 3-O-Benzyl-1,2-di-O-tetracosyl-Sn-glycerol 3-O-Benzyl-Sn-glycerol [Agric. Biol. Chem., 46, 255 (1982)] and 1-bromo-tetracosane [J. Am. Chem. Soc., 115, 3840 (1993)] were reacted by the general procedure according to Example 1 to obtain the title compound (236 mg, 67%) as white solid.

$^1$H-NMR (CDCl$_3$) δ: 7.34–7.26 (m, 5H, C$_6$H$_5$), 4.55 (s, 2H, CH$_2$Ph), 1.25 (m, 84H, 42CH$_2$), 0.88 (t, 6H, J=6.6 Hz, 2CH$_2$CH$_3$).

B 1,2-Di-O-tetracosyl-Sn-glycerol

3-O-Benzyl-1,2-di-O-tetracosyl-Sn-glycerol (1.47 g) was reacted in a mixture (30 ml) of toluene-ethyl acetate (1:1) by the general procedure according to 15-B to obtain the title compound (0.80 g, 66%) as white solid.

$^1$H-NMR (CDCl$_3$) δ: 1.25 (m, 84H, 42CH$_2$), 0.88 (t, 6H, J=6.6 Hz, 2CH$_2$CH$_3$).

C 3-O-[Methyl(5-acetamido-4,7,8,9-tetra-O-acetyl-3,5-dideoxy-D-glycero-α-D-galacto-2-nonulopyranosyl}onate]-1,2-di-O-tetracosyl-Sn-glycerol 1,2-Di-O-tetracosyl-Sn-glycerol (497 mg, 0.76 mmol) and methyl 5-acetamido-4,7,8,9-tetra-O-acetyl-2-chloro-2,3,5-trideoxy-D-glycero-β-D-galacto-2-nonulopyranosonate [Chem. Ber., 99, 611 (1966)] (422 mg, 0.83 mmol) were reacted by the general procedure according to 15-C to obtain the title compound (224 mg, 14%) as white solid.

$^1$H-NMR (CDCl$_3$) δ: 3.79 (s, 3H, OCH$_3$), 2.60 (dd, 1H, J=4.8, 12.8 Hz, H-3eq), 2.14, 2.13, 2.04, 2.03, 1.88 (5s, 15H, 5Ac), 1.98 (t, 1H, J=12.8 Hz, H-3ax), 1.25 (m, 84H, 42CH$_2$), 0.88 (t, 6H, J=6.6 Hz, 2CH$_2$CH$_3$).

Example 19

3-O-[(5-Acetamido-3,5-dideoxy-D-glycero-α-D-galacto-nonulopyranosonic acid)-2-yl]-1,2-di-O-tetracosyl-Sn-glycerol 3-O-[Methyl(5-acetamido-4,7,8,9-tetra-O-acetyl-3,5-dideoxy-D-glycero-α-D-galacto-2-nonulopyranosyl}onate]-1,2-di-O-tetracosyl-Sn-glycerol (240 mg) was reacted by the general procedure according to Example 16 to obtain the title compound (160 mg, 79%) as white solid.

$^1$H-NMR (CDCl$_3$-CD$_3$OD, 1:1) δ: 2.81 (dd, 1H, J=3.7, 12.1 Hz, H-3eq), 2.03 (s, 3H, NAc), 1.66 (t, 1H, J=11.3 Hz, H-3ax), 1.38–1.16 (m, 84H, 42CH$_2$), 0.89 (t, 6H, J=6.8 Hz, 2CH$_2$CH$_3$).

Example 20

3-O-[Sodium{5-acetamido-3,5-dideoxy-4,7,8,9-tetra-O-(sodium oxysulfonyl)-D-glycero-α-D-galacto-2-nonulopyranosyl}onate]-1,2-di-O-tetracosyl-Sn-glycerol 3-O-[(5-Acetamido-3,5-dideoxy-D-glycero-α-D-galacto-nonulopyranosonic acid) reacted by the general procedure according to Example 1 to obtain the title compound (21 mg, 19%) as white solid.

$^1$H-NMR (CD$_3$OD-D$_2$O, 1:1, 50° C.) δ: 2.96 (br. dd, 1H, H-3eq), 2.01 (s, 3H, NAc), 1.81 (br. t, 1H, H-3ax), 1.36–1.10 (m, 84H, 42CH$_2$), 0.89 (t, 6H, J=6.4 Hz, 2CH$_2$CH$_3$).

Example 21

3-O-[Methyl(5-acetamido-4,7,8,9-tetra-O-acetyl-3,5-dideoxy-D-glycero-α-D-galacto-2-nonulopyranosyl)onate]-1,2-di-O-hexacosyl-Sn-glycerol A 3-O-Benzyl-1,2-di-O-hexacosyl-Sn-glycerol 3-O-Benzyl-Sn-glycerol [Agric. Biol. Chem., 40, 391 (1976)] (242 mg) and 1-bromohexacosane [Agric. Biol. Chem., 46, 255 (1982)] (1.30 g) were reacted by the general procedure according to Example 15-A. Then, the compound thus obtained was, without purification, subjected to the debenzylation by the general procedure according to Example 15-B to obtain the title compound (615 mg, 57%) as white solid.

$^1$H-NMR (CDCl$_3$) δ: 1.25 (m, 92H, 46CH$_2$), 0.88 (t, 6H, J=6.6 Hz, 2CH$_2$CH$_3$).

B 3-O-[Methyl(5-acetamido-4,7,8,9-tetra-O-acetyl-3,5-dideoxy-D-glycero-α-D-galacto-2-nonulopyranosyl)onate]-1,2-di-O-hexacosyl-Sn-glycerol 1,2-Di-O-hexacosyl-Sn-glycerol (610 mg, 0.74 mmol) and methyl 5-acetamido-4,7,8,9-tetra-O-acetyl-2-chloro-2,3,5-trideoxy-D-glycero-β-D-galacto-2-nonulopyranosonate [Chem. Ber., 99, 611 (1966)] (454 mg, 0.89 mmol) were reacted by the general procedure according to Example 15-C to obtain the title compound (76 mg, 8%) as white solid.

$^1$H-NMR (CDCl$_3$) δ: 3.79 (s, 3H, OCH$_3$), 2.60 (dd, 1H, J=4.8, 12.8 Hz, H-3eq), 2.14, 2.13, 2.04, 2.02, 1.88 (5s, 15H, 5Ac), 1.97 (t, 1H, J=12.8 Hz, H-3ax), 1.25 (m, 92H, 46CH$_2$), 0.88 (t, 6H, J=7.0 Hz, 2CH$_2$CH$_3$).

Example 22

3-O-[(5-Acetamido-3,5-dideoxy-D-glycero-α-D-galacto-nonulopyranosonic acid)-2-yl]-1,2-di-O-hexacosyl-Sn-glycerol 3-O-[Methyl(5-acetamido4,7,8,9-tetra-O-acetyl-3,5-dideoxy-D-glycero-α-D-galacto-2-nonulopyranosyl)onate]-1,2-di-O-hexacosyl-Sn-glycerol (76 mg) was reacted by the general procedure according to Example 16 to obtain the title compound (51 mg, 78%) as white solid.

$^1$H-NMR (CDCl$_3$-CD$_3$OD, 1:1, 60° C.) δ: 2.76 (dd, 1H, J=4.4, 12.8 Hz, H-3eq), 2.02 (s, 3H, NAc), 1.75 (t, 1H, J=11.7 Hz, H-3ax), 1.42–1.14 (m, 92H, 46CH$_2$), 0.89 (t, 6H, J=6.8 Hz, 2CH$_2$CH$_3$).

Example 23

3-O-[Sodium{5-acetamido-3,5-dideoxy-4,7,8,9-tetra-O-(sodium oxysulfonyl)-D-glycero-α-D-galacto-2-nonulopyranosyl}onate]-1,2-di-O-hexacosyl-Sn-glycerol 3-O-[(5-Acetamido-3,5-dideoxy-D-glycero-α-D-galacto-nonulopyranosonic acid)-2-yl]-1,2-di-O-hexacosyl-Sn-glycerol (47 mg) was reacted by the general procedure according to Example 1 to obtain the title compound (29 mg, 45%) as white solid.

$^1$H-NMR (CD$_3$OD-D$_2$O, 1:1, 60° C.) δ: 2.96 (br. dd, 1H, H-3eq), 1.96 (s, 3H, NAc), 1.79 (br. t, 1H, H-3ax), 1.42–1.14 (m, 92H, 46CH$_2$), 0.88 (br. t, 6H, J=6.2 Hz, 2CH$_2$CH$_3$).

Example 24

3β-[Sodium{5-acetamido-3,5-dideoxy-4,7,8,9-tetra-O-(sodium oxysulfonyl)-D-glycero-α-D-galacto-2-nonulopyranosyl}onate]-5-cholestene 3β-[(5-Acetamido-3,5-dideoxy-D-glycero-α-D-galacto-2-nonulopyranosonic acid)-2-yl]-5-cholestene [Japanese Patent Laid-Open Publication No. Sho 61-243096] (387 mg) was reacted by the general procedure according to Example 1 to obtain the title compound (232 mg, 37%) as white solid.

$^1$H-NMR (CD$_3$OD-D$_2$O, 1:1) δ: 2.92 (dd, 1H, J=4.5, 11.5 Hz, H-3eq), 1.96 (s, 3H, NAc), 0.99 (s, 3H, CH$_3$-19 chole), 0.68 (s, 3H, CH$_3$-18 chole).

Example 25

Sodium[oleyl 5-acetamido-3,5-dideoxy-4,7,8,9-tetra-O-(sodium oxysulfonyl)-D-glycero-α-D-galacto-2-nonulopyranosid]onate A Sodium(oleyl 5-acetamido-3,5-dideoxy-D-glycero-α-D-galacto-2-nonulopyranosid)onate To a solution of methyl (oleyl 5-acetamido-4,7,8,9-tetra-O-acetyl-3,5-dideoxy-D-glycero-α-D-galacto-2-nonulopyranosid)onate [Japanese Patent Laid-Open Publication No. Sho 63-264493](115 mg, 0.154 mmol) dissolved in methanol (1.5 ml) was added 3N sodium hydroxide (0.30 ml), and the mixture was stirred at room temperature for 16 h. The reaction solution was evaporated to dryness in vacua, and the residue was purified by gel chromatography (Sephadex LH-20, 180 ml, methanol) to obtain the title compound (78 mg, 87%) as white solid.

$^1$H-NMR (CD$_3$OD) δ: 5.34 (m, 2H, CH=CH), 2.81 (dd, 1H, J=4.0, 12.1 Hz, H-3eq), 2.00 (s, 3H, NAc), 1.59 (t, 1H, J=11.7 Hz, H-3ax), 1.42–1.23 (m, 20H, 10CH$_2$), 0.90 (t, 3H, J=7.0 Hz, CH$_2$CH$_3$).

B Sodium[oleyl 5-acetamido-3,5-dideoxy-4,7,8,9-tetra-O-(sodium oxysulfonyl)-D-glycero-α-D-galacto-2-nonulopyranosid]onate Sodium(oleyl 5-acetamido-3,5-dideoxy-D-glycero-α-D-galacto-2-nonulopyranosid)onate (62 mg) was reacted by the general procedure according to Example 1 to obtain the title compound (86 mg, 82%) as white solid.

$^1$H-NMR (CD$_3$OD) δ: 3.03 (dd, 1H, J=3.7, 12.3 Hz, H-3eq), 2.19 (m, 4H, CH$_2$CH=CHCH$_2$), 1.92 (s, 3H, NAc), 1.73 (t, 1H, J=12.1 Hz, H-3ax), 1.42–1.22 (m, 20H, 10CH$_2$), 0.90 (t, 3H, J=6.8 Hz, CH$_2$CH$_3$).

Example 26

Sodium[octadecyl 5-acetamido-3,5-dideoxy-4,7,8,9-tetra-O-(sodium oxysulfonyl)-D-glycero-α-D-galacto-2-nonulopyranosid)onate A Methyl(octadecyl 5-acetamido-4,7,8,9-tetra-O-acetyl-3,5-dideoxy-D-glycero-α-D-galacto-2-nonulopyranosid)onate To a solution of methyl(oleyl 5-acetamido-4,7,8,9-tetra-O-acetyl-3,5-dideoxy-D-glycero-α-D-galacto-2-nonulopyranosid)onate [Japanese Patent Laid-Open Publication No. Sho 63-264493] (111 mg, 0.149 mmol) dissolved in ethanol (1.5 ml) was added 10% palladium-charcoal (16 mg) was added, and the mixture was stirred under the hydrogen atmosphere at room temperature for 18 h. The reaction solution was filtered through celite to obtain the title compound (107 mg, 96%) as white solid.

$^1$H-NMR (CDCl$_3$) δ: 3.79 (s, 3H, COOCH$_3$), 2.58 (dd, 1H, J=4.8, 12.8 Hz, H-3eq), 2.15, 2.14, 2.04, 2.03, 1.88 (5s, 15H, 5Ac), 1.95 (t, 1H, J=12.6 Hz, H-3ax), 1.38–1.19 (m, 30H, 15CH$_2$), 0.88 (t, 3H, J=7.0 Hz, CH$_2$CH$_3$).

B Sodium(octadecyl 5-acetamido-3,5-dideoxy-D-glycero-α-D-galacto-2-nonulopyranosid)onate Methyl(octadecyl 5-acetamido-4,7,8,9-tetra-O-acetyl-3,5-dideoxy-D-glycero-α-D-galacto-2-nonulopyranosid)onate (107 mg) was reacted by the general procedure according to Example 25-A to obtain the titled compound (70 mg, 83%) as white solid.

$^1$H-NMR (CD$_3$OD) δ: 2.81 (dd, 1H, J=3.8, 12.3 Hz, H-3eq), 2.00 (s, 3H, NAc), 1.59 (t, 1H, J=11.9 Hz, H-3ax), 1.38–1.22 (m, 30H, 15CH$_2$), 0.90 (t, 3H, J=6.8 Hz, CH$_2$CH$_3$).

C Sodium[octadecyl 5-acetamido-3,5-dideoxy-4,7,8,9-tetra-O-(sodium oxysulfonyl)-D-glycero-α-D-galacto-2-nonulopyranosid]onate Sodium(octadecyl 5-acetamido-3,5-dideoxy-D-glycero-α-D-galacto-2-nonulo-pyranosid)onate (72 mg) was reacted by the general procedure according to Example 1 to obtain the title compound (109 mg, 92%) as white solid.

$^1$H-NMR (CD$_3$OD) δ: 3.02 (dd, 1H, J=3.7, 11.4 Hz, H-3eq), 1.92 (s, 3H, NAc), 1.73 (t, 1H, J=11.7 Hz, H-3ax), 1.40–1.31 (m, 30H, 15CH$_2$), 0.90 (t, 3H, J=7.0 Hz, CH$_2$CH$_3$).

Example 27

Methyl[2,2-bis(docosyloxymethyl)propyl 5-acetamido-4,7,8,9-tetra-O-acetyl-3,5-dideoxy-D-glycero-α-D-galacto-2-nonulopyranosid]onate A 2,2-bis(docosyloxymethyl)propanol 1,1,1-tris(hydroxymethyl)ethane (1.0 g, 8.32 mmol) and sodium hydride (732 mg, 18.3 mmol) were stirred in dehydrated dimethylformamide (30 ml) at room temperature for 15 mm. Then, the reaction solution was cooled in ice, and docosyl bromide (7.1 g, 18.3 mmol) and benzene (10 ml) were added thereto, and the resulting mixture was stirred at room temperature for 16 h. The reaction solution was concentrated in vacuo, and the residue was suspended in chloroform, and washed with 2HCl. The organic layer was dried over anhydrous magnesium sulfate, and concentrated in vacuo. The residue was purified by silica gel column chromatography (130 g of gel, toluene/ethyl acetate, 19:1) to obtain the title compound (42.2 g, 38%) as white powder.

B Methyl[2,2-bis(docosyloxymethyl)propyl 5-acetamido-4,7,8,9-tetra-O-acetyl-3,5-dideoxy-D-glycero-α-D-galacto-2-nonulopyranosid]onate 2,2-Bis(docosyloxymethyl)propanol (1.20 g, 1.63 mmol) and methyl 5-acetamido-4,7,8,9-tetra-O-acetyl-2-chloro-2,3,5-trideoxy-D-glycero-β-D-galacto-2-nonulo pyranosonate [Chem. Ber., 99, 611 (1966)] (913 mg, 1.79 mmol) were reacted by the general procedure according to Example 15-C to obtain the title compound (786 mg, 40%) as white solid.

$^1$H-NMR (CDCl$_3$) δ: 3.78 (s, 3H, COOCH$_3$), 2.57 (dd, 1H, J=4.4, 12.8 Hz, H-3eq.), 2.13, 2.12, 2.04, 2.02, 1.88 (5s, 15H, 5Ac), 1.95 (t, 1H, J=12.5 Hz, H-3ax.), 1.25 (m, 76H, 38CH$_2$), 0.90 (s, 3H, CCH$_3$), 0.88 (t, 6H, J=7.0 Hz, 2CH$_2$CH$_3$).

Example 28

2,2-Bis(docosyloxymethyl)propyl 5-acetamido-3,5-dideoxy-D-glycero-α-D-galacto-2-nonulopyranosidonic acid:

Methyl[2,2-bis(docosyloxymethyl)propyl 5-acetamido-4,7,8,9-tetra-O-acetyl-3,5-dideoxy-D-glycero-α-D-galacto-2-nonulopyranosid]onate (786 mg) was reacted by the general procedure according to Example 16 to obtain the title compound (599 mg, 90%) as white solid.

$^1$H-NMR (CDCl$_3$-CD$_3$OD, 1:1, 60° C.) δ: 2.79 (dd, 1H, J=4.8, 12.8 Hz, H-3eq), 2.02 (s, 3H, NAc), 1.75 (t, 1H, J=11.9 Hz, H-3ax), 1.36–1.22 (m, 76H, 38CH$_2$), 0.92 (s, 3H, CCH$_3$), 0.89 (t, 6H, J=6.8 Hz, 2CH$_2$CH$_3$).

Example 29

Sodium[2,2-bis(docosyloxymethyl)propyl 5-acetamido-3,5-dideoxy-4,7,8,9-tetra-O-(sodium oxysulfonyl)-D-glycero-α-D-galacto-2-nonulopyranosid]onate 2,2-Bis(docosyloxymethyl)propyl 5-acetamido-3,5-dideoxy-D-glycero-α-D-galacto-2-nonulopyranosidonic acid (94 mg) was reacted by the general procedure according to Example 1 to obtain the title compound (63 mg, 47%) as white solid. (599 mg, 90%) as white solid.

$^1$H-NMR (CD$_3$OD-D$_2$O, 1:1, 60° C.) δ: 2.93 (br. dd, 1H, H-3eq), 1.96 (s, 3H, NAc), 1.80 (br. t, 1H, H-3ax), 1.43–1.16 (m, 76H, 38CH$_2$), 0.92 (s, 3H, CCH$_3$), 0.89 (t, 6H, J=6.6 Hz, 2CH$_2$CH$_3$).

Example 30

Methyl[2,2-bis(eicosyloxymethyl)propyl 5-acetamido-4,7,8,9-tetra-O-acetyl-3,5-dideoxy-D-glycero-α-D-galacto-2-nonulopyranosid]onate A 2,2-Bis(eicosyloxymethyl)propanol 1,1,1-tris(hydroxymethyl)ethane (0.50 g, 4.16 mmol) and eicosyl bromide (3.30 g, 9.15 mmol) were reacted by the general procedure according to Example 27-A to obtain the title compound (1.43 g, 51%) as white solid.

$^1$H-NMR (CDCl$_3$) δ: 3.57 (d, 2H, J=5.9 Hz, CH$_2$OH), 1.26 (m, 68H, 34CH$_2$), 0.88 (t, 6H, J=7.0 Hz, 2CH$_2$CH$_3$), 0.85 (s, 3H, CCH$_3$).

B Methyl[2,2-bis(eicosyloxymethyl)propyl 5-acetamido-4,7,8,9-tetra-O-acetyl-3,5-dideoxy-D-glycero-α-D-galacto-2-nonulopyranosid]onate 2,2-bis(eicosyloxymethyl)propanol (267 mg, 0.392 mmol) and methyl 5-acetamido-4,7,8,9-tetra-O-acetyl-2-chloro-2,3,5-trideoxy-D-glycero-β-D-galacto-2-nonulopyranosonate [Chem. Ber., 99, 611 (1966)] (200 mg, 0.392 mmol) were reacted by the general procedure according to Example 15-C to obtain the title compound (175 mg, 39%) as white solid.

$^1$H-NMR (CDCl$_3$) δ: 3.78 (s, 3H, COOCH$_3$), 2.58 (dd, 1H, J=4.8, 12.8 Hz, H-3eq.), 2.13, 2.13, 2.04, 2.02, 1.89 (5s, 15H, 5Ac), 1.95 (dd, 1H, J=12.5, 12.8 Hz, H-3ax.), 1.25 (m, 68H, 34CH$_2$), 0.90 (s, 3H, CCH$_3$), 0.88 (t, 6H, J=7.0 Hz, 2CH$_2$CH$_3$).

Example 31

2,2-bis(eicosyloxymethyl)propyl 5-acetamido-3,5-dideoxy-D-glycero-α-D-galacto-2-nonulopyranosidonic acid:

Methyl[2,2-bis(eicosyloxymethyl)propyl 5-acetamido-4,7,8,9-tetra-O-acetyl-3,5-dideoxy-D-glycero-α-D-galacto-2-nonulopyranosid]onate (174 mg) was reacted by the general procedure according to Example 16 to obtain the title compound (127 mg, 87%) as white solid.

$^1$H-NMR (CDCl$_3$-CD$_3$OD, 1:1) δ: 2.75 (dd, 1H, J=4.6, 12.6 Hz, H-3eq), 2.03 (s, 3H, NAc), 1.75 (t, 1H, J=11.7 Hz, H-3ax), 1.43–1.19 (m, 68H, 34CH$_2$), 0.92 (s, 3H, CCH$_3$), 0.89 (t, 6H, J=7.0 Hz, 2CH$_2$CH$_3$).

Example 32

Sodium[2,2-bis(eicosyloxymethyl)propyl 5-acetamido-3,5-dideoxy-4,7,8,9-tetra-O-(sodium oxysulfonyl)-D-glycero-α-D-galacto-2-nonulopyranosid)onate 2,2-bis(eicosyloxymethyl)propyl 5-acetamido-3,5-dideoxy-D-glycero-α-D-galacto-2-nonulopyranosidonic acid (103 mg) acid was reacted by the general procedure according to Example 1 to obtain the title compound (96 mg, 64%) as white solid.

$^1$H-NMR (CD$_3$OD-D$_2$O, 1:1, 60° C.) δ: 2.96 (br. dd, 1H, H-3eq), 1.98 (s, 3H, NAc), 1.78 (t, 1H, J=12.6 Hz, H-3ax), 1.37–1.17 (m, 68H, 34CH$_2$), 0.94 (s, 3H, CCH$_3$), 0.90 (t, 6H, J=6.8 Hz, 2CH$_2$CH$_3$).

Example 33

Methyl(3,5-didocosyloxyphenyl 5-acetamido-4,7,8,9-tetra-O-acetyl-3,5-dideoxy-D-glycero-α-D-galacto-2-nonulopyranosid)onate A 3,5-didocosyloxyphenol After phloroglucinol (2.0 g, 15.9 mmol) and sodium hydride (1.59 g, 39.7 mmol) were stirred in dehydrated dimethylformamide (30 ml) at room temperature for 15 min, docosyl bromide (13.0 mg, 33.3 mmol) and benzene (30 ml) were added thereto, and the resulting mixture was stirred at 40° C. for 2 days. The reaction solution was diluted with chloroform, washed with 2N hydrochloric acid, and the organic layer was dried over anhydrous magnesium sulfate. The solvent was concentrated in vacuo, and the residue was purified by silica gel column chromatography (90 g of the gel, hexane/ethyl acetate, 6:1) to obtain the title compound (2.40 g, 20%) as light yellow powder.

$^1$H-NMR (CDCl$_3$) δ: 6.06 (d, 1H, J=2.2 Hz, H-4 phenyl), 5.99 (2d, 2H, J=2.2 Hz, H-2,6 phenyl), 3.89 (t, 4H, J=6.8 Hz, 2OCH$_2$), 1.39–1.17 (m, 72H, 36CH$_2$), 0.88 (t, 6H, J=6.8 Hz, 2CH$_2$CH$_3$).

B Methyl(3,5-didocosyloxyphenyl 5-acetamido-4,7,8,9-tetra-O-acetyl-3,5-dideoxy-D-glycero-α-D-galacto-2-nonulopyranosid)onate 3,5-Didocosyloxyphenol (1.20 g, 1.61 mmol) and sodium hydride (77.5 g, 1.94 mmol) were stirred in dimethylformamide:benzene (1:1, 40 ml) at room temperature for 20 min. Then, to this mixture was added methyl 5-acetamido-4,7,8,9-tetra-O-acetyl-2-chloro-2,3,5-trideoxy-D-glycero-β-D-galacto-2-nonulopyranosonate [Chem. Ber., 99, 611 (1966)] (823 mg, 1.61 mmol), and the resulting mixture was stirred at room temperature for 3 h. After the reaction solution was diluted with chloroform, and washed with 2N-hydrochloric acid and, the organic layer was dried over anhydrous magnesium sulfate. The solvent was condensed in vacuo, and the residue was purified by silica gel column chromatography (90 g of the gel, toluene/ethyl acetate, 2:3) to obtain the title compound (386 mg, 20%) light yellow powder.

$^1$H-NMR (CDCl$_3$) δ: 6.28 (2d, 2H, J=1.8 Hz, H-2, 6phenyl), 6.22 (d, 1H, J=1.8 Hz, H-4phenyl), 3.78 (s, 3H, COOCH$_3$), 2.58 (dd, 1H, J=4.8, 12.8 Hz, H-3eq.), 2.14, 2.10, 2.03, 2.01, 1.90 (5s, 15H, 5Ac), 1.26 (m, 76H, 38CH$_2$), 0.88 (t, 6H, J=6.6 Hz, 2CH$_2$CH$_3$).

Example 34

3,5-Didocosyloxyphenyl 5-acetamido-3,5-dideoxy-D-glycero-α-D-galacto-2-nonulopyrasidonic acid:

Methyl(3,5-didocosyloxyphenyl 5-acetamido-4,7,8,9-tetra-O-acetyl-3,5-dideoxy-D-glycero-α-D-galacto-2-nonulopyranosid)onate (385 mg) was reacted by the general procedure according to Example 16 to obtain the title compound (163 mg, 50%) as light yellow solid.

$^1$H-NMR (CDCl$_3$-CD$_3$OD, 1:1, 60° C.) δ: 6.42 (2d, 2H, J=2.2 Hz, H-2,6phenyl), 6.20 (d, 1H, J=2.2 Hz, H-4phenyl), 2.86 (dd, 1H, J=4.2, 12.6 Hz, H-3eq), 2.02 (s, 3H, NAc), 1.95 (t, 1H, J=11.9 Hz, H-3ax), 1.40–1.23 (m, 72H, 36CH$_2$), 0.89 (t, 6H, J=7.0 Hz, 2CH$_2$CH$_3$).

Example 35

Sodium[3,5-Didocosyloxyphenyl-5-acetamido-3,5-dideoxy-4,7,8,9-tetra-O-(sodium oxysulfonyl)-D-glycero-β-D-galacto-2-nonulopyranosid)onate 3,5-Didocosyloxyphenyl 5-acetamido-3,5-dideoxy-D-glycero-α-D-galacto-2-nonulo yranosidonic acid (16 mg) was reacted by the general procedure according to Example 1 to obtain the title compound (11 mg, 47%) as white solid.

$^1$H-NMR (CD$_3$OD-D$_2$O, 1:1, 50° C.) δ: 6.42 (br. s, 2H, H-2,6phenyl), 6.17 (br. s, 1H, H-4phenyl), 2.93 (br. dd, 1H, H-3eq), 2.00 (s, 3H, NAc), 1.38–1.18 (m, 72H, 36CH$_2$), 0.90 (t, 6H, J=7.0 Hz, 2CH$_2$CH$_3$).

Example 36

3-O-[Methyl(5-acetamido-4,7,8,9-tetra-O-acetyl-3,5-dideoxy-D-glycero-α-D-galacto-2-nonulopyranosyl)onate]-1,2-di-O-docosanoyl-Sn-glycerol A 3-O-Benzyl-1,2-di-O-docosanoyl-Sn-glycerol 3-O-Benzyl-Sn-glycerol [Agric. Biol. Chem., 40, 391 (1976)] (0.67 g, 3.68 mmol), behenic acid (3.76 g, 11.04 mmol), dicyclohexylcarbodiimide (2.28 g, 11.04 mmol) and 4-dimethylaminopyridine (0.13 g, 1.06 mmol) were stirred in pyridine (37 ml)at room temperature for 22 h. The reaction solution was filtered, and evaporated to dryness in vacuo. The residue was purified by silica gel column chromatography (using 90 g of gel, hexane/ethyl acetate, 9:1) to obtain the title compound (1.55 g, 51%) as light yellow powder.

$^1$H-NMR (CDCl$_3$) δ: 7.30 (m, 5H, C$_6$H$_5$), 5.24 (m, 1H, H-2), 4.56 (d, 1H, J=12.1 Hz, C$_6$H$_5$CH), 4.52 (d, 1H, J=12.1 Hz, C$_6$H$_5$CH), 1.25 (m, 72H, 36CH$_2$), 0.88 (t, 6H, J=7.0 Hz, 2CH$_2$CH$_3$).

B 1,2-Di-O-docosanoyl-Sn-glycerol

3-O-Benzyl-1,2-di-O-docosanoyl-Sn-glycerol (1.25 g) was reacted by the general procedure according to Example 15-B to obtain the title compound (0.98 g, 88%) as white solid.

$^1$H-NMR (CDCl$_3$) δ: 5.08 (m, 1H, H-2), 4.32 (dd, 1H, J=4.6, 11.9 Hz, H-3), 4.24 (dd, 1H, J=5.7, 11.9 Hz, H-3), 3.73 (m, 2H, CH$_2$-1), 1.25 (m, 72H, 36CH$_2$), 0.88 (t, 6H, J=7.0 Hz, 2CH$_2$CH$_3$).

C 3-O-[Methyl(5-acetamido-4,7,8,9-tetra-O-levulinoyl-3,5-dideoxy-D-glycero-α-D-galacto-2-nonulopyranosyl)onate]-1,2-di-O-docosanoyl-Sn-glycerol Methyl 5-acetamido-3,5-dideoxy-D-glycero-D-galacto-2-nonulopyranosonate [Chem. Ber., 99, 611 (1966)] (3.23 g, 10.0 mmol), 4-dimethylaminopyridine (0.61 g, 0.50 mmol), levulinic acid (12.3 ml, 120 mmol) and dicyclohexylcarbodiimide (24.76 g, 120 mmol) were stirred in pyridine (30 ml) at room temperature for two days. The reaction solution was filtered through celite, and the filtrate was evaporated to dryness in vacuo. The residue was purified by silica gel column chromatography (with 170 g of gel, chloroform/methanol, 24:1) to obtain the penta-levulinoyl derivative (4.62 g, 65%) of the title compound. Then the penta-levulinoyl derivative (2.50 g, 3.07 mmol) was dissolved in acetyl chloride (30 ml), saturated with hydrogen chloride gas at 0° C., left at standing at 2° C. for five days. The reaction solution was evaporated to dryness in vacuo to obtain the chloride derivative (2.15 g, 95%) of the title compound. Then, the chloride derivative (1.22 g, 1.66 mmol) and 1,2-di-O-docosanoyl-Sn-glycerol (0.89 g, 1.21 mmol) were reacted by the general procedure according to Example 15-C to obtain the title compound (64 mg, 4%) as white solid.

$^1$H-NMR (CDCl$_3$) δ: 5.06 (dt, 1H, J=4.6, 11.7 Hz, H-4), 3.81 (s, 3H, COOCH$_3$), 2.19 (6H), 2.18, 2.17 (3s, 12H, 3CH$_3$CO), 1.89 (s, 3H, NAc), 1.85 (t, 1H, J=12.5 Hz, H-3ax), 1.25 (m, 72H, 36CH$_2$), 0.88 (t, 6H, J=7.0 Hz, 2CH$_2$CH$_3$).

Example 37

3-O-[(5-Acetamido-3,5-dideoxy-D-glycero-α-D-galacto-2-nonulopyranosonic acid-2-yl]-1,2-di-O-docosanoyl-Sn-glycerol 3-O-[Methyl(5-acetamido-4,7,8,9-tetra-O-levulinoyl-3,5-dideoxy-D-glycero-α-D-galacto-2-nonulopyranosyl)onate]-1,2-di-O-docosanoyl-Sn-glycerol (52 mg, 0.036 mmol) and anhydrous lithium iodide (49 mg, 0.366 mmol) were stirred in dehydrated pyridine (1.8 ml) at 80° C. for 6 h. The reaction solution was directly purified by gel chromatography (using Sephadex LH-20, 100 ml, chloroform/methanol, 1:1) to obtain lithium salt of title compound (34.6 mg, 67%) as white solid. The lithium salt (34.6 mg, 0.0242 mmol) was dissolved in methanol (0.5 ml) and chloroform (0.5 ml), added with hydrazine acetate (48 mg, 0.524 mmol), and the mixture was stirred at room temperature for 10 min. The reaction solution was adjusted to pH 4 with 0.1N-hydrochloric acid, and purified by gel chromatography (Sephadex LH-20, 75 ml, chloroform/methanol, 1:1) to obtain the title compound (23 mg, 92%) as white solid.

$^1$H-NMR (CDCl$_3$-CD$_3$OD, 1:1, 40° C.) δ: 2.76 (dd, 1H, J=4.2, 12.6 Hz, H-3eq), 2.03 (s, 3H, NAc), 1.74 (t, 1H, J=11.9 Hz, H-3ax), 1.28 (m, 72H, 36CH$_2$), 0.89 (t, 6H, J=7.0 Hz, 2CH$_2$CH$_3$).

Example 38

3-O-[Sodium{5-acetamido-3,5-dideoxy-4,7,8,9-tretra-O-(sodium oxysulfonyl)-D-glycero-α-D-galacto-2-nonulopyranosyl}onate]-1,2-di-O-docosanoyl-Sn-glycerol 3-O-[(5-Acetamido-3,5-dideoxy-D-glycero-α-D-galacto-2-nonulopyranosonic acid)-2-yd]-1,2-di-O-docosanoyl-Sn-glycerol (12 mg) was reacted by the general procedure according to Example 1 to obtain the title compound (9 mg, 53%) as white solid.

$^1$H-MR (CD3OD-D2O, 1:1, 50° C.) δ: 2.94 (BR. DD, 1H, H-3eq), 1.95 (s, 3H, ANC), 1.71 (t, 1H, J=11.0 Hz, H-ax), 1.26 (m, 72H, 36CH2), 0.87 (t, 6H, J=6.8 Hz, 2CH2CH3).

Example 39

3-O-[Methyl(4,5,7,8,9-penta-O-acetyl-3-deoxy-D-glycero-α-D-galacto-2-nonulopyranosyl)onate]-1,2-di-O-docosyl-Sn-glycerol 1,2-Di-O-docosyl-Sn-glycerol [Japanese Patent Laid-Open Publication No. Hei 1-125394] (467 mg) and methyl 4,5,7,8,9-penta-O-acetyl-2-chloro-2,3-dideoxy-D-glycero-β-D-galacto-2-nonulopyranosonate [Chem. Pharm. Bull., 39, 3140 (1991)] (281 mg) were reacted by the general procedure according to Example 15-C to obtain the title compound (313 mg, 48%) as white solid.

$^1$H-NMR (CDCl$_3$) δ: 3.80 (s, 3H, OCH$_3$, 2.68 (dd, 1H, J=4.0, 12.8 Hz, H-3eq), 2.15, 2.09, 2.04, 2.00, 2.00 (5s, 15H, 5Ac), 1.25 (m, 76H, 38CH$_2$), 0.88 (t, 6H, J=6.6 Hz, 2CH$_2$CH$_3$).

Example 40

3-O-[(3-Deoxy-D-glycero-α-D-galacto-2-nonulopyranosonic acid acid)-2-yl]-1,2-di-O-docosyl-Sn-glycerol 3-O-[Methyl(4,5,7,8,9-penta-O-acetyl-3-deoxy-D-glycero-α-D-galacto-2-nonulopyranosyl)onate]-1,2-di-O-docosyl-Sn-glycerol (313 mg) was reacted by the general procedure according to Example 16 to obtain the title compound (186 mg, 75%) as white solid.

$^1$H-NMR (CDCl$_3$-CD$_3$OD, 1:1, 60° C.) δ: 2.68 (dd, 1H, J=4.6, 12.6 Hz, H-3eq), 1.73 (t, 1H, J=12.1 Hz, H-3ax), 1.29 (m, 76H, 38CH$_2$), 0.89 (t, 6H, J=7.0 Hz, 2CH$_2$CH$_3$).

Example 41

3-O-[Sodium{3-deoxy-4,5,7,8,9-penta-O-(sodium oxysulfonyl)-D-glycero-α-D-galacto-2-nonulopyranosyl}onate]-1,2-di-O-docosyl-Sn-glycerol 3-O-[(3-Deoxy-D-glycero-α-D-galacto-2-nonulopyranosonic acid)-2-yl]-1,2-di-O-docosyl-Sn-glycerol (97 mg) was reacted by the general procedure according to Example 1 to obtain the title compound (15 mg, 10%) as white solid.

$^1$H-NMR (CD$_3$OD-D$_2$O, 1:1, 50° C.) δ: 2.89 (br. dd, 1H, H-3eq), 1.81 (br. t, 1H, H-3ax), 1.26 (m, 76H, 38CH$_2$), 0.86 (t, 6H, J=7.0 Hz, 2CH$_2$CH$_3$).

Example 42

1-O-[Methyl(5-acetamido-4,7,8,9-tetra-O-acetyl-3,5-dideoxy-D-glycero-α-D-galacto-2-nonulopyranosyl)onate]-L-2,3-di-O-docosyl-Sn-glycerol A L-1-O-Benyl-2,3-di-O-isopropylidene-Sn-glycerol After L-2,3-di-O-isopropylidene-Sn-glycerol (5.00 g, 37.8 mmol) and 60% sodium hydride (3.03 g, 75.8 mmol) were stirred in dehydrated dimethylformamide (110 ml) at room temperature for 10 min, benzyl bromide (6.7 ml, 56.7 mmol) was added, and the resulting mixture was stirred at room temperature for 3 h. The reaction solution was diluted with ether, washed successively with water and saturated sodium chloride solution, dried over anhydrous magnesium sulfate, and concentrated in vacuo. The residue was distilled under reduced pressure (110° C./3 torr) to obtain the benzyl derivative (6.65 g, 80%). Then, to a solution of this product (6.65 g, 29.9 mmol) dissolved in dichloromethane (30 ml), methanol (9 ml) and water (3 ml) was added trifluoroacetic acid (3 ml), and the mixture was stirred at room temperature for 3 h. After the reaction solution was neutralized with sodium hydroxide and condensed in vacuo, the residue was purified by distillation under reduced pressure to obtain the title compound (4.71 g, 86%).

¹H-NMR (CDCl₃) δ: 7.32 (m, 5H, C₆H₅), 4.56 (s, 2H, CH₂Ph).

B L-1-O-Benzyl-2,3-di-O-docosyl-Sn-glycerol

L-1-O-Benzyl-Sn-glycerol (1.90 g) and 1-bromo docosane (9.70 g) were reacted by the general procedure according to Example 15-A to obtain the title compound (7.0 g, 85%).

¹H-NMR (CDCl₃) δ: 7.30 (m, 5H, C₆H₅), 4.55 (s, 2H, CH₂Ph), 1.25 (m, 76H, 38CH₂), 0.88 (t, 6H, J=6.6 Hz, 2CH₂CH₃).

C L-2,3-Di-O-docosyl-Sn-glycerol

L-1-O-Benzyl-2,3-di-O-docosyl-Sn-glycerol (1.40 g) was reacted by the general procedure according to Example 15-B to obtain the title compound (0.99 g, 79%) as white solid.

¹H-NMR (CDCl₃) δ: 1.25 (m, 76H, 38CH₂), 0.88 (t, 6H, J=6.6 Hz, 2CH₂CH₃).

D 3-O-[Methyl(5-acetamido-4,7,8,9-tetra-O-acetyl-3,5-dideoxy-D-glycero-α-D-galacto-2-nonulopyranosyl)onate]-L-2,3-di-O-docosyl-Sn-glycerol L-2,3-Di-O-docosyl-Sn-glycerol (990 mg) and methyl 5-acetamido-4,7,8,9-tetra-O-acetyl-2-chloro-2,3,5-trideoxy-D-glycero-β-D-galacto-2-nonulopyranosonate [Chem. Ber., 99, 611 (1966)] (850 mg) were reacted by the general procedure according to Example 15-C to obtain the title compound (662 mg, 40%) as white solid.

¹H-NMR (CDCl₃) δ: 3.79 (s, 3H, OCH₃), 2.60 (dd, 1H, J=4.8, 12.8 Hz, H-3eq.), 2.15, 2.09, 2.04, 2.00, 2.00 (5s, 15H, 5Ac), 1.96 (t, 1H, J=12.8 Hz, H-3ax.), 1.25 (m, 76H, 38CH₂), 0.88 (t, 6H, J=6.6 Hz, 2CH₂CH₃).

Example 43

1-O-[(5-Acetamido-3,5-dideoxy-D-glycero-α-D-galacto-nonulopyranosonic acid)-2-yl]-L-2,3-di-O-docosyl-Sn-glycerol 1-O-[Methyl(5-acetamido-4,7,8,9-tetra-O-acetyl-3,5-dideoxy-D-glycero-α-D-galacto-2-nonulopyranosyl)onate]-L-2,3-di-O-docosyl-Sn-glycerol (632 mg) was reacted by the general procedure according to Example 16 to obtain the title compound (500 mg, 92%) as white solid.

¹H-NMR (CDCl₃-CD₃OD, 1:1, 40° C.) δ: 2.77 (dd, 1H, J=4.6, 13.4 Hz, H-3eq.), 2.02 (s, 3H, NAc), 1.74 (t, 1H, J=11.9 Hz, H-3ax.), 1.28 (m, 76H, 38CH₂), 0.89 (t, 6H, J=6.8 Hz, 2CH₂CH₃).

Example 44

1-O-[Sodium{5-acetamido-3,5-dideoxy-4,7,8,9-tetra-O-(sodium oxysulfonyl)-D-glycero-α-D-galacto-2-nonulopyranosyl}onate]-L-2,3-di-O-docosyl-Sn-glycerol 1-O-[(5-Acetamido-3,5-dideoxy-D-glycero-α-D-galacto-nonulopyranosonic acid)-2-yl]-L-2,3-di-O-docosyl-Sn-glycerol (200 mg) was reacted by the general procedure according to Example 1 to obtain the title compound (237 mg, 83%) as white solid.

¹H-NMR (CD₃OD-D₂O, 1:1, 40° C.) δ: 2.93 (br.dd, 1H, H-3eq), 1.96 (s, 3H, NAc), 1.77 (br.t, 1H, H-3ax), 1.28 (m, 76H, 38CH₂), 0.87 (t, 6H, J=6.6 Hz, 2CH₂CH₃).

Example 45

Methyl[2,2-bis(oleyl oxymethyl)propyl 5-acetamido-4,7,8,9-tetra-O-acetyl-3,5-dideoxy-D-glycero-α-D-galacto-2-nonulopyranosid]onate A 2,2-Bis(Oleyl oxymethyl)propanol 1,1,1-Tris(hydroxymethyl)ethane (1.0 g) and oleyl chloride (5.25 g) were reacted by the general procedure according to Example 15-A to obtain the title compound (2.91 g, 57%) as white solid.

¹H-NMR (CDCl₃) δ: 5.36 (m, 4H, 2CH=CH), 3.56 (d, 2H, J=5.9 Hz, CH₂OH), 1.27 (m, 40H, 20CH₂), 0.88 (t, 6H, J=6.6 Hz, 2CH₂CH₃), 0.85 (s, 3H, CCH₃).

B Methyl[2,2-bis(oleyl oxymethyl)propyl 5-acetamido-4,7,8,9-tetra-O-acetyl-3,5-dideoxy-D-glycero-α-D-galacto-2-nonulopyranosid]onate 2,2-Bis(oleyl oxymethyl)propanol (400 mg) and methyl 5-acetamido-4,7,8,9-tetra-O-acetyl-2-hloro-2,3,5-trideoxy-D-glycero-β-D-galacto-2-nonulopyranosonate [Chem. Ber., 99, 611 (1966)] (328 mg) were reacted by the general procedure according to Example 15-C to obtain the title compound (564 mg, 80%) as white solid.

¹H-NMR (CDCl₃) δ: 5.35 (m, 4H, 2CH=CH), 3.78 (s, 3H, COOCH₃), 2.58 (dd, 1H, J=5.0, 12.8 Hz, H-3eq.), 2.13, 2.12, 2.04, 2.02, 1.88 (5s, 15H, 5Ac), 1.27 (m, 40H, 20CH₂), 0.90 (s, 3H, CCH₃), 0.88 (t, 6H, J=6.9 Hz, 2CH₂CH₃).

Example 46

2,2-Bis(oleyl oxymethyl)propyl 5-acetamido-3,5-dideoxy-D-glycero-α-D-galacto-2-nonulopyranosidonic acid:

Methyl[2,2-bis(oleyl oxymethyl)propyl 5-acetamido-4,7,8,9-tetra-O-acetyl-3,5-dideoxy-D-glycero-α-D-galacto-2-nonulopyranosid]onate (250 mg) was reacted by the general procedure according to Example 16 to obtain the title compound (190 mg, 89%) as white solid.

¹H-NMR (CDCl₃-CD₃OD, 1:1) δ: 5.35 (m, 4H, 2CH=CH), 2.76 (dd, 1H, J=4.2, 13.4 Hz, H-3eq), 2.05 (s, 3H, NAc), 1.70 (t, 1H, J=11.9 Hz, H-3ax), 1.30 (m, 40H, 20CH₂), 0.92 (s, 3H, CCH₃), 0.89 (t, 6H, J=6.8 Hz, 2CH₂CH₃).

Example 47

Sodium[2,2-bis(oleyl oxymethyl)propyl 5-acetamido-3,5-dideoxy-4,7,8,9-tetra-O-(sodium oxysulfonyl)-D-glycero-α-D-galacto-2-nonulopyranosid)onate 2,2-Bis(oleyl oxymethyl)propyl 5-acetamido-3,5-dideoxy-D-glycero-α-D-galacto-2-nonulopyranosidonic acid (913 mg) was reacted by the general procedure according to Example 1 to obtain the title compound (63 mg, 47%) as white solid.

¹H-NMR (CD₃OD-D₂O, 1:1, 50° C.) δ: 5.37 (m, 4H, 2CH=CH), 2.95 (dd, 1H, J=5.3, 12.6 Hz, H-3eq), 1.97 (s, 3H, NAc), 1.74 (t, 1H, J=12.8 Hz, H-3ax), 1.28 (m, 40H, 20CH₂), 0.94 (s, 3H, CCH₃), 0.89 (t, 6H, J=6.8 Hz, 2CH₂CH₃).

Example 48

Methyl[2,2-bis(docosyloxymethyl)butyl 5-acetamido-4,7,8,9-tetra-O-acetyl-3,5-dideoxy-D-glycero-α-D-galacto-2-nonulopyranosid]onate A 2,2-Bis(docosyloxymethyl)butanol 1,1,1-Tris(hydroxymethyl)propane (1.0 g) and 1-bromo docosane (7.3 g) were reacted by the general procedure according to Example 15-A to obtain the title compound (3.12 g, 56%) as white solid.

¹H-NMR (CDCl₃) δ: 3.59 (d, 2H, J=5.9 Hz, CH₂OH), 1.25 (m, 76H, 38CH₂), 0.88 (t, 6H, J=6.7 Hz, 2CH₂CH₃), 0.84 (t, 3H, J=7.5 Hz, CCH₂CH₃).

B Methyl[2,2-bis(docosyloxymethyl)butyl 5acetamido-4,7,8,9-tetra-O-acetyl-3,5-dideoxy-D-glycero-α-D-galacto-2-nonulopyranosid]onate 2,2-Bis(docosyloxymethyl)butanol (2.26 g) and methyl 5-acetamido-4,7,8,9-tetra-O-acetyl-2-chloro-2,3,5-trideoxy-D-glycero-β-D-galacto-2-nonulopyranosonate [Chem. Ber., 99, 611 (1966)] (1.02 g) were reacted by the general procedure according to Example 15-C to obtain the title compound (539 mg, 22%) as white solid.

¹H-NMR (CDCl₃) δ: 3.78 (s, 3H, COOCH₃), 2.58 (dd, 1H, J=4.8, 12.8 Hz, H-3eq.), 2.13, 2.12, 2.04, 2.02, 1.88 (5s, 15H, 5Ac), 1.95 (t, 1H, J=12.5 Hz, H-3ax.), 1.25 (m, 76H, 38CH₂), 0.88 (t, 6H, J=7.0 Hz, 2CH₂CH₃), 0.84 (t, 3H, J=7.5 Hz, CCH₂CH₃).

Example 49
2,2-Bis(docosyloxymethyl)butyl 5-acetamido-3,5-dideoxy-D-glycero-α-D-galacto-2-nonulopyranosidonic acid:

Methyl[2,2-bis(docosyloxymethyl)butyl 5-acetamido-4,7,8,9-tetra-O-acetyl-3,5-dideoxy-D-glycero-α-D-galacto-2-nonulopyranosid]onate (520 mg) was reacted by the general procedure according to Example 16 to obtain the title compound (393 mg, 90%) as white solid.

$^1$H-NMR (CDCl$_3$-CD$_3$OD, 1:1, 60° C.) δ: 2.72 (dd, 1H, J=5.1, 12.1 Hz, H-3eq), 2.02 (s, 3H, NAc), 1.80 (t, 1H, J=11.9 Hz, H-3ax), 1.28 (m, 76H, 38CH$_2$), 0.89 (t, 6H, J=7.0 Hz, 2CH$_2$CH$_3$), 0.86 (t, 3H, J=7.7 Hz, CCH$_2$CH$_3$).

Example 50
Sodium[2,2-bis(docosyloxymethyl)butyl 5-acetamido-3,5-dideoxy-4,7,8,9-tetra-O-(sodium oxysulfonyl)-D-glycero-α-D-galacto-2-nonulopyranosid)onate 2,2-Bis(docosyloxymethyl)butyl 5-acetamido-3,5-dideoxy-D-glycero-β-D-galacto-2-nonulopyranosidonic acid (388 mg) was reacted by the general procedure according to Example 1 to obtain the title compound (332 mg, 61%) as white solid.

$^1$H-NMR (CD$_3$OD-D$_2$O, 1:1, 60° C.) δ: 2.95 (br.dd, 1H, H-3eq), 1.96 (s, 3H, NAc), 1.78 (br.t, 1H, H-3ax), 1.27 (m, 76H, 38CH$_2$), 0.87 (t, 9H, J=7.0 Hz, 3CH$_2$CH$_3$).

Example 51
3-O-[Methyl{5-N-(O-acetylglycolyl)-4,7,8,9-tetra-O-acetyl-3,5-dideoxy-D-glycero-α-D-galacto-2-nonulopyranosyl}onate]-1,2-di-O-docosyl-Sn-glycerol

[1,2-Di-O-docosyl-Sn-glycerol (400 mg) and methyl 5-N-(O-acetylglycolyl)-4,7,8,9-tetra-O-acetyl-2-chloro-2,3,5-trideoxy-D-glycero-β-D-galacto-2-nonulopyranosonate [Carbohydr. Res., 174, 73 (1988)] (300 mg) were reacted by the general procedure according to Example 15-C to obtain the title compound (66 mg, 10%) as white solid.

$^1$H-NMR (CDCl$_3$) δ: 4.60, 4.29 (2d, 2H, J=5.0 Hz, NHCOCH$_2$), 3.81 (s, 3H, OCH$_3$), 2.62 (dd, 1H, J=4.8, 12.8 Hz, H-3eq), 2.20, 2.15, 2.13, 2.04, 2.01 (5s, 15H, 5OAc), 1.25 (m, 76H, 38CH$_2$), 0.88 (t, 6H, J=7.0 Hz, 2CH$_2$CH$_3$).

Example 52
3-O-[(5-N-glycolyl-3,5-dideoxy-D-glycero-α-D-galacto-nonulopyranosonic acid)-2-yl]-1,2-di-O-docosyl-Sn-glycerol 3-O-[Methyl{5-N-(O-acetylglycolyl)-4,7,8,9-tetra-O-acetyl-3,5-dideoxy-D-glycero-α-D-galacto-2-nonulopyranosyl}onate]-1,2-di-O-docosyl-Sn-glycerol (60 mg) was reacted by the general procedure according to Example 16 to obtain the title compound (43 mg, 88%) as white solid.

$^1$H-NMR (CDCl$_3$-CD$_3$OD, 1:1, 60° C.) δ: 2.78 (dd, 1H, J=4.0, 12.0 Hz, H-3eq), 1.79 (t, 1H, J=12.0 Hz, H-3ax), 1.28 (m, 76H, 38CH$_2$), 0.89 (t, 6H, J=7.0 Hz, 2CH$_2$CH$_3$).

Example 53
3-O-[Sodium{5-N-(O-sodium oxysulfonylglycolyl)-3,5-dideoxy-4,7,8,9-tetra-O-(sodium oxysulfonyl)-D-glycero-α-D-galacto-2-nonulopyranosyl}onate]-1,2-di-O-docosyl-Sn-glycerol 3-O-[{-N-glycolyl-3,5-dideoxy-D-glycero-α-D-galacto-nonulopyranosonic acid}-2-yl]-1,2-di-O-docosyl-Sn-glycerol (41 mg) was reacted by the general procedure according to Example 1 to obtain the title compound (16 mg, 26%) as white solid.

$^1$H-NMR (CD$_3$OD-D$_2$O, 1:1, 60° C.) δ: 2.99 (br.dd, 1H, H-3eq), 1.92 (br.t, 1H, H-3ax), 1.30 (m, 76H, 38CH$_2$), 0.90 (t, 6H, J=7.0 Hz, 2CH$_2$CH$_3$).

Example 54
3-S-[Methyl(5-acetamido-4,7,8,9-tetra-O-acetyl-3,5-dideoxy-D-glycero-α-D-galacto-2-nonulopyranosyl)onate]-1,2-di-O-docosyl-Sn-thioglycerol A 3-Bromo-3-deoxy-1,2-di-O-docosyl-Sn-glycerol 1,2-Di-O-docosyl-Sn-glycerol (200 mg, 0.28 mmol), N-bromosuccinimide (90 mg, 0.51 mmol) and triphenylphosphine (170 mg, 0.65 mmol) were stirred in toluene (12 ml) at room temperature for 3 days. The reaction solution was condensed in vacuo, and the residue was purified by silica gel column chromatography (with 20 g of gel, hexane/toluene, 3:2) to obtain the title compound (168 mg, 77%) as white powder.

$^1$H-NMR (CDCl$_3$) δ: 1.25 (m, 76H, 38CH$_2$), 0.88 (t, 6H, J=7.0 Hz, 2CH$_2$CH$_3$).

B 3-S-[Methyl(5-acetamido-4,7,8,9-tetra-O-acetyl-3,5-dideoxy-D-glycero-α-D-galacto-2-nonulopyranosyl)onate]-1,2-di-O-docosyl-Sn-thioglycerol Methyl 5-acetamido-4,7,8,9-tetra-O-acetyl-2-S-acetyl-3,5-dideoxy-2-thio-D-glycero-α-D-galacto-2-nonulopyranosonate [J. Carbohydr. Chem., 5, 11 (1986)] (114 mg, 0.21 mmol) and sodium methoxide (11 mg, 0.20 mmol) were stirred in anhydrous methanol (0.5 ml) at −10° C. for 1 h, and the reaction solution was evaporated to dryness in vacuo. To the residue were added a solution of 3-bromo-3-deoxy-1,2-di-O-docosyl-Sn-glycerol (160 mg, 0.21 mmol) in dehydrated dimethylformamide (1.0 ml) and toluene (1.0 ml), and the mixture was stirred at room temperature for two days. The reaction solution was diluted with chloroform, washed with a saturated sodium chloride solution, and dried over anhydrous magnesium sulfate. After the solvent was distilled off in vacuo, the residue were purified by silica gel column chromatography (27 g of gel, toluene-acetone, 5:1) to obtain the title compound (85 mg, 34%) as white powder.

$^1$H-NMR (CDCl$_3$) δ: 3.79 (s, 3H, COOCH$_3$), 2.91 (dd, 1H, J=4.8, 13.0 Hz, H-3eq.), 2.72 (m, 2H, SCH$_2$), 2.15, 2.13, 2.04, 2.03, 1.88 (5s, 15H, 5Ac), 2.00 (t, 1H, J=12.8 Hz, H-3ax.), 1.25 (m, 76H, 38CH$_2$), 0.88 (t, 6H, J=7.1 Hz, 2CH$_2$CH$_3$).

Example 55
3-S-[(5-Acetamido-3,5-dideoxy-D-glycero-α-D-galacto-nonulopyranosonic acid)-2-yl]-1,2-di-O-docosyl-Sn-thioglycerol 3-S-[Methyl(5-acetamido-4,7,8,9-tetra-O-acetyl-3,5-dideoxy-D-glycero-α-D-galacto-2-nonulopyranosyl)onate]-1,2-di-O-docosyl-Sn-thioglycerol (154 mg) was reacted by the general procedure according to Example 16 to obtain the title compound (115 mg, 86%) as white solid.

$^1$H-NMR (CDCl$_3$-CD$_3$OD, 1:1, 60° C.) δ: 2.94 (dd, 1H, J=4.6, 12.8 Hz, H-3eq), 2.84 (m, 2H, SCH$_2$), 2.02 (s, 3H, NAc), 1.84 (t, 1H, J=11.6 Hz, H-3ax), 1.29 (m, 76H, 38CH$_2$), 0.89 (t, 6H, J=6.9 Hz, 2CH$_2$CH$_3$).

Example 56
3-S-[Sodium{5-acetamido-3,5-dideoxy-4,7,8,9-tetra-O-(sodium oxysulfonyl)-D-glycero-α-D-galacto-2-nonulopyranosyl}onate]-1,2-di-O-docosyl-Sn-thioglycerol 3-S-[(5-Acetamido-3,5-dideoxy-D-glycero-α-D-galacto-nonulopyranosonic acid)-2-yl]-1,2-di-O-docosyl-Sn-thioglycerol (422 mg) was reacted by the general procedure according to Example 1 to obtain the title compound (29 mg, 45%) as white solid.

$^1$H-NMR (CD$_3$OD-D$_2$O, 1:1, 50° C.) δ: 3.06 (br.dd, 1H, H-3eq), 2.90 (m, 2H, SCH$_2$), 1.90 (s, 3H, NAc), 1.30 (m, 76H, 38CH$_2$), 0.88 (t, 6H, J=7.0 Hz, 2CH$_2$CH$_3$).

Example 57
1-[N-(5-acetamido-4,7,8,9-tetra-O-acetyl-3,5-dideoxy-2-O-methyl-D-glycero-β-D-galacto-2-nonulopyranosonyl)amino]-2,2-bis(docosyloxymethyl)propane A 2,2-Bis(docosyloxymethyl)propyl methanesulfonate After a mixture of 2,2-bis(docosyloxymethyl)propanol (7.37 g; 10 mmol), methanesulfonyl chloride (1.3 ml; 16.8 mmol) and pyridine (150 ml) was stirred at 70° C. for 1 h, the reaction mixture was poured into water. Precipitates thus obtained were collected by suction, washed successively with water and acetone, and dried to obtain the title compound (6.66 g, 82%).

$^1$H-NMR (CDCl$_3$) δ: 4.13 (s, 2H, CH$_2$OMs), 2.98 (s, 3H, CH$_3$SO$_2$), 1.26 (m, 76H, 38CH$_2$), 1.00 (s, 3H, CCH$_3$), 0.88 (t, 6H, J=7.0 Hz, 2CH$_2$CH$_3$).

B 1-Azido-2,2-bis(docosyloxymethyl)propane

After a mixture of 2,2-bis(docosyloxymethyl)propyl methanesulfonate (22.7 g; 27.8 mmol), sodium azide (0.27 g; 83.5 mmol), and dimethylformamide (150 ml) was stirred at 110° C. for 20 h, the reaction mixture was poured into water. Precipitates thus obtained were collected by suction, washed successively with water and acetone, and dried to obtain the title compound (20.8 g; 98%).

$^1$H-NMR (CDCl$_3$) δ: 1.25 (m, 76H, 38CH$_2$), 0.89 (s, 3H, CCH$_3$), 0.88 (t, 6H, J=7.0 Hz, 2CH$_2$CH$_3$).

C 1-Amino-2,2-bis(docosyloxymethyl)propane

1-Azido-2,2-bis(docosyloxymethyl)propane (12.8 g; 16.8 mmol) and palladium hydroxide on carbon (6.0 g) in tetrahydrofuran (100 ml) was stirred under the hydrogen atmosphere at 50° C. for 3 h. The reaction solution was filtered through celite, and the filtrate was evaporated to dryness in vacuo. The residue was purified by silica gel column chromatography (60 g of gel, chloroform/methanol, 10:1) to obtain the title compound (8 g, 65%) as white powder.

D Methyl 5-acetamido-4,7,8,9-tetra-O-acetyl-3,5-dideoxy-D-glycero-β-D-galacto-2-nonulopyranosidonic acid:

After a mixture of methyl 5-acetamido-3,5-dideoxy-D-glycero-β-D-galacto-2-nonulopyranosidonic acid [Chem. Ber., 99, 611 (1966)] (150 mg; 0.464 mmol), acetic anhydride (2.3 ml) and pyridine (2.3 ml) was stirred at room temperature for 7 h, the reaction solution was evaporated to dryness in vacuo. The residue was dissolved in chloroform, and treated with Amberist-15 (H type) to obtain the title compound (218 mg, 96%) as white powder.

$^1$H-NMR (CDCl$_3$) δ: 3.33 (s, 3H, OCH$_3$), 2.56 (dd, 1H, J=4.8, 13.2 Hz, H-3eq.), 2.16, 2.11, 2.06, 2.04, 1.91 (5s, 15H, 5Ac).

E 1-[N-(5-acetamido-4,7,8,9-tetra-O-acetyl-3,5-dideoxy-2-O-methyl-D-glycero-β-D-galacto-2-nonulopyranosonyl) amino]-2,2-bis(docosyloxymethyl)propane After a mixture of methyl 5-acetamido-4,7,8,9-tetra-O-acetyl-3,5-dideoxy-D-glycero-β-D-galacto-2-nonulopyranosidonic acid (260 mg; 0.53 mmol), 1-amino-2,2-bis(docosyloxymethyl) propane (390 mg; 0.53 mmol), dicyclohexylcarbodiimide (165 mg; 0.80 mmol), 1-hydroxybenztriazole (95 mg; 0.70 mmol) and chloroform (11 ml) was stirred at room temperature for 17 h, the reaction solution was filtered through celite, an the solvent was distilled off in vacuo. The residue was purified by silica gel column chromatography (with 60 g of gel, chloroform-acetone, 17:3) to obtain the title compound (620 mg, 97%) as white powder.

$^1$H-NMR (CDCl$_3$) δ: 3.18 (s, 3H, OCH$_3$), 2.51 (dd, 1H, J=4.8, 13.2 Hz, H-3eq), 2.1 4, 2.08, 2.03, 2.01, 1.90 (5s, 15H, 5Ac), 1.77 (t, 1H, J=11.7 Hz, H-3ax), 1.25 (m, 76H, 38CH$_2$), 0.91 (s, 3H, CCH$_3$), 0.88 (t, 6H, J=6.6 Hz, 2CH$_2$CH$_3$).

Example 58

1-[N-(5-Acetamido-3,5-dideoxy-2-O-methyl-D-glycero-β-D-galacto-2-nonulopyranosonyl)amino]-2,2-bis (docosyloxymethyl)propane After a mixture of 1-[N-(5-acetamido-4,7,8,9-tetra-O-acetyl-3,5-dideoxy-2-O-methyl-D-glycero-β-D-galacto-2-nonulopyranosonyl)amino]-2,2-bis(docosyloxymethyl) propane (620 mg; 0.51 mmol), sodium methoxide (28 mg; 0.52 mmol), methanol (5 ml) and tetrahydrofuran (5 ml) was stirred at room temperature for 7 h, the reaction solution was neutralized with Amberlist-15 (H type), and evaporated to dryness in vacuo. The residue was purified by silica gel column chromatography (50 g of gel, chloroform/methanol, 10:1) to obtain the title compound (480 mg, 90%) as white powder.

$^1$H-NMR (CDCl$_3$-CD$_3$OD, 1:1) δ: 3.24 (s, 3H, OCH$_3$), 2.40 (dd, 1H, J=4.9, 13.0 Hz, H-3eq), 2.05 (s, 3H, NAc), 1.27 (m, 76H, 38CH$_2$), 0.91 (s, 3H, CCH$_3$), 0.89 (t, 6H, J=7.0 Hz, 2CH$_2$CH$_3$).

Example 59

1-[N-{5-Acetamido-3,5-dideoxy-2-O-methyl-4,7,8,9-tetra-O-(sodium oxysulfonyl)-D-glycero-β-D-galacto-2-nonulopyranosonyl}amino]-2,2-bis(docosyloxymethyl) propane 1-[N-(5-Acetamido-3,5-dideoxy-2-O-methyl-D-glycero-β-D-galacto-2-nonulopyranosonyl)amino]-2,2-bis (docosyloxymethyl) propane (831 mg) was reacted by the general procedure according to Example 1 to obtain the title compound (810 mg, 70%) as white solid.

$^1$H-NMR (CD$_3$OD-D$_2$O, 1:1, 40° C.) δ: 2.66 (br.dd, 1H, J=4.4, 12.5 Hz, H-3eq), 2.03 (s, 3H, NAc), 1.79 (br.t, 1H, H-3ax), 1.31 (m, 76H, 38CH$_2$), 0.91 (s, 3H, CCH$_3$), 0.91 (t, 6H, J=6.8 Hz, 2CH$_2$CH$_3$).

Example 60

1-[N-(5-Aetamido-4,7,8,9-tetra-O-acetyl-3,5-dideoxy-2-O-methyl-D-glycero-β-D-galacto-2-nonulopyranosonyl) amino]-2,2-bis(eicosyloxymethyl) propane A 2,2-Bis(eicosyl oxymethyl)propyl methanesulfonate 2,2-Bis(eicosyloxymethyl)propanol (1.19 g) was reacted by the general procedure according to Example 57-A to obtain the title compound (1.08 g, 82%) as white solid.

$^1$H-NMR (CDCl$_3$) δ: 4.13 (s, 2H, CH$_2$OMs), 2.98 (s, 3H, CH$_3$SO$_2$), 1.25 (m, 68H, 34CH$_2$), 1.00 (s, 3H, CCH$_3$), 0.88 (t, 6H, J=7.0 Hz, 2CH$_2$CH$_3$).

B 1-Azido-2,2-bis(eicosyloxymethyl)propane 2,2-Bis(eicosyloxymethyl)propyl methanesulfonate (1.05 g) was reacted by the general procedure according to Example 57-B to obtain the title compound (0.94 g, 96%) as white solid.

$^1$H-NMR (CDCl$_3$) δ: 1.25 (m, 68H, 34CH$_2$), 0.94 (s, 3H, CCH$_3$), 0.88 (t, 6H, J=7.0 Hz, 2CH$_2$CH$_3$).

C 1-Amino-2,2-bis(eicosyloxymethyl) propane

1-Azido-2,2-bis(eicosyloxymethyl) propane (360 mg) was reacted by the general procedure according to Example 57-C to obtain the title compound (206 mg, 59%) as white solid.

$^1$H-NMR (CDCl$_3$) δ: 2.74 (s, 2H, CH$_2$), 1.25 (m, 68H, 34CH$_2$), 0.90 (s, 3H, CCH$_3$), 0.88 (t, 6H, J=7.0 Hz, 2CH$_2$CH$_3$).

D 1-[N-(5-Acetamido-4,7,8,9-tetra-O-acetyl-3,5-dideoxy-2-O-methyl-D-glycero-β-D-galacto-2-nonulopyranosonyl) amino]-2,2-bis(eicosyloxymethyl)propane Methyl 5-acetamido-4,7,8,9-tetra-O-acetyl-3,5-dideoxy-D-glycero-β-D-galacto-2-nonulopyranosidonic acid (179 mg) and 1-amino-2,2-bis(eicosyloxymethyl)propane (206 mg) were reacted by the general procedure according to Example 57-E to obtain the title compound (327 mg, 94%) as white solid.

$^1$H-NMR (CDCl$_3$) δ: 3.18 (s, 3H, OCH$_3$), 2.51 (dd, 1H, J=5.0, 13.0 Hz, H-3eq), 2.14, 2.09, 2.04, 2.01, 1.91 (5s, 15H,

5Ac), 1.77 (dd, 1H, J=11.7, 12.8 Hz, H-3ax), 1.25 (m, 68H, 34CH$_2$), 0.91 (s, 3H, CCH$_3$), 0.88 (t, 6H, J=7.0 Hz, 2CH$_2$CH$_3$).

Example 61
1-[N-(5-Acetamido-3,5-dideoxy-2-O-methyl-D-glycero-β-D-galacto-2-nonulopyranosonyl)amino]-2,2-bis(eicosyloxymethyl) propane 1-[N-(5-Acetamido-4,7,8,9-tetra-O-acetyl-3,5-dideoxy-2-O-methyl-D-glycero-β-D-galacto-2-nonulopyranosonyl) amino]-2,2-bis(eicosyloxymethyl)propane (216 mg) was reacted by the general procedure according to Example 58 to obtain the title compound (202 mg, 74%) as white solid.

$^1$H-NMR (CDCl$_3$-CD$_3$OD, 10:1) δ: 3.22 (s, 3H, OCH$_3$), 2.36 (dd, 1H, J=4.8, 13.2 Hz, H-3eq), 2.04 (s, 3H, NAc), 1.26 (m, 68H, 34CH$_2$), 0.90 (s, 3H, CCH$_3$), 0.88 (t,6H, J=7.1 Hz, 2CH$_2$CH$_3$).

Example 62
1-[N-{5-Aetamido-3,5-dideoxy-2-O-methyl-4,7,8,9-tetra-O-(sodium oxysulfonyl)-D-glycero-β-D-galacto-2-nonulopyranosonyl}amino]-2,2-bis(eicosyloxymethyl) propane 1-[N-(5-Acetamido-3,5-dideoxy-2-O-methyl-D-glycero-β-D-galacto-2-nonulopyranosonyl)amino]-2,2-bis(eicosyloxymethyl)propane (422 mg) was reacted by the general procedure according to Example 1 to obtain the title compound (49 mg, 36%) as white solid.

$^1$H-NMR (CD$_3$OD-D$_2$O, 1:1, 40° C.) δ: 2.66 (br.dd, 1H, H-3eq), 2.02 (s, 3H, NAc), 1.78 (br.t, 1H, J=12.3 Hz, H-3ax), 1.30 (m, 68H, 34CH$_2$), 0.90 (s, 3H, CCH$_3$), 0.90 (t, 6H, J=7.0 Hz, 2CH$_2$CH$_3$).

Example 63
1-[N-(5-Acetamido-4,7,8,9-tetra-O-acetyl-3,5-dideoxy-2-O-ethyl-D-glycero-β-D-galacto-2-nonulopyranosonyl) amino]-2,2-bis(docosyloxymethyl) propane A Methyl(ethyl 5-acetamido-3,5-dideoxy-D-glycero-β-D-galacto-2-nonulopyranosid)onate A mixture of N-acetylneuraminic acid (1.00 g; 3.23 mmol), Dowex-50 (H form) (15 g) and dehydrated ethanol (100 ml) was heated at reflux for 18 h. The reaction mixture was packed into a column, and eluted with 2N-HCl-methanol (100 ml). After the solvent was distilled off in vacuo. The residue thus obtained was stirred with acetic anhydride (20 ml) and pyridine (20 ml) at room temperature for 17 h, and then the reaction solution was evaporated to dryness in vacuo. The residue was dissolved in chloroform, washed successively with 0.1N HCl, water and saturated NaCl solution, dried over anhydrous magnesium sulfate, and then the solvent was distilled off in vacuo. After the residue thus obtained was stirred with sodium methoxide (31 mg; 0.575 mmol) in methanol (23 ml) at room temperature for 17 h, the reaction mixture was neutralized with Dowex-50 (H form), and then the solvent was distilled off. The residue was purified by silica gel column chromatography (40 g of gel, chloroform/methanol, 4:1) to obtain the title compound (142 mg, 12%) as white powder.

$^1$H-NMR (CD$_3$OD) δ: 3.78 (s, 3H, OCH$_3$), 2.36 (dd, 1H, J=4.9, 13.0 Hz, H-3eq.), 2.00 (s, 3H, NAc), 1.62 (dd, 1H, J=11.4, 12.8 Hz, H-3ax.), 1.16 (t, 3H, J=7.0 Hz, CH$_2$CH$_3$).

B Methyl(ethyl 5-acetamido-4,7,8,9-tetra-O-acetyl-3,5-dideoxy-D-glycero-β-D-galacto-2-nonulopyranosid)onate Methyl(ethyl 5-acetamido-3,5-dideoxy-D-glycero-β-D-galacto-2-nonulopyranosid)onate (142 mg) was reacted by the general procedure according to Example 57-D to obtain the title compound (209 mg, 99%) as white solid.

$^1$H-NMR (CDCl$_3$) δ: 3.80 (s, 3H, COOCH$_3$), 2.45 (dd, 1H, J=5.1, 12.8 Hz, H-3eq.), 2.15, 2.08, 2.03, 2.02, 1.89 (5s, 15H, 5Ac), 1.87 (dd, 1H, J=11.4, 12.8 Hz, H-3ax.), 1.22 (t, 3H, J=7.1 Hz, CH$_2$CH$_3$).

C Ethyl 5-acetamido-4,7,8,9-tetra-O-acetyl-3,5-dideoxy-D-glycero-β-D-galacto-2-nonulopyranosidonic acid:

A mixture of methyl (ethyl 5-acetamido-4,7,8,9-tetra-O-acetyl-3,5-dideoxy-D-glycero-β-D-galacto-2-nonulopyranosid)onate (203 mg, 0.39 mmol), anhydrous lithium iodide (523 mg, 3.9 mmol) and pyridine (8.0 ml) was stirred at 90° C. for 14 h. The reaction solution was subjected to gel filtration (LH-20, 150 ml, methanol), and then purified by silica gel column chromatography (20 g of gel, chloroform/methanol, 7:3) to obtain the title compound (92 mg, 47%) as white solid.

$^1$H-NMR (CDCl$_3$) δ: 3.52 (m, 2H, CH$_2$CH$_3$), 2.56 (dd, 1H, J=4.5, 12.2 Hz, H-3eq.), 2.15, 2.11, 2.06, 2.04, 1.91 (5s, 15H, 5Ac), 1.92 (t, 1H, J=11.8 Hz, H-3ax.), 1.24 (t, 3H, J=7.0 Hz, CH$_2$CH$_3$).

D 1-[N-(5-Acetamido-4,7,8,9-tetra-O-acetyl-3,5-dideoxy-2-O-ethyl-D-glycero-β-D-galacto-2-nonulopyranosonyl) amino]-2,2-bis(docosyloxymethyl) propane Ethyl 5-acetamido-4,7,8,9-tetra-O-acetyl-3,5-dideoxy-D-glycero-β-D-galacto-2-nonulopyranosodonic acid (92 mg) and 1-amino-2,2-bis(docosyloxymethyl)propane (268 mg) were reacted by the general procedure according to Example 57-E to obtain the title compound (191 mg, 86%) as white solid.

$^1$H-NMR (CDCl$_3$) δ: 2.52 (dd, 1H, J=4.8, 13.2 Hz, H-3eq), 2.14, 2.08, 2.03, 2.01, 1.91 (5s, 15H, 5Ac), 1.76 (t, 1H, J=12.4 Hz, H-3ax), 1.25 (m, 76H, 38CH$_2$), 1.19 (t, 3H, J=7.0 Hz, OCH$_2$CH$_3$), 0.90 (s, 3H, CCH$_3$), 0.88 (t, 6H, J=7.0 Hz, 2CH$_2$CH$_3$).

Example 64
1-[N-(5-Acetamido-3,5-dideoxy-2-O-ethyl-D-glycero-β-D-galacto-2-nonulopyranosonyl)amino]-2,2-bis(docosyloxymethyl) propane 1-[N-(5-Acetamido-4,7,8,9-tetra-O-acetyl-3,5-dideoxy-2-O-ethyl-D-glycero-β-D-galacto-2-nonulopyranosonyl) amino]-2,2-bis(docosyloxymethyl)propane (185 mg) was reacted by the general procedure according to Example 58 to obtain the title compound (114 mg, 71%) as white solid.

$^1$H-NMR (CDCl$_3$-CD$_3$OD, 10:1) δ: 2.38 (dd, 1H, J=4.8, 13.2 Hz, H-3eq), 2.04 (s, 3H, NAc), 1.26 (m, 76H, 38CH$_2$), 1.17 (t, 3H, J=7.0 Hz, OCH$_2$CH$_3$), 0.89 (s, 3H, CCH$_3$), 0.88 (t, 6H, J=7.3 Hz, 2CH$_2$CH$_3$).

Example 65
1-[N-{5-Acetamido-3,5-dideoxy-2-O-ethyl-4,7,8,9-tetra-O-(sodium oxysulfonyl)-D-glycero-β-D-galacto-2-nonulopyranosonyl}amino]-2,2-bis(docosyloxymethyl) propane 1-[N-(5-Acetamido-3,5-dideoxy-2-O-ethyl-D-glycero-β-D-galacto-2-nonulopyranosonyl)amino]-2,2-bis(docosyloxymethyl) propane (422 mg) was reacted by the general procedure according to Example 1 to obtain the title compound (140 mg, 93%) as white solid.

$^1$H-NMR (CD$_3$OD-D$_2$O, 1:1, 40° C.) δ: 2.67 (br.dd, 1H, H-3eq), 2.02 (s, 3H, NAc), 1.77 (br.t, 1H, H-3ax), 1.30 (m, 76H, 38CH$_2$), 1.25 (t, 3H, J=7.0 Hz, OCH$_2$CH$_3$), 0.91 (t, 6H, J=6.8 Hz, 2CH$_2$CH$_3$), 0.90 (s, 3H, CCH$_3$).

Example 66
1-[N-(5-Acetamido-4,7,8,9-tetra-O-acetyl-3,5-dideoxy-2-O-methyl-D-glycero-α-D-galacto-2-nonulopyranosonyl) amino]-2,2-bis(docosyloxymethyl) propane A Methyl 5-acetamido-4,7,8,9-tetra-O-acetyl-3,5-dideoxy-D-glycero-α-D-galacto-2-nonulopyranosidonic acid:

Methyl 5-acetamido-3,5-dideoxy-D-glycero-α-D-galacto-2-nonulopyranosidonic acid [Chem. Ber., 99, 611

(1966)] (150 mg) was reacted by the general procedure according to Example 57-D to obtain the title compound (220 mg, 96%) as white solid.

$^1$H-NMR (CDCl$_3$-CD$_3$OD, 1:1) δ: 3.20 (s, 3H, OCH$_3$), 2.42 (dd, 1H, J=4.4, 12.5 Hz, H-3eq.), 1.96, 1.95, 1.87, 1.83, 1.70 (5s, 15H, 5Ac), 1.56 (t, 1H, J=12.5 Hz, H3ax.).

B 1-[N-(5-Acetamido-4,7,8,9-tetra-O-acetyl-3,5-dideoxy-2-O-methyl-D-glycero-α-D-galacto-2-nonulopyranosonyl)amino]-2,2-bis(docosyloxymethyl) propane Methyl 5-acetamido-4,7,8,9-tetra-O-acetyl-3,5-dideoxy-D-glycero-ct-D-galacto-2-nonulopyranosidonic acid (191 mg) and 1-amino-2,2-bis(docosyloxymethyl) propane (396 mg) were reacted by the general procedure according to Example 57-E to obtain the title compound (345 mg, 73%) as white solid.

$^1$H-NMR (CDCl$_3$) δ: 3.36 (s, 3H, OCH$_3$), 2.13, 2.08, 2.03, 2.01, 1.89 (5s, 15H, 5Ac), 1.98 (t, 1H, J=11.7 Hz, H3ax.) 1.25 (m, 76H, 38CH$_2$), 0.90 (s, 3H, CCH$_3$), 0.88 (t, 6H, J=7.0 Hz, 2CH$_2$CH$_3$).

Example 67

1-[N-(5-Acetamido-3,5-dideoxy-2-O-methyl-D-glycero-α-D-galacto-2-nonulopyranosonyl)amino]-2,2-bis(docosyloxymethyl) propane 1-[N-(5-Acetamido-4,7,8,9-tetra-O-acetyl-3,5-dideoxy-2-O-methyl-D-glycero-α-D-galacto-2-nonulopyranosonyl)amino]-2,2-bis(docosyloxymethyl)propane (340 mg) was reacted by the general procedure according to Example 58 to obtain the title compound (216 mg, 74%) as white solid.

$^1$H-NMR (CDCl$_3$-CD$_3$OD, 10:1) δ: 3.36 (s, 3H, OCH$_3$), 2.55 (dd, 1H, J=4.8, 13.2 Hz, H-3eq), 2.03 (s, 3H, NAc), 1.82 (dd, 1H, J=11.2, 13.0 Hz, H3ax.), 1.26 (m, 76H, 38CH$_2$), 0.91 (s, 3H, CCH$_3$), 0.88 (t, 6H, J=7.0 Hz, 2CH$_2$CH$_3$).

Example 68

1-[N-{5-Acetamido-3,5-dideoxy-2-O-methyl-4,7,8,9-tetra-O-(sodium oxysulfonyl)-D-glycero-α-D-galacto-2-nonulopyranosonyl}amino]-2,2-bis(docosyloxymethyl) propane 1-[N-(5-Acetamido-3,5-dideoxy-2-O-methyl-D-glycero-α-D-galacto-2-nonulopyranosonyl)amino]-2,2-bis(docosyloxymethyl)propane (117 mg) was reacted by the general procedure according to Example 1 to obtain the title compound (98 mg, 60%) as white solid.

$^1$H-MR (CD$_3$OD-D$_2$O, 1:1, 40° C.) δ: 2.55 (br.dd, 1H, J=5.1, 13.6 Hz, H-3eq), 1.99 (s, 3H, NAc), 1.30 (m, 76H, 38CH$_2$), 0.90 (br.t, 9H, J=6.6 Hz, CCH$_3$ and 2CH$_2$CH$_3$).

Assessment of Growth Inhibitory Effect on HIV-1 and Cytotoxicity

Samples of various concentrations (25 μl) are distributed into a 24-well microplate, immediately added with human T cells (H9 cell line, 1.2×10$^5$/ml) (1 ml), covered, and incubated at 37° C. for 1 h. Then, AIDS virus (HIV-1, IIIb, 100 TCID 50) (25 μl) is added to each well and thoroughly mixed, covered again, and incubated under the CO$_2$ atmosphere at 37° C. for 3 days. On the fourth day, aliquots (200 μl) of the culture medium from each well are transferred into a fresh microplate. The growth medium (500 μl) is added to each well, and further incubated for 2 days.

On the 6th day, aliquots (90 μl) of the culture supernatant are withdrawn, and assayed the amount of p24, a constituent of HIV-1, by ELISA method using the anti-p24 antibody to assess the growth of said virus. Also, using the remaining cell culture suspension (100 μl), viable cells are counted by the MTT method. Experimental values are expressed as the ratios (%) to the negative control value (measured using the solvent to dissolve test compounds as the sample) to represent the anti-HIV activity and cytotoxicity. Then, for the unified representation of the anti-HIV activity and cytotoxicity, the concentrations of test compounds at their 50% values are obtained from the activity-concentration curves and the cytotoxicity-concentration, and represented as IC50 and CC50, respectively.

Results of the Anti-HIV Activity Assay

In the following table are shown the compounds and their structural characteristics having IC50 (μM) values less than 100 μM. Carbon number of the functional group (in parentheses) represents that of alkyl group of lipid sidechain beyond the ether linkage, and, particularly, in the case where lipid is alkylglycerol, that of alkyl group of said alkyl glycerol.

TABLE 1

| Example No. | IC 50 (μM) | Functional group (carbon number) |
| --- | --- | --- |
| 5 | 46.0 | Two alkyl chains (10) |
| 6 | 50.0 | Two alkyl chains (10), β-isomer of 5 |
| 7 | 16.0 | Two alkyl chains (14) |
| 8 | 15.0 | Two alkyl chains (14) β-isomer of 7 |
| 9 | 3.8 | Two alkyl chains (18) |
| 10 | 30.0 | One alkyl chain (18), with a sulfate group as a side chain |
| 11 | 13.0 | One alkyl chain (18), β-isomer of 10 |
| 12 | 0.8 | Two alkyl chains (22) |
| 13 | 1.6 | Two alkyl chains (22), β-isomer of 12 |
| 14 | 15.0 | Two alkyl chains (14), thioglycoside |
| 17 | 2.5 | Two alkyl chains (20) |
| 20 | 1.2 | Two alkyl chains (24) |
| 24 | 34.0 | Cholesterol |
| 25 | 100.0 | One alkyl chain (18), unsaturated |
| 26 | 100.0 | One alkyl chain (18) |
| 29 | 1.6 | Two alkyl chains (22), branched |
| 32 | 2.5 | Two alkyl chains (20), branched |
| 35 | 90.0 | Aromatic |
| 38 | 2.5 | Two alkyl chains (22), glycero-ester |
| 41 | 4.0 | Two alkyl chains (22), KDN |
| 50 | 1.1 | Two alkyl chains (22), with an ethyl group at the branching point |
| 59 | 1.4 | Two alkyl chains (22), amide linkage |

These results indicate that, as the lipid bound to nonulonic acid (sialic acid and KDN) via glycosidic linkage are preferred alkyl, carbonyloxy or oxycarbonyl groups. Furthermore, no significant difference observed in the activity of Example 7 (O-glycoside) as compared with that of Example 14 (S-glycoside) indicates that the linkage between carbohydrate and lipid moieties can be either O-glycosidic or S-glycosidic. Also, no difference observed in the activity between Example 29 and Example 59, wherein they differ only in that the former has the O-glycosidic linkage and the latter the amide linkage, leads to the conclusion that the linkage between carbohydrate and lipid can be of any form.

So far as sulfuric acid derivatives of sialoglycerolipids are concerned, as evidently seen comparing Example 9 (two alkyl chains, each having 18 carbon atoms, IC50: 3.8) and Example 11 (one alkyl chain with 18 carbon atoms, IC50: 13.0), both derivatives, one with single chain, and the other with two chains, have the enough activity for the practical use, but the latter one is generally more active. Therefore, derivatives with two alkyl chains can be more preferable than those with one alkyl chain.

Also, as evidently seen comparing Example 38 (two alkyl chains, each having 22 carbon atoms, glyceroester, IC50: 2.5) and Example 12 (two alkyl chains, each having 22 carbon atoms, IC50: 0.8), these compounds have high activity regardless of whether their glycero-lipid moieties are either alkylglycerol or acylglycerol. Therefore, the biological activity is not so much affected by the linkage form between the glycerol skeleton and the long alkyl chain group, but rather mainly dependent on the length of long alkyl chain group.

So far as compounds wherein glycerol having two alkyl chains is linked to sugar via glycosidic linkage are concerned, as shown in Table 1, minimum IC50 values are associated mostly with those with carbon atoms of 18 (Example 9), 20 (Example 17), 22 (Example 12) and 24 (Example 20). Therefore, in the case where the sulfate derivatives of sialoglycerolipids related to this invention are either alkyl glycerol or acyl glycerol, number of carbon atoms of alkyl groups linked to the glycerol moiety is thought to be preferably 18~24. Since the biological activity depends mainly on the length of long-chain alkyl group linked to the glycerol skeleton, said long chain alkyl group can be saturated or unsaturated, also branched. In the case of alkyl glycerol with 24 carbon atoms as in Example 20, the "number of skeleton-forming atoms" per one side chain amounts to 25. This is because the "number of skeleton-forming atoms" includes the oxygen atom related to the ether linkage, in addition to carbon atoms of alkyl group. Furthermore, in the case of pseudo-glycerol as in Example 29 and Example 32, since the carbon atom of methylene group between the carbon atom at the β position of the main chain of glycerol moiety and the oxygen atom of the ether linkage is also included in the "number of skeleton-forming atoms", that number becomes 24 in the case of Example 29, and 22 in the case of Example 32.

Also, the glycerol moiety can have a methyl branch, and a methylene group between the main chain of the glycerol moiety and ether linkage or ester linkage (Example 29 and Example 32). Therefore, the glycerol moiety can have a short alkyl chain such as methyl, ethyl, propyl, butyl groups, etc. at the β carbon atom of its main chain (in this case, however, these groups cannot be called side chain or branched chain because of insufficient length of alkyl groups.), and one to three carbon atoms can be present between the main chain of glycerol moiety and the ether or ester linkage.

In comparison of Example 29 with Example 12, two chains extending from the β carbon atom of the main chain of glycerol moiety are of the same length in Example 29, while they are of the different length in Example 12. That is, in Example 29, number of "skeleton-forming atom" per one chain of the two chains extending from the β carbon atom of the main chain of glycerol moiety is the same 24, but different in Example 12, as 23 and 24. Therefore, it can be concluded that, in the case of two chains, number of "skeleton-forming atoms" per one chain, furthermore, number of alkyl chain-forming carbon atoms can be different. In addition, as to Example 29, it is advantageous that the two chains are completely the same having the same component atoms and configuration because for the easy preparation.

In the table below are shown CC50s.

TABLE 2

| Example No. | CC 50 ($\mu$M) | Example No. | CC 50 ($\mu$M) |
| --- | --- | --- | --- |
| 5 | >200 | 20 | >20 |
| 6 | >200 | 24 | >200 |
| 7 | >200 | 25 | >200 |
| 8 | >200 | 26 | >200 |
| 9 | >200 | 29 | >20 |
| 10 | >200 | 32 | >200 |
| 11 | 200 | 35 | >20 |
| 12 | >200 | 38 | >200 |
| 13 | >200 | 41 | >200 |

TABLE 2-continued

| Example No. | CC 50 ($\mu$M) | Example No. | CC 50 ($\mu$M) |
| --- | --- | --- | --- |
| 14 | >200 | 50 | >200 |
| 17 | >20 | 59 | >200 |

These results indicate that compounds related to the present invention are generally low in the cytotoxicity.

Assay of Antiviral Activity against other Viruses than HIV

Antiviral activity against human Parainfluenza virus, Respiratory syncytial virus (RSV) and Herpes simplex II virus (HSVII) was determined by the plaque reduction assay, while that against Feline immunodeficiency virus (FIV) and Feline leukemia virus (FeLV) by the reverse transcriptase assay and ELISA, respectively.

1) Plaque Reduction Assay
a) Preparation Viruse, Host Cell and Virus Stock

Each virus was obtained from ATCC. As host cells, VERO cells were used for Parainfluenza virus, and HEP2 cells for other viruses.

To fibroblasts growing in a T150 flask were added virus-infected cells, and the cells were incubated until they reached 60–80% infection. Cells were trypsinized, recovered and used as the virus stock. As the cell culture medium was used E-MEM containing 2–5% FBS, 100 U/ml Penicillin, 2.5 $\mu$g/ml Aniphotericin and 10 $\mu$g/ml Gentamycin.

b) Preparation of Sample

Compound related to Example 29 was appropriately diluted to the concentrations of 500, 100, 50, 10 and 5 $\mu$g/ml with the culture medium or methyl cellulose. As the reference drug for HSV II was used Acyclovir.

c) Assay Procedure

Anti-viral Activity

After cells were cultured in monolayer in 24-well microplates, the supernatant was discarded, replaced with a diluted sample (compound) solution (0.5 ml), and the mixture was incubated at 36–38° C. under the 5–7% $CO_2$ atmosphere for 1 h. At the same time, to the cell control well and virus control wells was added the equal amount of medium.

After the supernatant was discarded, the medium (0.5 ml) and the virus stock (0.2 ml) were added to the sample well and virus well, respectively. After incubating again for 1 h, the sample solution (1 ml) diluted with methylcellulose containing FBS was overlayered. To the control well was added only the same amount of the vehicle.

Cells were cultured at 36–38° C. under the 5–7% $CO_2$ atmosphere, and examined for the appearance of plaques under microscope. Monolayer of cells was fixed with 10% formalin, washed with water, stained with 0.8% crystal violet, and dried. Number of plaques counted in the sample well was compared with that in the virus control well, and the decrease in the number of plaques was used to express the antiviral activity.

Cytotoxicity Assay

Of the anti-viral activity assay procedures mentioned above, the virus infection step was omitted from sample wells, and cells were cultured in the presence of samples at various concentrations, and viable cell number was compared with that in the cell control well. Surviving cell number was counted by the tetrazolium method for the microplate assay.

2) Reverse Transcriptase Assay
a) Preparation of Host Cell and Virus

Each virus was obtained from ATCC. FIV was cultured with CRFK cells in Eagle's balanced salt medium containing 10% FBS, and the supernatant was used as the virus stock. As FeLV was used ATCC VR-717.

b) Preparation of Sample

Compound related to Example 29 was diluted with the medium to similar concentrations described above.

c) Assay Procedure

For each single strain of virus, the assay was performed in the following combinations of conditions.

| | |
|---|---|
| Medium control well | Culture medium |
| Cell control well | Culture medium + cell |
| Cytotoxicity well | Culture medium + cell + sample |
| Virus control well | Culture medium + cell + virus |
| test well | Culture medium + cell + virus + sample |
| Color control well | Culture medium + sample |

After CRFL cells were cultured in monolayer in 96-well microplates, the supernatant was discarded. Then, to the medium control well, the cell control well and the virus control well was added the medium (0.2 ml), and to the cytotoxicity well, the test well and the color control well was added the diluted sample solution at 0.2, 0.1, and 0.2 ml, respectively, and incubated under the 5–7% $CO_2$ atmosphere at 36–38° C. for 1 h. Then, supernatants of the virus control well and the test well were discarded, and the virus stock (0.1 ml) was added, and incubated further for 1 h. The, after supernatants were removed, and, to the virus control well was added the medium (0.2 ml), and to the test well the same volume of the diluted sample, then the incubation was further continued.

Reverse Transcriptase Assay by ELISA

Using supernatants as the sample from the cell control well, the virus control well and the test well, the reverse transcriptase of FIV or FeLV antigen contained therein were quantitated using assay kits from Amersham LIFESCIENCE and Synbiotics, respectively. Anti-viral activity was expressed as that ratio (%) of the value of the test well to that of the virus control well after both values were subtracted with the value of the cell control well, respectively.

Cytotoxicity Assay

Viable cell numbers in the cytotoxicity well and the cell control well were counted by the tetrazolium method for microplate assay similarly as described above, and the cytotoxicity was expressed as the ratio (%) of the cell number of the former to that of the latter.

Anti-viral Activity other than HIV and Cytotoxicity

Results of anti-viral activity assay are shown in the table below.

TABLE 3

Anti-viral activity of compound related to Example 29

| | IC50 ($\mu$M) | |
|---|---|---|
| Virus | Example 29 | Acyclovir |
| Herpes simplex II virus | 45.2 | 21.6 |
| Respiratory syncytial virus | 5.1 | — |
| Parainfluenza virus | 37.6 | — |
| Feline immunodeficiency virus | 4.5 | — |
| Feline leukemia virus | 58.3 | — |

These results indicate that the compound related to this invention has not only the anti-HIV activity but also the anti-viral activity against other viruses.

Furthermore, when CC50s were calculated for each virus by the similar method as described above, they all exceeded the value 500 $\mu$M. Compounds related to this invention have the anti-viral activity against other viruses and low cytotoxicity, indicating that they are not only effective in treating various diseases but also highly safe in the living body and effective as therapeutics.

Anti-coagulation Activity

To the human plasma (400 $\mu$l) were added compound diluted with physiological saline (500 $\mu$l) followed by 2% calcium chloride solution (100 $\mu$l), and the mixture was incubated at 37° C. for 30 min to determine the minimum concentration ($\mu$M) of said compound to exhibit the anti-coagulant activity. Plasma coagulation was judged with the naked eye.

Toxicity Study

Compounds were intravenously administered to mice, and LD50s (mg/kg) were determined.

Results of Anticoagulant Activity Assay and Toxicity Study

TABLE 4

| Minimum concentration exhibiting anticoagulant action ($\mu$M) | | LD50 (mg/kg) |
|---|---|---|
| Dextran sulfate | 0.5 | — |
| Example 12 | 900 | 2000 |
| Example 13 | 1200 | 2000 |
| Example 29 | 900 | 2000 |

These results indicate that compounds related to this invention are generally low not only in the cytotoxicity but also in the anticoagulant action, especially with compounds related to Examples 12, 13 and 29, furthermore they are low in the toxicity compounds related to Examples 12, 13 and 29, furthermore they are low in the toxicity to the living body. Therefore, it is obvious that pharmaceutics containing compounds related to this invention at the effective doses are preferable as drugs.

Effective dose of compounds related to this invention or the salts thereof can be determined by the general method well known to those skilled in the art including the method of establishing the dose-reaction curve in appropriate animal model or non-human primate and extrapolating its data to humans, or that of determining the dose in the clinical test.

Preferable doses of drugs, anti-viral agents and anti-HIV agents related to this invention are varied by various factors such as the severity of disease, body weight and age of individuals, half life of drug in the blood circulation, etc., and they can be easily determined by those skilled in the art.

Medicine related to this invention can be administered by various ways such as intravenous injection, oral administration, inhalation, etc. Pharmaceutical carriers, diluents and excipients can be easily selected by those skilled in the art according to the clinical use of drug, and, if necessary, supplements such as disintegrator, binder (including liposome), surfactant, emulsifier, buffer, solubilizing agent or preservative are added to make liquid preparation, emulsion or suspension.

As described above, novel compounds related to this invention have significant effectiveness such as not only the high antiviral activity but also the low cytotoxicity. Therefore, novel compounds related to the present invention are optimal as the antiviral agent.

Also, since novel compounds related to the present invention are low not only in the anticoagulant action but also in the toxicity to the living body, pharmaceutical preparations containing them in effective doses are preferable as medicine. In view of the bleeding tendency observed particularly with HIV patients, it is obvious that these novel compounds are extremely useful as the anti-HIV medicine.

What is claimed is:

1. A compound according to formula (I) or a salt thereof:

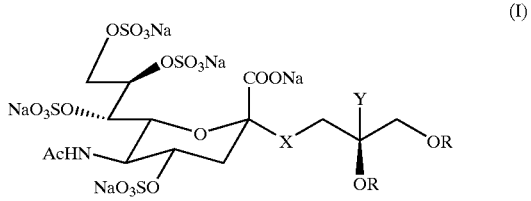

wherein Ac is acetyl; X is selected from the group consisting of oxygen and sulfur; Y is selected from the group consisting of H and an alkyl group having from 1 to 4 carbon atoms; and each R is independently selected from the group consisting of branched and linear alkyl chains having from 10 to 24 carbon atoms.

2. The compound according to claim 1, wherein Y is selected from the group consisting of H, $CH_3$ and $CH_2CH_3$.

3. The compound according to claim 2, wherein Y is selected from the group consisting of H and $CH_3$.

4. A pharmaceutical composition comprising the compound or salt of claim 3 and a pharmaceutically acceptable carrier.

5. A pharmaceutical composition comprising the compound or salt of claim 2 and a pharmaceutically acceptable carrier.

6. The compound according to claim 1, wherein X is O.

7. A pharmaceutical composition comprising the compound or salt of claim 6 and a pharmaceutically acceptable carrier.

8. The compound according to claim 1, wherein each R is the same.

9. The compound according to claim 8, wherein each R is a linear alkyl chain.

10. The compound according to claim 9, wherein each R has from 22 to 24 carbon atoms.

11. A pharmaceutical composition comprising the compound or salt of claim 10 and a pharmaceutically acceptable carrier.

12. A pharmaceutical composition comprising the compound or salt of claim 9 and a pharmaceutically acceptable carrier.

13. A pharmaceutical composition comprising the compound or salt of claim 8 and a pharmaceutically acceptable carrier.

14. The compound according to claim 1, selected from the group consisting of:
3-O-(sodium(5-acetamido-3,5-dideoxy-4,7,8,9-tetra-O-(sodium oxysulfonyl)-D-glycero-α-D-galacto-2-nonulopyranosyl)onate)-1,2-di-O-docosyl-Sn-glycerol,
3-O-(sodium(5-acetamido-3,5-dideoxy-4,7,8,9-tetra-O-(sodium oxysulfonyl)-D-glycero-β-D-galacto-2-nonulopyranosyl)onate)-1,2-di-O-docosyl-Sn-glycerol,
sodium(2,2-bis(docosyloxymethyl)butyl 5-acetamido-3,5-dideoxy-4,7,8,9-tetra-O-(sodium oxysulfonyl)-D-glycero-α-D-galacto-2-nonulopyranosid)onate, and
1-(N-(5-acetamido-3,5-dideoxy-2-O-methyl-4,7,8,9-tetra-O-(sodium oxysulfonyl)-D-glycero-β-D-galacto-2-nonulopyranosonyl) amino-2,2-bis (docosyloxymethyl) propane.

15. A pharmaceutical composition comprising the compound or salt of claim 14 and a pharmaceutically acceptable carrier.

16. A pharmaceutical composition comprising the compound or salt of claim 1 and a pharmaceutically acceptable carrier.

17. A method of treating a virus-mediated disease in a mammal comprising administering to said mammal a compound according to claim 1, or a salt thereof.

18. The method according to claim 17, wherein said compound is administered to said mammal by a route selected from the group consisting of an intravenous route, an intramuscular route, an intraperitoneal route, an intraarterial route, a subcutaneous route, a percutaneous route, a sublingual route, an inhalation route, a rectal route, and an oral route.

19. The method according to claim 17, wherein said virus is selected from the group consisting of a human immonodeficiency virus, a feline immunodeficiency virus, a feline leukemia virus, a herpes simplex II virus, a parainfluenza virus, a respiratory syncytial virus, and combinations thereof.

20. The method according to claim 19, wherein said virus is a respiratory syncytial virus.

21. The method according to claim 19, wherein said virus is a human immonodeficiency virus.

22. A compound or salt thereof selected from the group consisting of:
3-O-(sodium(5-acetamido-3,5-dideoxy-4,7,8,9-tetra-O-(sodiumoxysulfonyl)-D-glycero-α-D-galacto-2-nonulopyranosyl) onate)-1,2-di-Odecyl-Sn-glycerol,
3-O-(sodium(5-acetamido-3,5-dideoxy-4,7,8,9-tetra-O-(sodium oxysulfonyl)-D-glycero-β-D-galacto-2-nonulopyranosyl)onate)-1,2-di-O-decyl-Sn-glycerol,
3-O-(sodium(5-acetamido-3,5-dideoxy-4,7,8,9-tetra-O-(sodium oxysulfonyl)-D-glycero-α-D-galacto-2-nonulopyranosyl)onate)-1,2-di-O-tetradecyl-Sn-glycerol,
3-O-(sodium(5-acetamido-3,5-dideoxy-4,7,8,9-tetra-O-(sodium oxysulfonyl)-D-glycero-β-D-galacto-2-nonulopyranosyl)onate)-1,2-di-O-tetradecyl-Sn-glycerol,
3-O-(sodium(5-acetamido-3,5-dideoxy-4,7,8,9-tetra-O-(sodium oxysulfonyl)-D-glycero-α-D-galacto-2-nonulopyranosyl)onate)-1,2-di-O-octadecyl-Sn-glycerol,
3-O-(sodium(5-acetamido-3,5-dideoxy-4,7,8,9-tetra-O-(sodium oxysulfonyl)-D-glycero-α-D-galacto-2-nonulopyranosyl)onate)-2-O-(sodium oxysulfonyl)-1-O-octadecyl-Sn-glycerol,
3-O-(sodium(5-acetamido-3,5-dideoxy-4,7,8,9-tetra-O-(sodium oxysulfonyl)-D-glycero-β-D-galacto-2-nonulopyranosyl)onate)-2-O-(sodium oxysulfonyl)-1-O-octadecyl-Sn-glycerol,
3-O-(sodium(5-acetamido-3,5-dideoxy-4,7,8,9-tetra-O-(sodium oxysulfonyl)-D-glycero-α-D-galacto-2-nonulopyranosyl)onate)-1,2-di-O-docosyl-Sn-glycerol,
3-O-(sodium(5-acetamido-3,5-dideoxy-4,7,8,9-tetra-O-(sodium oxysulfonyl)-D-glycero-f3-D-galacto-2-nonulopyranosyl)onate)-1,2-di-O-docosyl-Sn-glycerol,
3-S-(sodium(5-acetamido-3,5-dideoxy-4,7,8,9-tetra-O-(sodium oxysulfonyl)-D-glycero-α-D-galacto-2-nonulopyranosyl)onate)-1,2-di-O-tetradecyl-Sn-thioglycerol,
3-O-(sodium(5-acetamido-3,5-dideoxy-4,7,8,9-tetra-O-(sodium oxysulfonyl)-D-glycero-α-D-galacto-2-nonulopyranosyl)onate)-1,2-di-O-eicosyl-Sn-glycerol,
3-O-(sodium(5-acetamido-3,5-dideoxy-4,7,8,9-tetra-O-(sodium oxysulfonyl)-D-glycero-α-D-galacto-2-nonulopyranosyl)onate)-1,2-di-O-tetracosyl-Sn-glycerol, 3β-(sodium(5-acetamido-3,5-dideoxy-4,7,8,9-tetra-O-(sodium oxysulfonyl)-D-glycero-α-D-galacto-2-nonulopyranosid)onate, sodium(oleyl 5-acetamido-3,5-dideoxy-4,7,8,9-tetra-O-(sodium oxysulfonyl)-D-glycero-α-D-galacto-2-nonulopyranosid)onate, sodium(octadecyl 5-acetamido-3,5-dideoxy-4,7,8,9-tetra-O-(sodium oxysulfonyl)-D-glycero-α-galacto-2-nonulopyranosid)onate, sodium(2,2-bis(eicosyl oxymethyl)propyl 5-acetamido-3,5-dideoxy-4,7,8,9-tetra-O-(sodium oxysulfonyl)-D-glycero-α-D-galacto-2-nonulopyranosid)onate, sodium(3,5-didocosyloxyphenyl-5-acetamido-3,5-dideoxy-4,7,8,9-tetra-O-(sodium oxysulfonyl)-D-glycero-β-D-galacto-2-nonulopyranosid)onate, 3-O-(sodium(5-acetamido-3,5-dideoxy-4,7,8,9-tetra-O-(sodium oxysulfonyl)-D-glycero-α-galacto-2-nonulopyranosyl)onate)-1,2-di-O-docosanoyl-Sn-glycerol, 3-O-(sodium(3-deoxy-4,5,7,8,9-penta-O-(sodium oxysulfonyl)-D-glycero-a-D-galacto-2-nonulopyranosyl)onate)-1,2-di-O-docosyl-Sn-glycerol, sodium(2,2-bis(docosyloxymethyl)butyl 5-acetamido-3,5-dideoxy-4,7,8,9-tetra-O-(sodium oxysulfonyl)-D-glycero-α-D-galacto-2-nonulopyranosid)onate, 1-(N-(5-acetamido-3,5-dideoxy-2-O-methyl-4,7,8,9-tetra-O-(sodium oxysulfonyl)-D-glycero-β-D-galacto-2-nonulopyranosonyl)amino)-2,2-bis(docosyloxymethyl) propane, and salts thereof.

23. A pharmaceutical composition comprising the compound or salt of claim 22 and a pharmaceutically acceptable carrier.

24. A method of treating a virus-mediated disease in a mammal comprising administering to said mammal a compound according to claim 22, or a salt thereof.

25. The method according to claim 24, wherein said compound is administered to said mammal by a route selected from the group consisting of an intravenous route, an intramuscular route, an intraperitoneal route, an intra-arterial route, a subcutaneous route, a percutaneous route, a sublingual route, an inhalation route, a rectal route, and an oral route.

26. The method according to claim 24, wherein said virus is selected from the group consisting of a human immonodeficiency virus, a feline immunodeficiency virus, a feline leukemia virus, a herpes simplex II virus, a parainfluenza virus, a respiratory syncytial virus, and combinations thereof.

27. The method according to claim 26, wherein said virus is a respiratory syncytial virus.

28. The method according to claim 26, wherein said virus is a human immonodeficiency virus.

* * * * *